(12) United States Patent
Broo et al.

(10) Patent No.: US 9,181,181 B2
(45) Date of Patent: Nov. 10, 2015

(54) 2-SUBSTITUTED-3-PHENYLPROPIONIC ACID DERIVATIVES AND THEIR USE IN THE TREATMENT OF INFLAMMATORY BOWEL DISEASE

(71) Applicant: Albireo AB, Gothenburg (SE)

(72) Inventors: Anders Broo, Mölndal (SE); Johan Gottfries, Mölndal (SE); Michael Kossenjans, Mölndal (SE); Li Lanna, Mölndal (SE); Eva-Lotte Lindstedt-Alstermark, Mölndal (SE); Kristina A. Nilsson, Mölndal (SE); Bengt Ohlsson, Mölndal (SE); Maria Thorstensson, Mölndal (SE); Maria Boije, Mölndal (SE)

(73) Assignee: Albireo AB, Gothenburg (SE)

( * ) Notice: Subject to any disclaimer, the term of this patent is extended or adjusted under 35 U.S.C. 154(b) by 0 days.

(21) Appl. No.: 14/301,569

(22) Filed: Jun. 11, 2014

(65) Prior Publication Data

US 2014/0303175 A1    Oct. 9, 2014

Related U.S. Application Data

(60) Division of application No. 13/046,288, filed on Mar. 11, 2011, now Pat. No. 8,785,681, which is a continuation of application No. 12/530,443, filed as application No. PCT/SE2008/050259 on Mar. 7, 2008, now abandoned.

(60) Provisional application No. 60/893,681, filed on Mar. 8, 2007, provisional application No. 60/893,683, filed on Mar. 8, 2007, provisional application No. 60/893,689, filed on Mar. 8, 2007, provisional application No. 60/893,695, filed on Mar. 8, 2007.

(51) Int. Cl.

| | | |
|---|---|---|
| C07C 321/00 | (2006.01) |
| C07C 323/00 | (2006.01) |
| C07C 325/00 | (2006.01) |
| C07C 335/00 | (2006.01) |
| C07C 381/00 | (2006.01) |
| C07C 323/56 | (2006.01) |
| C07C 271/28 | (2006.01) |
| C07C 309/66 | (2006.01) |
| C07C 317/44 | (2006.01) |
| C07C 323/62 | (2006.01) |
| C07C 327/28 | (2006.01) |
| C07D 213/55 | (2006.01) |
| C07D 231/12 | (2006.01) |
| C07D 263/32 | (2006.01) |
| C07D 263/34 | (2006.01) |
| C07D 277/24 | (2006.01) |
| C07D 277/30 | (2006.01) |
| C07D 295/04 | (2006.01) |

(52) U.S. Cl.
CPC ............ *C07C 323/56* (2013.01); *C07C 271/28* (2013.01); *C07C 309/66* (2013.01); *C07C 317/44* (2013.01); *C07C 323/62* (2013.01); *C07C 327/28* (2013.01); *C07D 213/55* (2013.01); *C07D 231/12* (2013.01); *C07D 263/32* (2013.01); *C07D 263/34* (2013.01); *C07D 277/24* (2013.01); *C07D 277/30* (2013.01); *C07D 295/04* (2013.01)

(58) Field of Classification Search
None
See application file for complete search history.

(56) References Cited

U.S. PATENT DOCUMENTS

| | | |
|---|---|---|
| 6,506,797 B1 | 1/2003 | Nomura et al. |
| 6,884,821 B1 | 4/2005 | Shinoda et al. |
| 6,906,058 B2 | 6/2005 | Starke et al. |
| 7,125,864 B2 | 10/2006 | Starke et al. |
| 7,132,416 B2 | 11/2006 | Starke et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,402,581 B2 | 7/2008 | Johansson et al. |
| 7,514,421 B2 | 4/2009 | Abrahamsson et al. |
| 8,067,584 B2 | 11/2011 | Starke et al. |
| 8,106,208 B2 | 1/2012 | Johansson et al. |
| 2006/0079696 A1 | 4/2006 | Masson et al. |
| 2006/0083790 A1 | 4/2006 | Anderberg et al. |
| 2006/0167309 A1 * | 7/2006 | Lindstedt-Alstermark et al. .............. 562/402 |
| 2007/0248995 A1 | 10/2007 | Drmota et al. |
| 2007/0270399 A1 | 11/2007 | Fredenwall et al. |
| 2007/0270400 A1 | 11/2007 | Johansson |
| 2008/0146538 A1 | 6/2008 | Antonsson |
| 2010/0069346 A1 | 3/2010 | Holmqvist et al. |

FOREIGN PATENT DOCUMENTS

| | | |
|---|---|---|
| EP | 1375472 | 1/2004 |
| EP | 1607103 | 12/2005 |

(Continued)

OTHER PUBLICATIONS

PCT International Search Report for PCT/SE2008/050259, mailed Aug. 11, 2008.

(Continued)

*Primary Examiner* — Clinton Brooks
(74) *Attorney, Agent, or Firm* — Fish & Richardson P.C.

(57) ABSTRACT

The present invention relates to 2-(substituted sulphur, sulphone or sulphoxide)-3-(substituted phenyl)propionic acid derivatives, 2-(substituted oxygen)-3-(substituted phenyl) propionic acid derivatives, benzoic acid derivatives, and derivatives of 2-methyl-2-(phenoxy or phenylthio)propanoic acid and 2-(methyl or ethyl)-2-(phenoxy or phenylthio)butanoic acid, to processes for preparing such compounds, to their use in the treatment of inflammatory conditions, and to pharmaceutical compositions containing them.

22 Claims, No Drawings

(56) References Cited

FOREIGN PATENT DOCUMENTS

| WO | WO 01/40207 | 6/2001 |
| WO | WO 03/051826 | 6/2003 |
| WO | WO 2004/092145 | 10/2004 |
| WO | WO 2005/054176 | 6/2005 |
| WO | WO 2005/105724 | 11/2005 |
| WO | WO 2005/105764 | 11/2005 |
| WO | WO 2006/032023 | 3/2006 |
| WO | WO 2006/041197 | 4/2006 |
| WO | WO 2006/137791 | 12/2006 |

OTHER PUBLICATIONS

Cabrero et al., "Differential effects of peroxisome proliferator-activated receptor activators on the mRNA levels of genes involved in lipid metabolism in primary human monocyte-derived macrophages," *Metabolism*, 2003, 52(5):652-657.

Supplementary European Search Report in European Application No. EP08724206, dated Oct. 4, 2011, 11 pages.

International Preliminary Report on Patentability in International Application No. PCT/SE2008/050259, issued Sep. 8, 2009, 10 pages.

Masahiro et al., "Design, synthesis, and evaluation of substituted phyenylpropanoic acid derivatives as human peroxisome proliferator activated receptor activators. Discovery of potent and human peroxisome proliferator activated receptor alfa subtype-selective activators," *J. Med. Chem.*, 46: p. 3581-3599 (2003).

Nassar et al., "Improving the decision-making process in the structural modification of drug candidates: enhancing metabolic stability," *DDT*, 2004, 9(23):1020-1028.

Patani, et al., "Bioisosterism: A rational approach in drug design," *Chem. Rev.*, 96(8): p. 3147-3176 (1996).

Pathak, et al., "Effect of peroxisome proliferator-activated receptor-alpha agonist (bezafibrate) on gastric secretion and gastric cytoprotection in rats," *Fund. & Clin. Pharma.*, 21(3): p. 291-296 (2007).

Rucker et al., "2D QSAR of PPARγ agonist binding and transactivation," *Bio. & Med. Chem.*, 14: p. 5178-5195 (2006).

Szeles, et al., "PPAR gamma in immunity and inflammation: cell types and diseases," *Bio. et Biophysica Acta.*, 1771(8): p. 1014-1030 (2007).

\* cited by examiner

2-SUBSTITUTED-3-PHENYLPROPIONIC ACID DERIVATIVES AND THEIR USE IN THE TREATMENT OF INFLAMMATORY BOWEL DISEASE

CROSS REFERENCE TO RELATED APPLICATIONS

This application is a divisional of U.S. patent application Ser. No. 13/046,288, filed on Mar. 11, 2011, which is a continuation of U.S. patent application Ser. No. 12/530,443, filed Sep. 16, 2010, which is a U.S. National Phase Application under 35 U.S.C. §371 of International Application No. PCT/SE2008/050259, filed Mar. 7, 2008, and claims the benefit of priority to U.S. Provisional Application Ser. Nos. 60/893,681, 60/893,683, 60/893,689, and 60/893,695, all filed Mar. 8, 2007. The disclosure of each of the above applications is incorporated herein by reference in its entirety.

FIELD OF THE INVENTION

The present invention relates to 2-(substituted sulphur, sulphone or sulphoxide)-3-(substituted phenyl)propionic acid derivatives, 2-(substituted oxygen)-3-(substituted phenyl) propionic acid derivatives, benzoic acid derivatives, and derivatives of 2-methyl-2-(phenoxy or phenylthio)propanoic acid and 2-(methyl or ethyl)-2-(phenoxy or phenylthio)butanoic acid, to processes for preparing such compounds, to their use in the treatment of inflammatory conditions, and to pharmaceutical compositions containing them.

BACKGROUND OF THE INVENTION

Inflammatory Bowel Disease (IBD) includes conditions where the patients suffer from inflammation in the gastrointestinal (GI)-tract. Several of those are considered to be of chronic nature, e.g. Crohn's disease and ulcerative colitis, and the medical need is large. The patients suffer from fevers, pain, diarrhea or constipation and in addition hemorrhagic stool. Treatment is constrained to symptom relief, inflammatory suppression and in severe cases surgery and which all current treatment are linked to relatively severe side effects. Anti-inflammatory treatments with oral gluco-corticoid receptor (GCR) agonists (e.g. Budesonide, Prednisolone or Fluticazone) can cause diabetes, Cushing's syndrome, skin defects. In addition GCR agonist treatment suppresses life saving immuno-activation upon infection by virus, bacteria or other pathogenic microbes, which further reduces patient quality of life and increases risk for secondary disease. Non-Steroidal Anti-Inflammatory Drugs (NSAID) and antibiotics (e.g. 5-ASA, Sulfasalazine, and Metronidazole) are also commonly used, however with limited effect. Similar reasoning as above is also relevant for other inflammatory diseases such as asthma and Chronic Obstructive Pulmonary Disease (COPD). Thus, there is a great need for more effective anti-inflammatory treatments with less or preferably no side effects.

The nuclear hormone receptors (NHRs) comprise a series of soluble protein complexes that upon ligand modulation and co-factor complexation translocate to the cellular nucleus with subsequent binding to specific DNA regions. Such binding induces or reduces protein expression cascades and, for several NHRs, immunoactivation or deactivation has been implicated. For example, Oestrogen receptors (Steffan et al, 2006), the Liver X Receptor (LXR) (Tontonoz et al, US2004/0259948; Zelcer & Tontonoz, 2006) and the Peroxisome Proliferator Activated Receptor (PPAR)-α, γ and/or δ, (Desreumaux et al, 2001; Tanaka et al, 2001; Lewis et al, 2001; Patel et al; 2003) have all been suggested to exert such immuno-modulatory effects via small molecular modulators. NHRs are in general multi-potent in the sense that they regulate several profound physiological events, either simultaneously or sequentially, depending on the cell type or tissue in which the modulation is accomplished. This might also be the reason for unwanted effects from these NHR modulators, which are in parallel with the mechanism related side effects observed with the GCR modulators.

The regulation of inflammatory responses by PPARs have been suggested to involve the trans-repression of inflammatory gene activation by interfering with several signalling pathways of the transcription factors NFkB, STAT-1, NFAT and AP-1. As a result of this interaction, a number of downstreams pathways are affected. These includes the downregulation of pro-inflammatory cytokines (e.g., IL-1β, IL-6, TNF) or chemokines (e.g., MCP-1, IL-8), decrease expression of adhesion molecules (e.g., V-CAM) resulting in reduced leukocyte recruitment. Other anti-inflammatory effects include the decreased expression of oxidative stress markers (e.g., iNOS, COX-2), the repressed expression of extra cellular matrix components (e.g., MMPs, TGF-β), as well as induced apoptosis in a variety of cell types (Belvisi M et al., 2006; Duboquoy L et al., 2006; Cunard R 2005). In addition to its anti-inflammatory action, PPARs have also been suggested to have anti-proliferative properties, possibly as a result of induction of cell cycle arrest and/or apoptosis (Galli A et al., 2006).

Compounds delivered orally initially expose the GI-tract and an inhaled compound the respiratory organs when administered to patients. Given the above reasoning it would be advantageous, for a patient with GI inflammation, for a compound to have properties such that it exposes the GI tract but is designed to be eliminated or metabolized before it reaches cells, tissues or body compartments where it can induce unwanted effects. A method to accomplish this has been introduced by Bodor and co-workers (Bodor et al, 1995; Bodor & Buchwald, 2006; Bodo & Bodor, WO 9200988), who named it "soft-drugs", meaning a drug that exerts its pharmacological or medicinal effects during a controlled time frame in a controlled compartment, and thereafter is "soft" in the sense that it is predestined to elimination by metabolism in a predicted way.

The definition of the term "soft drug" varies. In this patent application, the definition of the term "soft drug" is a chemical compound that exerts its activity in the target organ, and subsequent inactivation or alteration by metabolism is such that receptor modulation within other compartments (e.g. systemic compartments) is excluded and unwanted effects and/or side effects that are disadvantageous, or of no use, for the patient is reduced.

US 2003/0236227 discusses the use of soft drugs for the treatment of diabetes, hyperlipidemia, hypercholesterolemia, and atherosclerosis. However, these soft drugs have activity in the systemic compartment, and thus they do not fall within the definition of the term "soft drugs" in this patent application. Further, US 2003/0236227 is silent about compounds having anti-inflammatory properties.

As discussed above, there remains a need for compounds having anti-inflammatory properties. In particular, there is a need for compounds with anti-inflammatory effect and having the property of being locally active in the target organ with little or no effect in other compartments (e.g. systemic compartments).

Accordingly, we hereby provide compounds with anti-inflammatory properties which are believed to act according to the definition of the term "soft drug" in the present patent application.

The term "PPAR modulator" as used herein, refers to the ability of a compound to modulate the biological activity of PPARα and/or PPARγ and/or PPARδ via increase or decrease of the function and/or expression of PPARα and/or PPARγ and/or PPARδ, where PPARα and/or PPARγ and/or PPARδ function may include transcription regulatory activity and/or protein-binding. Modulation may occur in vitro or in vivo. Modulation, as described herein, includes antagonism, agonism, partial antagonism and/or partial agonism of a function or characteristic associated with PPARα and/or PPARγ and/or PPARδ, either directly or indirectly, and/or the upregulation or downregulation of PPARα and/or PPARγ and/or PPARδ expression, either directly or indirectly. More specifically, such a PPAR modulator either enhances or inhibits the biological activities of PPAR via the function and/or expression of PPAR. If such a modulator partially or completely enhances the biological activities of PPAR via the function and/or expression of PPAR, it is a partial or full PPAR agonist, respectively. It is the object of the present invention to provide PPAR modulators. Another object of this invention is to provide PPAR modulator compounds being PPAR agonists.

To aid understanding the terms "local" and "systemic" compartments, for oral administration the local compartment is the GI tract (i.e. gastrointestinal tract); when a compound has passed beyond/through the liver it has reached the systemic compartment. For inhaled compounds the lung is the local compartment, and beyond the lung is the systemic compartment.

By systemic compartment we mean any tissue or organ that an administrated compound reaches after it has passed beyond/through another tissue or organ in which some (e.g. 90%, but also including 100%) elimination or metabolism of the compound as occurred.

An aim with PPAR soft drugs for IBD should be to not accept predicted human systemic exposure higher than a factor (e.g. 10) below a corresponding exposure that would give an expected pharmacological effect in dyslipidemic patients.

It should be noted that to show activity in the specific Test Methods described herein, the PPAR modulator compound must bind to the ligand binding domain of the PPAR and recruit one or more of the nuclear hormone receptor co-factors present in the U-2 OS cell-based method described herein. The compounds of this invention that form an PPAR-modulator compound-complex may recruit at least one or more of the other >80 known different nuclear hormone receptor cofactors in any other cell-based method, prepared and assayed according to known procedures. Compounds according to Formula I, XI, CI and MI, that do not recruit any of the co-factors present in the in cell-based method described herein, are however anticipated to bind to PPAR and the PPAR-modulator compound-complex so formed will recruit at least one or more of the other >80 known different nuclear receptor co-factors present in other cellular systems. The PPAR modulator compound-complex may also displace co-repressors, with simultaneous recruitment of a co-activator or alternatively displace a co-repressor without co-activator recruitment, leading to partial activation of certain PPAR regulated genes. Peptides derived from any of these other nuclear hormone receptor co-factors may be similarly prepared and assayed according to known procedures.

DESCRIPTION OF THE INVENTION

The following definitions shall apply throughout the specification and the appended claims unless specifically stated otherwise:

The term" "$C_1$alkyl" denotes an alkyl group having 1 carbon atom. An example of "$C_1$alkyl" is methyl.

The term"$C_2$alkyl" denotes an alkyl group having 2 carbon atoms. An example of "$C_2$alkyl" is ethyl.

The term "$C_1$-$C_2$alkyl" denotes an alkyl group having 1 or 2 carbon atoms. Examples of "$C_1$-$C_2$alkyl" are methyl or ethyl.

The term "$C_1$-$C_3$alkyl" denotes a straight or branched saturated alkyl group having 1 to 3 carbon atoms. Examples of said alkyl include, but are not limited to, methyl, ethyl, propyl, and isopropyl.

The term "$C_1$-$C_4$alkyl" denotes a straight or branched saturated alkyl group having 1 to 4 carbon atoms. Examples of said alkyl include, but are not limited to, methyl, ethyl, propyl, isopropyl, butyl, isobutyl, and tert-butyl.

The term "branched $C_3$-$C_4$alkyl" denotes a branched saturated alkyl group having 3 to 4 carbon atoms. Examples of said alkyl include isopropyl, isobutyl, sec-butyl and tert-butyl.

The term "$C_1$-$C_6$alkyl" denotes a straight or branched saturated alkyl group having 1 to 6 carbon atoms. Examples of said alkyl include, but are not limited to, methyl, ethyl, propyl, isopropyl, butyl, isobutyl, tert-butyl, pentyl and hexyl.

The term "$C_2$-$C_3$alkenyl" denotes a straight or branched unsaturated alkenyl group having 2 to 3 carbon atoms. Examples of said alkyl include, but are not limited to, vinyl, and allyl.

The term "$C_1$-$C_2$alkoxy" denotes an alkyl group containing one or two carbon atoms linked to an oxygen atom. Examples of said $C_1$-$C_2$alkoxy include methoxy and ethoxy The term "$C_1$-$C_3$alkylaryl" denotes an alkyl chain containing one to three carbon atoms linked to an aryl group. It shall be understood that when $R^2$ in compounds of formula I, XI, CI, MI represents $C_1$-$C_3$alkylaryl it binds to X via the alkyl chain.

The term "$C_1$-$C_3$alkylheteroaryl" denotes an alkyl chain containing one to three carbon atoms linked to an heteroaryl group. It shall be understood that when $R^2$ in compounds of formula I, XI, CI, MI represents $C_1$-$C_3$alkylheteroaryl it binds to X via the alkyl chain.

The term "halogen" denotes fluoro, chloro, bromo and iodo groups.

The term "aryl" denotes an aromatic monocyclic ring composed of 6 carbon atoms or a fully aromatic bicyclic ring system composed of 10 carbon atoms. Examples of said "aryl" include, but are not limited to, phenyl, naphtalene and azulene.

The term "heteroaryl" denotes an aromatic 5 or 6 membered monocyclic ring or an aromatic 9 or 10 membered bicyclic ring in which one or more of the atoms in the monocyclic ring or bicyclic ring system is an element other than carbon independently selected from one or more of for example nitrogen, oxygen or sulfur. The term "sulfur" shall be understood to include sulphoxide (S(O)) and sulphone ($SO_2$). The term "nitrogen" shall be understood to include nitrogen oxide (NO). Examples of said "heteroaryl" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole 1,2,3-thiadiazole, benzofuran, isobenzofuran, indole, isoindole, benzothiophene, benzo[c] thiophene, benzimidazole, purine, indazole, benzoxazole, benzisoxazole, benzthiazole, quinoline, quinoxaline, quinazoline, cinnoline and isoquinoline.

The term "cycloalkyl" denotes a saturated or unsaturated non-aromatic monocarbocyclic ring composed of 3, 4, 5, 6, 7 or 8 carbon atoms or a saturated or unsaturated non-aromatic bicyclic ring system composed of 8, 9 or 10 carbon atoms. Examples of said "cycloalkyl" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl, cyclooctadienyl, decaline, and hydrindane.

The term "heterocyclyl" denotes a saturated or unsaturated non-aromatic 3, 4, 5, 6, 7, 8, 9 or 10 membered monocyclic ring or a saturated or unsaturated non-aromatic or partly aromatic 9 or 10 membered bicyclic ring system in which one or more of the atoms in the monocyclic ring or bicyclic ring system is an element other than carbon independently selected from one or more of for example nitrogen, oxygen or sulfur. The term "sulfur" shall be understood to include sulphoxide (S(O)) and sulphone (SO$_2$). The term "nitrogen" shall be understood to include nitrogen oxide (NO). Examples of said "heterocyclyl" include, but are not limited to, aziridine, azetidine, 2-pyrroline, 3-pyrroline, pyrrolidine, imidazoline, piperidine, piperazine, 2-pyrazoline, oxirane, oxetane, tetrahydrofuran, furan, tetrahydropyran, 1,4-dioxane 1,3-dioxolane, 1,2-oxathiolane, morpholine, 3-pyrazoline, pyrazolidine, 2H-pyrane, 4H-pyrane, 1,4-dithiane, 1,4-oxathiane, thiomorpholine, indoline, chroman, isochroman, 2,3-dihydrobenzofuran, phtalan, and isoindoline.

$R^a$ independently represents H or a straight or branched, saturated or unsaturated $C_1$-$C_4$alkyl chain optionally substituted by one or more F.

$R^b$ independently represents a straight or branched, saturated or unsaturated $C_1$-$C_4$alkyl chain optionally substituted by one or more F.

It shall be understood that when a substituent bears more than one of $R^a$ or $R^b$ then each of these may be the same or different. For example, $NR^aR^a$ includes amino, alkylamino and dialkylamino. Furthermore, it shall be understood that when different substituents in the same compound bear more than one of $R^a$ or $R^b$ then each of these may be the same or different.

According to one aspect of the invention there is provided a compound of the general formula (I')

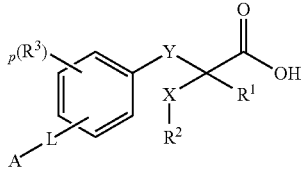

formula I' wherein
Y is C, O or S
$R^1$ represents H, F, CH$_3$ or CF$_3$; when Y is C, S, S(O) or SO$_2$ and $C_1$-$C_2$alkyl optimally substituted with one or more F when Y is O or S
X represents C, O, S, S(O) or SO$_2$; when Y is C and X is O, S, S(O) or SO$_2$
$R^2$ represents straight $C_1$-$C_6$alkyl or branched $C_3$-$C_4$alkyl, each optionally substituted by one or more F,
or $R^2$ is $C_1$-$C_3$alkylaryl or $C_1$-$C_3$alkylheteroaryl, wherein aryl or heteroaryl each optionally is substituted by one or more of the following: halogen, OH, OSO$_2R^b$, $C_1$-$C_2$alkoxy, $C_1$-$C_4$alkyl, which $C_1$-$C_2$alkoxy or $C_1$-$C_4$alkyl substituents is each optionally substituted by one or more F; when Y is S and X is C $R^2$ is methyl optionally substituted by one or more F $R^3$ is situated in the ortho, meta or para position and represents F, $C_1$-$C_4$alkyl or $C_1$-$C_2$alkoxy, which $C_1$-$C_4$alkyl or $C_1$-$C_2$alkoxy substituents is each optionally substituted by one or more F;
or $R^3$ is CH$_2$Ph, or NHC(O)OC(CH$_3$)$_3$;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy each optionally is substituted with one or more F;
n is an integer 0-3;
i is an integer 0-3;

A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl which is optionally substituted by one or more F,
or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $OS(O)R^b$, $S(O)R^b$, $SO_2R^b$, $NO_2$, $C(O)R^b$, $C_1$-$C_4$alkyl (which is optionally substituted by one or more F);

and in the above definitions
$C_1$-$C_3$alkylaryl binds to X via the alkyl chain;
$C_1$-$C_3$alkylheteroaryl binds to X via the alkyl chain;
$R^a$ independently represents H or a straight or branched, saturated or unsaturated $C_1$-$C_4$alkyl chain optionally substituted by one or more F; and
$R^b$ independently represents a straight or branched, saturated or unsaturated $C_1$-$C_4$alkyl chain optionally substituted by one or more F;
or a pharmaceutically acceptable salt thereof.

According to another aspect of the invention there is provided a compound of formula (I):

formula I

[Chemical structure showing a benzene ring with (R³)ₚ substituent, L-A group, and a side chain -CH(X-R²)(R¹)-C(O)OH]

wherein
$R^1$ represents H, F, $CH_3$ or $CF_3$;
X represents S, S(O) or $SO_2$;
$R^2$ represents straight $C_1$-$C_6$alkyl or branched $C_3$-$C_4$alkyl, each optionally substituted by one or more F,
or $R^2$ is $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl substituents is each optionally substituted by one or more F;
$R^3$ is situated in the ortho, meta or para position and represents F,
  $C_1$-$C_4$alkyl or $C_1$-$C_2$alkoxy, which $C_1$-$C_4$alkyl or $C_1$-$C_2$alkoxy substituents is each optionally substituted by one or more F;
or $R^3$ is $CH_2Ph$, or $NHC(O)OC(CH_3)_3$;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy substituents is each optionally substituted with one or more F;
n is an integer 0-3;
i is an integer 0-3;
A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F),
or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$ $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $OS(O)R^b$, $S(O)R^b$, $SO_2R^b$, $NO_2$, $C(O)R^b$, $C_1$-$C_4$alkyl (which is optionally substituted by one or more F); or a pharmaceutically acceptable salt thereof.

Further values of $R^1$, X, $R^2$, $R^3$, p, n, i, L and A in compounds of formula I now will follow. It will be understood that such values may be used where appropriate with any of the definitions, claims or embodiments defined hereinbefore or hereinafter.

In a first embodiment of the invention there is provided a class of compounds of formula I wherein
$R^1$ represents H, F, $CH_3$ or $CF_3$;
X represents S, S(O) or $SO_2$;
$R^2$ represents straight $C_1$-$C_6$alkyl or branched $C_3$-$C_4$alkyl, each optionally substituted by one or more F,
or $R^2$ is $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl substituents is each optionally substituted by one or more F;
$R^3$ is situated in the ortho, meta or para position and represents F,
  $C_1$-$C_4$alkyl or $C_1$-$C_2$alkoxy, each optionally substituted by one or more F;
or $R^3$ is $CH_2Ph$, or $NHC(O)OC(CH_3)_3$;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy substituents is each optionally substituted with one or more F;
n is an integer 0-3;
i is an integer 0-3;
A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$ $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $OS(O)R^b$, $S(O)R^b$, $SO_2R^b$, $NO_2$, $C(O)R^b$, $C_1$-$C_4$alkyl (which is optionally substituted by one or more F).

In a second embodiment of the invention there is provided a class of compounds of formula I wherein $R^2$ represents $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl substituents is each optionally substituted by one or more F;

$R^1$, X, $R^3$, p, L, n, i, and A are the same as for the first embodiment.

In a third embodiment of the invention there is provided a class of compounds of formula I wherein $R^2$ represents $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl each substituents is optionally substituted by one or more F;

A represents aryl or heteroaryl, each optionally substituted by one or more of the following independently selected from: halogens, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl which is optionally substituted by one or more F, or A is heterocyclyl optionally substituted by one or more of the following independently selected from: F, OH oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $OS(O)R^b$, $S(O)R^b$, $SO_2R^b$, $NO_2$, $C(O)R^b$, $C_1$-$C_4$alkyl (which is optionally substituted by one or more F);

$R^1$, X, $R^3$, p, L, n, and i are the same as for the first embodiment.

In a fourth embodiment of the invention there is provided a class of compounds of formula I wherein $R^1$ represents H;

X represents S or $SO_2$;

$R^2$ represents $C_2$alkylaryl, wherein aryl optionally is substituted by one or more of F;

L is situated in the meta or para position and represents $(CH_2)_nC(O)O(CH_2)_i$, $(CH_2)_nOC(O)(CH_2)_i$, or $(CH_2)_nSC(O)(CH_2)_i$, each optionally substituted on any available carbon atom with one $C_1$alkyl;

n is an integer 0-2;

i is an integer 0-3;

p is 0;

A represents aryl or heteroaryl, each optionally substituted by one or more of the following: $OR^b$, $OSO_2R^b$, $C_1$-$C_4$alkyl (which is optionally substituted by one or more F); monocyclic aryl;

or A is heterocyclyl optionally substituted by $C_1$alkyl, which $C_1$alkyl optionally is substituted by one or more F.

In a fifth embodiment of the invention there is provided a class of compounds of formula I wherein $R^1$ represents H;

X represents S;

$R^2$ represents $C_2$alkylaryl, wherein aryl is substituted by one F;

L is situated in the meta or para position and represents $(CH_2)_nC(O)O(CH_2)_i$, or $(CH_2)_nOC(O)(CH_2)_i$;

n is an integer 0-1;

i is an integer 0-1;

p is 0;

A represents aryl or heteroaryl, each optionally substituted by one or more of the following: $OR^b$, $OSO_2R^b$, $C_1$alkyl (which is optionally substituted by one or more F); monocyclic aryl;

or A is heterocyclyl optionally substituted by $C_1$alkyl, which $C_1$alkyl optionally is substituted by one or more F.

According to another aspect of the invention there is provided a compound of formula (XI):

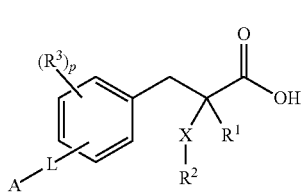

formula XI wherein $R^1$ represents H, F, $CH_3$ or $CF_3$;

X represents O;

$R^2$ represents straight $C_1$-$C_1$alkyl or branched $C_3$-$C_4$alkyl, each optionally substituted by one or more F, or $R^2$ is $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl substituents is each optionally substituted by one or more F;

$R^3$ is situated in the ortho, meta or para position and represents F,
  $C_1$-$C_4$alkyl, or $C_1$-$C_2$alkoxy, which $C_1$-$C_4$alkyl or $C_1$-$C_2$alkoxy substituents is each optionally substituted by one or more F;

or $R^3$ is $CH_2Ph$, or $NHC(O)OC(CH_3)_3$;

p is an integer 0-4;

L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy each optionally is substituted with one or more F;

n is an integer 0-3;

i is an integer 0-3;

A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F);

or a pharmaceutically acceptable salt thereof

Further values of $R^1$, X, $R^2$, $R^3$, p, n, i, L and A in compounds of formula XI now will follow. It will be understood that such values may be used where appropriate with any of the definitions, claims or embodiments defined hereinbefore or hereinafter.

In a sixth embodiment of the invention there is provided a class of compounds of formula XI wherein $R^1$ represents H, F, $CH_3$ or $CF_3$;

X represents O;

$R^2$ represents straight $C_1$-$C_6$alkyl or branched $C_3$-$C_4$alkyl, each optionally substituted by one or more F, or $R^2$ is $C_1$-$C_3$alkylaryl or $C_1$-$C_3$alkylheteroaryl, wherein aryl or heteroaryl each optionally is substituted by one or more of the following: halogen, OH, $OSO_2R^b$, $C_1$-$C_2$alkoxy, $C_1$-$C_4$alkyl, which $C_1$-$C_2$alkoxy or $C_1$-$C_4$alkyl substituents is each optionally substituted by one or more F;

$R^3$ is situated in the ortho, meta or para position and represents F,
  $C_1$-$C_4$alkyl or $C_1$-$C_2$alkoxy, which $C_1$-$C_4$alkyl or $C_1$-$C_2$alkoxy substituents is each optionally substituted by one or more F;

or $R^3$ is $CH_2Ph$, or $NHC(O)OC(CH_3)_3$;

p is an integer 0-4;

L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy each optionally is substituted with one or more F;

n is an integer 0-3;

i is an integer 0-3;

A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), or A is cycloalkyl or heterocyclyl, each optionally substituted by one or more of the following independently selected from: F, OH, oxo, CN, $NR^aR^a$, $OR^b$. $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F);

or a pharmaceutically acceptable salt thereof

In a seventh embodiment of the invention there is provided a class of compounds of formula XI wherein $R^2$ represents straight $C_1$-$C_6$alkyl or branched $C_3$-$C_4$alkyl, each optionally substituted by one or more F;

$R^1$, X, $R^3$, p, L, n, i and A are the same as for the sixth embodiment.

In a eighth embodiment of the invention there is provided a class of compounds of formula XI wherein $R^2$ represents straight $C_1$-$C_6$alkyl or branched $C_3$-$C_4$alkyl, each optionally substituted by one or more F, A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), $R^1$, X, $R^3$, p, L, n, and i are the same as for the sixth embodiment.

In a ninth embodiment of the invention there is provided a class of compounds of formula XI wherein $R^1$ represents H;

$R^2$ represents $C_2$alkyl;

L is situated in the meta or para position and represents $(CH_2)_nC(O)O(CH_2)_i$, or $(CH_2)_nOC(O)(CH_2)_i$;

n is an integer 0-1;

i is an integer 0-1;

p is 0;

A represents aryl or heteroaryl, each optionally substituted by one or more of the following independently selected from: monocyclic aryl, $C_1$-$C_4$alkyl (which is optionally substituted by one or more F), $NR^aC(O)OR^b$, $OSO_2R^b$;

X is the same as for the sixth embodiment.

In a tenth embodiment of the invention there is provided a class of compounds of formula XI wherein $R^1$ represents H;

$R^2$ represents $C_2$alkyl;

L is situated in the meta or para position and represents $(CH_2)_nOC(O)(CH_2)_i$;

n is an integer 1;

i is an integer 0;

p is 0;

A represents aryl or heteroaryl, each optionally substituted by one or more of the following independently selected from: monocyclic aryl, $NR^aC(O)OR^b$;

X is the same as for the sixth embodiment.

The invention also relates to process for the preparation of a compound of formula XI, wherein $R^1$ is hydrogen, X is oxygen, $R^2$, $R^3$, p, L, n, i, and A are as defined for formula XI, comprising deprotection a compound of formula V,

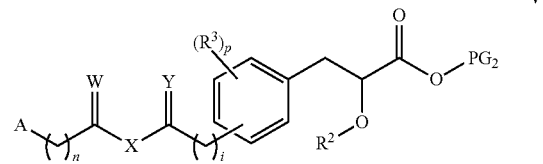

V wherein X is oxygen, Y is oxygen when W is H,H (or Y is H,H when W is oxygen) and $PG_2$ is a protecting group, such as benzyl, using a hydrogenating reagent, such as hydrogen ($H_2$) in the presence of palladium on carbon (Pd—C).

According to one embodiment $PG_2$ is benzyl and the hydrogenating reagent is hydrogen ($H_2$) in the presence of palladium on carbon (Pd—C).

According to yet another aspect of the invention there is provided a compound of general formula (CI)

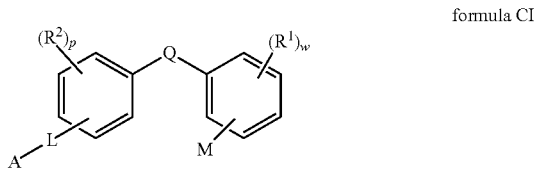

formula CI wherein $R^1$ represents F;

w is an integer 0-4;

M is situated in the ortho or meta position and represents COOH;

Q represents $C_1$-$C_2$alkylX or $XC_1$-$C_2$alkyl;

X represents S or O;

$R^2$ is situated in the ortho, meta or para position and represents F;

p is an integer 0-4;

L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C(O)OC_1$-$C_3$alkyl, heteroaryl, $C_1$-$C_3$alkyl, $C_1$-$C_2$alkoxy, which $C_1$-$C_3$alkyl or $C_1$-$C_2$alkoxy substituents is each optionally substituted with one or more F;

n is an integer 0-3;

i is an integer 0-3;

A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$ $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F);

or a pharmaceutically acceptable salt thereof

Further values of $R^1$, w, M, Q, X, $R^2$, p, L, n, i, and A in compounds of formula CI will now follow. It will be understood that such values may be used where appropriate with any of the definitions, claims or embodiments hereinbefore or hereinafter.

In an 11$^{th}$ embodiment of the invention there is provided a class of compounds of formula CI wherein $R^1$ represents F;

w is an integer 0-4;

M is situated in the ortho or meta position and represents COOH;

Q represents $C_1$-$C_2$alkylX or $XC_1$-$C_2$alkyl;

X represents S or O;

$R^2$ is situated in the ortho, meta or para position and represents F;

p is an integer 0-4;

L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C(O)OC_1$-$C_3$alkyl, heteroaryl, $C_1$-$C_3$alkyl, $C_1$-$C_2$alkoxy, which $C_1$-$C_3$alkyl or $C_1$-$C_2$alkoxy substituents is each optionally substituted with one or more F;

n is an integer 0-3;

i is an integer 0-3;

A represents aryl or heteroaryl, each optionally by one or more of the following independently selected from: halogen, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F), or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F).

In a 12$^{th}$ embodiment of the invention there is provided a class of compounds of formula CI wherein Q represents $XC_1$-$C_2$alkyl;

X represents S or O;

L is situated in the meta or para position and represents $(CH_2)_nC(O)O(CH_2)_i$, or $(CH_2)_nOC(O)(CH_2)_i$, each optionally substituted on any available carbon atom with one or more of the following substituents independently selected from: F, $C_2$-$C_3$alkenyl, $C(O)OC_1$-$C_3$alkyl, heteroaryl, $C_1$-$C_3$alkyl, $C_1$-$C_2$alkoxy, which $C_1$-$C_3$alkyl or $C_1$-$C_2$alkoxy substituents is each optionally substituted with one or more F;

$R^1$, w, M, $R^2$, p, n, i, and A are the same as for the 11$^{th}$ embodiment.

In a 13$^{th}$ embodiment of the invention there is provided a class of compounds of formula CI wherein Q represents $XC_1$-$C_2$alkyl;

X represents S or O;

L is situated in the meta or para position and represents $(CH_2)_nC(O)O(CH_2)_i$, or $(CH_2)_nOC(O)(CH_2)_i$, each optionally substituted on any available carbon atom with one or more of the following substituents independently selected from: F, $C_2$-$C_3$alkenyl, $C(O)OC_1$-$C_3$alkyl, heteroaryl, $C_1$-$C_3$alkyl, $C_1$-$C_2$alkoxy, which $C_1$-$C_3$alkyl or $C_1$-$C_2$alkoxy each optionally is substituted with one or more F;

A represents aryl optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, CN, $NR^aR^a$, $OR^b$, $SR^b$, $SiR^bR^bR^b$, $S(O)R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $OSO_2R^b$, $NO_2$, $C(O)R^b$, $C_1$-$C_4$alkyl (which is optionally substituted by one or more F);

$R^1$, w, M, $R^2$, p, n, and i are the same as for the 11$^{th}$ embodiment.

In a 14$^{th}$ embodiment of the invention there is provided a class of compounds of formula CI wherein
w is an integer 0;
M is situated in the ortho position and represents COOH;
Q represents $XC_1$alkyl;
X represents S;
p is an integer 0;
L is situated in the meta or para position and represents $(CH_2)_nC(O)O(CH_2)_i$, or $(CH_2)_nOC(O)(CH_2)_i$, each optionally substituted on any available carbon atom with one or more of the following substituents independently selected from: $C_2$-$C_3$alkenyl, $C(O)OC_1$-$C_1$alkyl, heteroaryl;
n is an integer 1-2;
i is an integer 1;
A represents aryl optionally substituted by one or more of the following independently selected from: $OR^b$, $C_1$-$C_4$alkyl (which is optionally substituted by one or more F); monocyclic heteroaryl.

In a 15$^{th}$ embodiment of the invention there is provided a class of compounds of formula CI wherein
w is an integer 0;
M is situated in the ortho position and represents COOH;
Q represents $XC_1$alkyl;
X represents S;
p is an integer 0;
L is situated in the meta or para position and represents $(CH_2)_nOC(O)(CH_2)_i$;
n is an integer 1-2;
i is an integer 1;
A represents phenyl optionally substituted by one or more of $C_1$alkyl (which is optionally substituted by one or more of F).

In a 16$^{th}$ embodiment of the invention there is provided a class of compounds of formula CI wherein
$R^1$ represents F;
w is an integer 0-4;
M is situated in the ortho or meta position and represents COOH;
Q represents $C_1$-$C_2$alkylX or $XC_1$-$C_2$alkyl;
X represents S or O;
$R^2$ is situated in the ortho, meta or para position and represents F;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C(O)OC_1$-$C_3$alkyl, heteroaryl, $C_1$-$C_3$alkyl, $C_1$-$C_2$alkoxy, which $C_1$-$C_3$alkyl or $C_1$-$C_2$alkoxy substituents is each optionally substituted with one or more F;
n is an integer 0-3;
i is an integer 0-3;
A represents aryl or heteroaryl, each optionally substituted by one halogen and/or by one or more of the following independently selected from: OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$ $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F),
or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogen, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F).

According to still another aspect of the invention there is provided a compound of formula (MI):

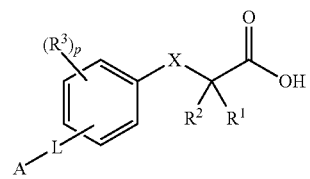

formula MI wherein
$R^1$ represents $C_1$-$C_2$alkyl optionally substituted by one or more F;
$R^2$ represents $C_1$-$C_2$alkyl optionally substituted by one or more F;
X represents O or S;
$R^3$ is situated in the ortho, meta or para position and represents F, $C_1$-$C_4$alkyl or $C_1$-$C_2$alkoxy, which $C_1$-$C_4$alkyl or $C_1$-$C_2$alkoxy substituents is each optionally substituted by one or more F;
or $R^3$ is $CH_2Ph$, or $NHC(O)OC(CH_3)_3$;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$, or $(CH_2)_nSC(O)(CH_2)_i$, each optionally substituted on any available carbon atom with one or more of the following substituents independently selected from: F, $C_2$-$C_3$alkenyl, $C_1$-$C_3$alkyl, $C_1$-$C_2$alkoxy, which $C_1$-$C_3$alkyl or $C_1$-$C_2$alkoxy each optionally is substituted with one or more F;
n is an integer 0-3;
i is an integer 0-3;
A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, OSO$_2$R$^b$, NO$_2$, C$_1$-C$_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C$_1$-C$_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, NR$^a$R$^a$, OR$^b$, SR$^b$, SiR$^b$R$^b$R$^b$, S(O)R$^b$, SO$_2$R$^b$, OSO$_2$R$^b$, NO$_2$, C(O)R$^b$, C$_1$-C$_4$alkyl (which is optionally substituted by one or more F), or A is cycloalkyl or heterocyclyl, each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, C$_1$-C$_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C$_1$-C$_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, NR$^a$R$^a$, OR$^b$, SR$^b$, SiR$^b$R$^b$R$^b$, S(O)R$^b$, SO$_2$R$^b$, OSO$_2$R$^b$, NO$_2$, C(O)R$^b$, C$_1$-C$_4$alkyl (which is optionally substituted by one or more F);

or a pharmaceutically acceptable salt thereof

Further values of R$^1$, R$^2$, X, R$^3$, p, L, n, i, and A in compounds of formula MI now will follow. It will be understood that such values may be used where appropriate with any of the definitions, claims or embodiments defined hereinbefore or hereinafter.

In a 17$^{th}$ embodiment of the invention there is provided a class of compounds of formula MI wherein R$^1$ represents C$_1$-C$_2$alkyl optionally substituted by one or more F;

R$^2$ represents C$_1$-C$_2$alkyl optionally substituted by one or more F;

X represents O or S;

R$^3$ is situated in the ortho, meta or para position and represents F, C$_1$-C$_4$alkyl or C$_1$-C$_2$alkoxy, which C$_1$-C$_4$alkyl or C$_1$-C$_2$alkoxy substituents is each optionally substituted by one or more F;

or R$^3$ is CH$_2$Ph, or NHC(O)OC(CH$_3$)$_3$;

p is an integer 0-4;

L is situated in the meta or para position and represents (CH$_2$)$_n$C(O)O(CH$_2$)$_i$, (CH$_2$)$_n$C(O)S(CH$_2$)$_i$, (CH$_2$)$_n$OC(O)(CH$_2$)$_i$, or (CH$_2$)$_n$SC(O)(CH$_2$)$_i$, each optionally substituted on any available carbon atom with one or more of the following substituents independently selected from: F, C$_2$-C$_3$alkenyl, C$_1$-C$_2$alkoxy, which C$_1$-C$_3$alkyl or C$_1$-C$_2$alkoxy each optionally is substituted with one or more F;

n is an integer 0-3;

i is an integer 0-3;

A represents aryl or heteroaryl, each optionally substituted by one or more of the following independently selected from: halogen, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, OSO$_2$R$^b$, NO$_2$, C$_1$-C$_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C$_1$-C$_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, NR$^a$R$^a$, OR$^b$, SR$^b$, SiR$^b$R$^b$R$^b$, S(O)R$^b$, SO$_2$R$^b$, OSO$_2$R$^b$, NO$_2$, C(O)R$^b$, C$_1$-C$_4$alkyl (which is optionally substituted by one or more F), or A is cycloalkyl or heterocyclyl, each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, C$_1$-C$_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, NR$^a$R$^a$, OR$^b$, SR$^b$, SiR$^b$R$^b$R$^b$, S(O)R$^b$, SO$_2$R$^b$, C(O)R$^b$, C$_1$-C$_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, NR$^a$R$^a$, OR$^b$, SR$^b$, SiR$^b$R$^b$R$^b$, S(O)R$^b$, SO$_2$R$^b$, OSO$_2$R$^b$, NO$_2$, C(O)R$^b$, C$_1$-C$_4$alkyl (which is optionally substituted by one or more F).

In a 18$^{th}$ embodiment of the invention there is provided a class of compounds of formula MI wherein R$^1$ represents C$_1$alkyl optionally substituted by one or more F;

R$^2$ represents C$_1$alkyl optionally substituted by one or more F;

X represents O;

R$^3$, p, L, n, i, and A are the same as for the 17$^{th}$ embodiment.

In a 19$^{th}$ embodiment of the invention there is provided a class of compounds of formula MI wherein R$^1$ represents C$_1$alkyl optionally substituted by one or more F;

R$^2$ represents C$_1$alkyl optionally substituted by one or more F;

X represents O;

L is situated in the meta or para position and represents (CH$_2$)$_n$OC(O)(CH$_2$)$_i$;

n is an integer 1;

i is an integer 0;

R$^3$, p and A are the same as for the 17$^{th}$ embodiment.

In a 20$^{th}$ embodiment of the invention there is provided a class of compounds of formula MI wherein R$^1$ represents C$_1$alkyl optionally substituted by one or more F;

R$^2$ represents C$_1$alkyl optionally substituted by one or more F;

X represents O;

p is an integer 0;

L is situated in the meta or para position and represents (CH$_2$)$_n$OC(O)(CH$_2$)$_i$;

n is an integer 1;

i is an integer 0;

A represents heteroaryl optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^a$-$C(O)NR^aR^a$, $OSO_2R^b$, $NO_2$, $C_1$-$C_4$alkyl (which is optionally substituted by one or more F); monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $C(O)R^b$, $C_1$-$C_4$alkyl (which is optionally substituted by one or more F); monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl (which is optionally substituted by one or more F).

The compounds of formula I, XI, CI and MI have activity as medicaments

Specific compounds of the invention are one or more of the following:

4-Methanesulfonyloxy-benzoic acid 4-{2-carboxy-2-[2-(4-fluoro-phenyl)-ethylsulfanyl]-ethyl}-benzyl ester;

2-[2-(4-Fluoro-phenyl)-ethylsulfanyl]-3-{4-[2-(4-methanesulfonyloxy-phenyl)-acetoxymethyl]-phenyl}-propionic acid;

2-[2-(4-Fluoro-phenyl)-ethylsulfanyl]-3-[4-(4-trifluoromethyl-benzyloxycarbonylmethyl)-phenyl]-propionic acid;

2-[2-(4-Fluoro-phenyl)-ethylsulfanyl]-3-[4-(4-methanesulfonyloxy-benzyloxycarbonylmethyl)-phenyl]-propionic acid;

2-[2-(4-Fluoro-phenyl)-ethylsulfanyl]-3-(4-{2-[2-(4-methanesulfonyloxy-phenyl)-acetoxy]-ethyl}-phenyl)-propionic acid;

2-[2-(4-Fluoro-phenyl)-ethylsulfanyl]-3-(4-{3-[2-(4-methanesulfonyloxy-phenyl)-acetoxy]-propyl}-phenyl)-propionic acid;

2-[2-(4-Fluoro-phenyl)-ethylsulfanyl]-3-[4-(2-phenyl-propionyloxymethyl)-phenyl]-propionic acid;

2-[2-(4-Fluoro-phenyl)-ethylsulfanyl]-3-{4-[2-(4-methoxylphenylacetoxymethyl]phenyl}-propionic acid;

2-[2-(4-Fluoro-phenyl)-ethylsulfanyl]-3-{4-[2-(4-isobutyl-phenyl)-propionyloxymethyl]-phenyl}-propionic acid;

2-[2-(4-Fluoro-phenyl)-ethylsulfanyl]-3-[4-(2-pyridin-2-yl-acetoxymethyl)-phenyl]-propionic acid;

2-[2-(4-Fluoro-phenyl)-ethylsulfanyl]-3-{4-[2-(4-methyl-piperazin-1-yl)-acetoxymethyl]-phenyl}-propionic acid;

4-{2-Carboxy-2-[2-(4-fluoro-phenyl)-ethylsulfanyl]-ethyl}-benzoic acid 2-phenyl-5 trifluoromethyl-oxazol-4-ylmethyl ester 2-Phenyl-5-trifluoromethyl-oxazole-4-carboxylic acid 4-{2-carboxy-2-[2-(4-fluoro-phenyl)-ethylsulfanyl]-ethyl}-benzyl ester;

4-{2-Carboxy-2-[2-(4-fluoro-phenyl)-ethylsulfanyl]-ethyl}-benzoic acid 2-(5-methyl-2 phenyl-oxazol-4-yl)-ethyl ester;

2-[2-(4-Fluoro-phenyl)-ethylsulfanyl]-3-{4-[2-(5-methyl-2-phenyl-oxazol-4-yl) acetoxymethyl]-phenyl}-propionic acid;

4-{2-Carboxy-2-[2-(4-fluoro-phenyl)-ethylsulfanyl]-ethyl}-benzoic acid 4-methanesulfonyloxy-benzyl ester;

2-[2-(4-Fluoro-phenyl)-ethanesulfonyl]-3-[4-(4-trifluoromethyl-benzyloxycarbonylmethyl)-phenyl]-propionic acid;

2-[2-(4-Fluoro-phenyl)-ethylsulfanyl]-3-{4-[2-(4-methanesulfonyloxy-phenyl)-ethylsulfanylcarbonyl]-phenyl}-propionic acid;

(−)-2-[2-(4-Fluoro-phenyl)-ethylsulfanyl]-3-{4-[2-(5-methyl-2-phenyl-oxazol-4-yl)-acetoxymethyl]-phenyl}-propionic acid 4-{(−)-2-Carboxy-2-[2-(4-fluoro-phenyl)-ethylsulfanyl]-ethyl}-benzoic acid 2-(5-methyl-2-phenyl-oxazol-4-yl)-ethyl ester (S)-2-Ethoxy-3-{4-[2-(5-methyl-2-phenyl-oxazol-4-yl)-acetoxy]-phenyl}-propionic acid;

(S)-3-{4-[2-(4-tert-Butoxycarbonylamino-phenyl)-acetoxy]-phenyl}-2-ethoxy-propionic acid;

3-{3-Benzyl-4-[2-(5-methyl-2-phenyl-oxazol-4-yl)-acetoxy]-phenyl}-2-ethoxy-propionic acid;

3-{3-Benzyl-4-[2-(4-tert-butoxycarbonylamino-phenyl)-acetoxy]-phenyl}-2-ethoxy-propionic acid;

2-Ethoxy-3-{3-methyl-4-[2-(5-methyl-2-phenyl-oxazol-4-yl)-acetoxy]-phenyl}-propionic acid;

3-{4-[2-(4-tert-Butoxycarbonylamino-phenyl)-acetoxy]-3-methyl-phenyl}-2-ethoxy-propionic acid;

4-(2-Carboxy-2-ethoxy-ethyl)-benzoic acid 4-methanesulfonyloxy-benzyl ester;

2-[3-(4-Trifluoromethyl-benzyloxycarbonylmethyl)-phenylsulfanylmethyl]-benzoic acid;

2-{4-[2-(4-Trifluoromethyl-phenyl)-acetoxymethyl]-phenylsulfanylmethyl}-benzoic acid;

2-[4-(4-Trifluoromethyl-benzyloxycarbonylmethyl)-phenylsulfanylmethyl]-benzoic acid;

2-{3-[1-(4-Trifluoromethyl-phenyl)-ethoxycarbonylmethyl] phenylsulfanylmethyl}-benzoic acid;

2-{3-[2-(4-Trifluoromethyl-phenyl)-ethoxycarbonylmethyl]-phenylsulfanylmethyl}-benzoic acid;

2-[4-(2,6-Dimethyl-benzyloxycarbonylmethyl)-phenylsulfanylmethyl]-benzoic acid;

2-[4-(1-Phenyl-but-3-enyloxycarbonylmethyl)-phenylsulfanylmethyl]-benzoic acid;

2-[3-(1-Methoxycarbonyl-2-phenyl-ethoxycarbonylmethyl)-phenylsulfanylmethyl]-benzoic acid;

2-{4-[2-(3,4-Dimethoxy-phenyl)-ethoxycarbonylmethyl]-phenylsulfanylmethyl}-benzoic acid;

2-[4-(1-Methoxycarbonyl-2-phenylethoxycarbonylmethyl) phenylsulfanylmethyl]-benzoic acid;

2-{3-[2-(2-Trifluoromethylphenyl)ethoxycarbonylmethyl] phenylsulfanylmethyl}-benzoic acid;

2-[4-(Oxazol-2-yl-phenyl-methoxycarbonylmethyl)-phenylsulfanylmethyl]-benzoic acid;

2-{4-[2-(2-Trifluoromethylphenyl)ethoxycarbonylmethyl] phenylsulfanylmethyl}-benzoic acid;

2-[3-(2,6-Dimethyl-benzyloxycarbonylmethyl)-phenylsulfanylmethyl]-benzoic acid;

2-[3-(4-Pyrazol-1-yl-benzyloxycarbonylmethyl)-phenylsulfanylmethyl]-benzoic acid;

2-[4-(4-Pyrazol-1-yl-benzyloxycarbonylmethyl)-phenylsulfanylmethyl]-benzoic acid;

2-{3-[2-(3,4-Dimethoxy-phenyl)-ethoxycarbonylmethyl]-phenylsulfanylmethyl}-benzoic acid;

4-(1-carboxy-1-methyl-ethoxy)-benzoic acid 4-methyl-2-(4-trifluoromethyl-phenyl)-thiazol-5-ylmethyl ester or a pharmaceutically acceptable salt thereof.

Certain compounds of the present invention may exist as tautomers or stereoisomers (e.g. racemate, enantiomer, diastereomer or E- or Z-isomer). It is to be understood that the present invention encompasses all such tautomers or stereoisomers.

Certain compounds of the present invention may exist as solvates or hydrates. It is to be understood that the present invention encompasses all such solvates or hydrates.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, nitric, methanesulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quarternery ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R,2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

In a further aspect the present invention provides the use of a compound of formulas I, XI, CI and MI as a medicament.

Methods of Preparation for Formula I

The compounds of Formula I of the invention may be prepared as outlined in the schemes I-IV below. However, the invention is not limited to these methods. The compounds may also be prepared as described for structurally related compounds in the prior art. The reactions can be carried out according to standard procedures or as described in the experimental section.

Scheme I

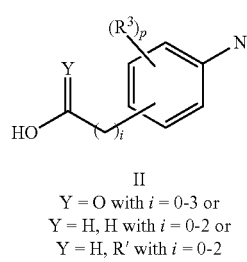

II
Y = O with i = 0-3 or
Y = H, H with i = 0-2 or
Y = H, R' with i = 0-2

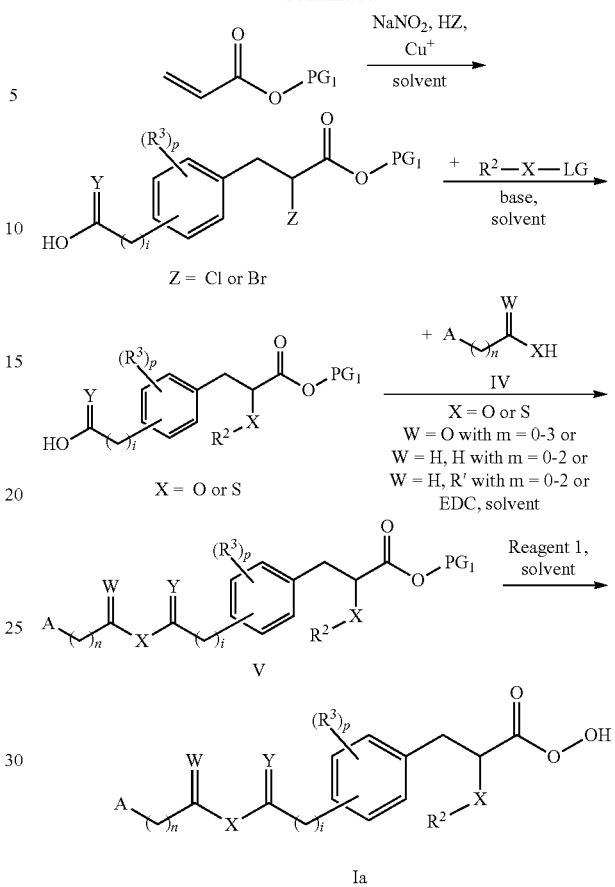

For formula Ia and V:
X = O or S
if Y = H, H with n = 0-2 then W = O with m = 0-3 or
if Y = H, R' with n = 0-2 then W = O with m = 0-3 or
if Y = O with n = 0-3 then W = H, H with m = 0-2 or
if Y = O, with n = 0-3 then W = H, R with m = 0-2

Scheme II

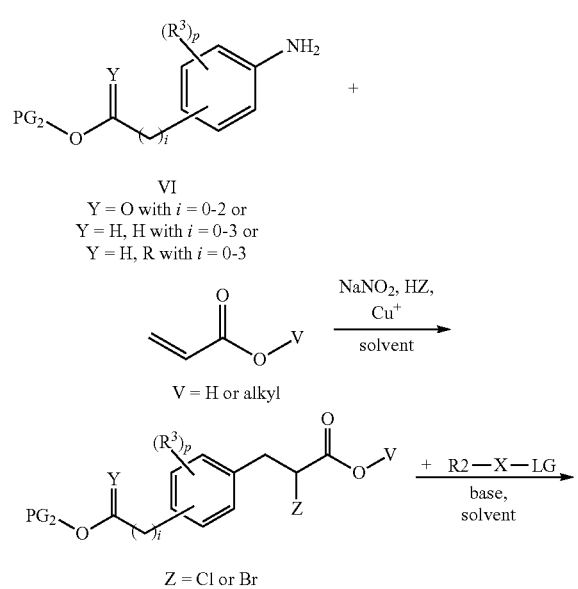

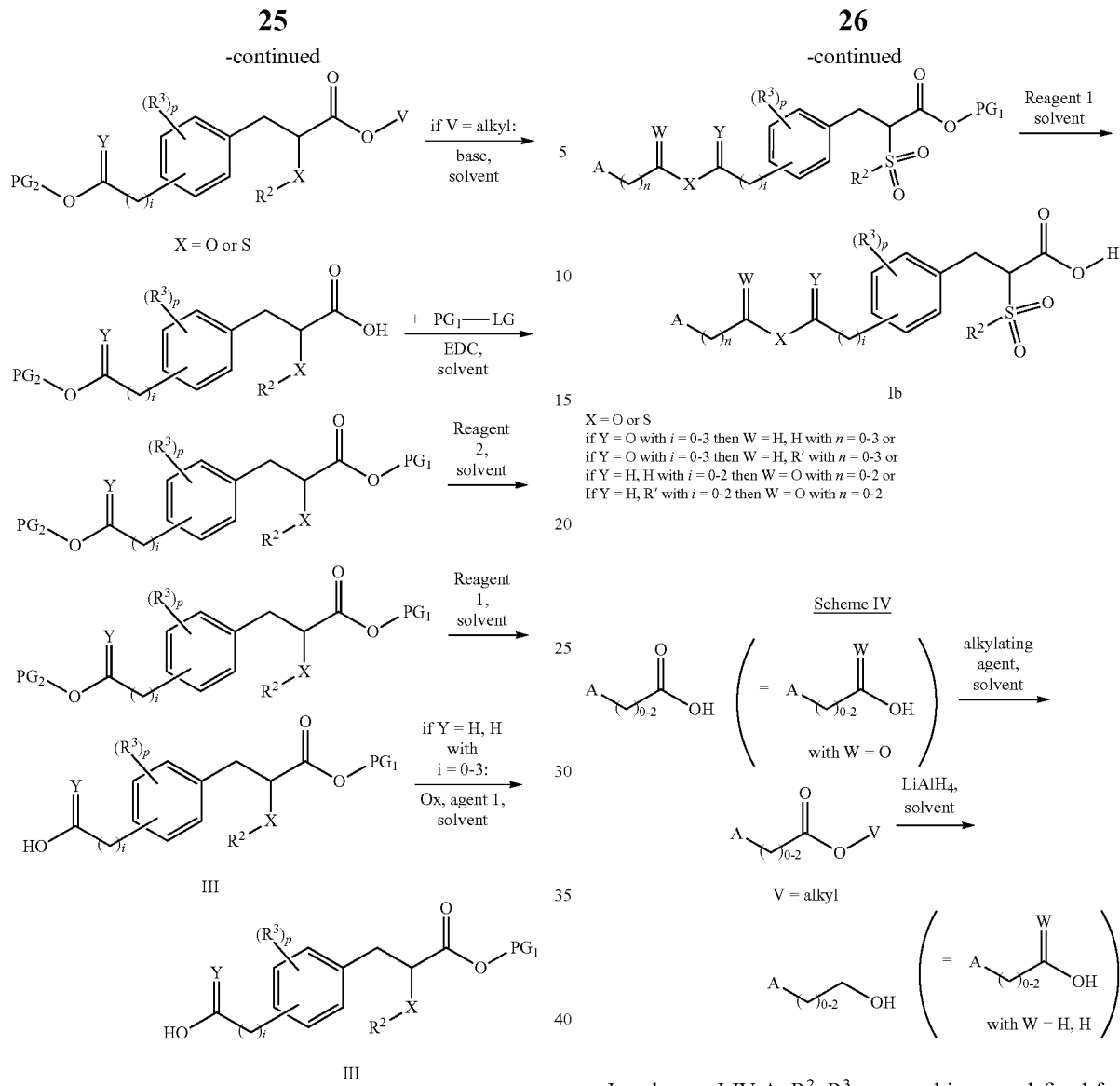

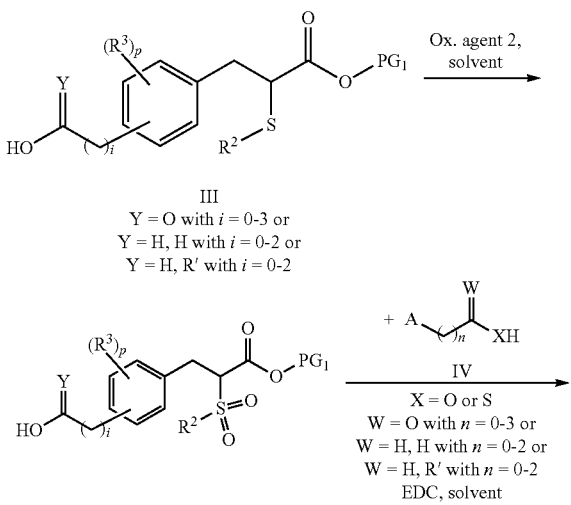

In schemes I-IV A, $R^2$, $R^3$, p. n and i are as defined for compounds of formula (I) above.

In schemes I-IV V, W, X and Y are as defined above.

In scheme I-III R' represents any substitutent which is inert to the reaction conditions used for the outlined intermediates. Such substituents are for instance alkyl groups or alkoxy groups.

In the schemes I-IV above the abbreviation "PG" means protecting group. PG1 represents a protecting group for carboxylic hydroxy groups which tolerates the required reaction conditions for the synthesis of the outlined intermediates but can be cleaved off with an appropriate deprotecting reagent. PG2 represents a protecting group for alcoholic hydroxy groups which tolerates the required reaction conditions for the synthesis of the outlined intermediates but can be cleaved off with an appropriate deprotecting reagent. Examples of such protecting groups are described in the standard text book "Protective Groups in the Organic Synthesis", 3$^{rd}$ Edition (1999) by T. W. Greene and P. G. M. Wuts.

In the schemes I-IV above the term "reagent" means a reagent that causes the selective cleavage of the protecting group. Reagent 1 represents any reagent which allows the deprotection from PG1, reagent 2 represents any reagent which allows the deprotection from PG2. Examples of such reagents are described in the standard text book "Protective Groups in the Organic Synthesis", 3$^{rd}$ Edition (1999) by T. W. Greene and P. G. M. Wuts.

In the schemes I-IV above the abbreviation "LG" means a leaving group. Examples of such leaving groups are for instance Cl, Br, I, methanesulfonate (OMs), acetate (Ac) or simply a proton (H).

In schemes II and III the term "ox. agent" means oxidation agent. Ox. agent 1 represents any reagent which allows the transfer a primary alcohol to the corresponding carboxylic acid. Examples of such reagents are for instance potassium permanganate, pyridinium dichromate or ruthenium tetraoxide. Ox. agent 2 represents any reagent which allows to transfer a thioether into the corresponding sulfone. Examples of such reagents are for instance metachloroperbenzoic acid (MCPBA) or potassium peroxymonosulfate (Oxone™).

In scheme II an alternative multistep synthesis for the intermediate of formula III is outlined.

In scheme IV the synthesis of non-commercial primary alcohols from commercially available carboxylic acids is outlined. The term "alkylating reagent" in this scheme means any reagent plus base or acid if required which transfers the carboxylic acid into the corresponding alkylester. Examples of such alkylating reagent are for instance iodomethane, methanol or trimethylsilyl diazomethane.

In the schemes I-IV above the expression "solvent" refers to a solvent which does not react with the starting materials, reagents, intermediates or products in a manner which adversely affects the yield of the desired product. Examples of such solvents are for instance dimethylformamide, methylene chloride and acetonitrile.

It shall be understood that the Cu$^+$ in schemes I and II represents any kind of Cu(I) salt, for instance Cu(I)O or Cu(I)I.

It is to be understood that 1-ethyl-3-(3-dimethylaminopropyl)carbodiimide hydrochloride (EDC) in scheme I, II and III can be exchanged for equivalent reagents.

It shall also be understood that the individual reaction steps in the schemes I-IV above may required a reaction temperature deviating from room temperature. Warming or heating may be achieved by using conventional methods such as heating the reaction mixture on an oil bath or heating the reaction mixture in a microwave oven. Cooling may be achieved by using conventional methods like cooling the reaction mixture in an ice bath or cooling with solid carbon dioxide in an appropriate solvent or by using a cryostatic temperature regulator.

It shall be understood that for the compounds of formula Ib and formula X in scheme II the atom X can be equal in the same molecule but it does not necessarily have to be. X can be only oxygen or only sulfur in the same molecule but it also can be oxygen at one place and sulfur at the other place.

The substituted aniline derivatives of formula II and VI, the acrylic acid esters, the alcohols or thiols bearing R$^2$ and the carboxylic acids, alcohols or thiols bearing A in the schemes I-IV above are commercially available or may be prepared as described in the experimental part in this patent application or by methods known by those skilled in the art.

The compounds of the invention may be isolated from their reaction mixtures using conventional techniques.

It shall be understood that enantiomerically pure or enriched compounds of formula Ia and formula Ib in schemes I-IV above can be obtained either through a racemic resolution of any of the outlined racemic intermediates or through a stereoselective synthesis where the reaction step allows.

Methods of Preparation for Formula (XI)

The compounds of Formula XI of the invention may be prepared as outlined in the scheme V below. However, the invention is not limited to these methods. The compounds may also be prepared as described for structurally related compounds in the prior art. The reactions can be carried out according to standard procedures or as described in the experimental section.

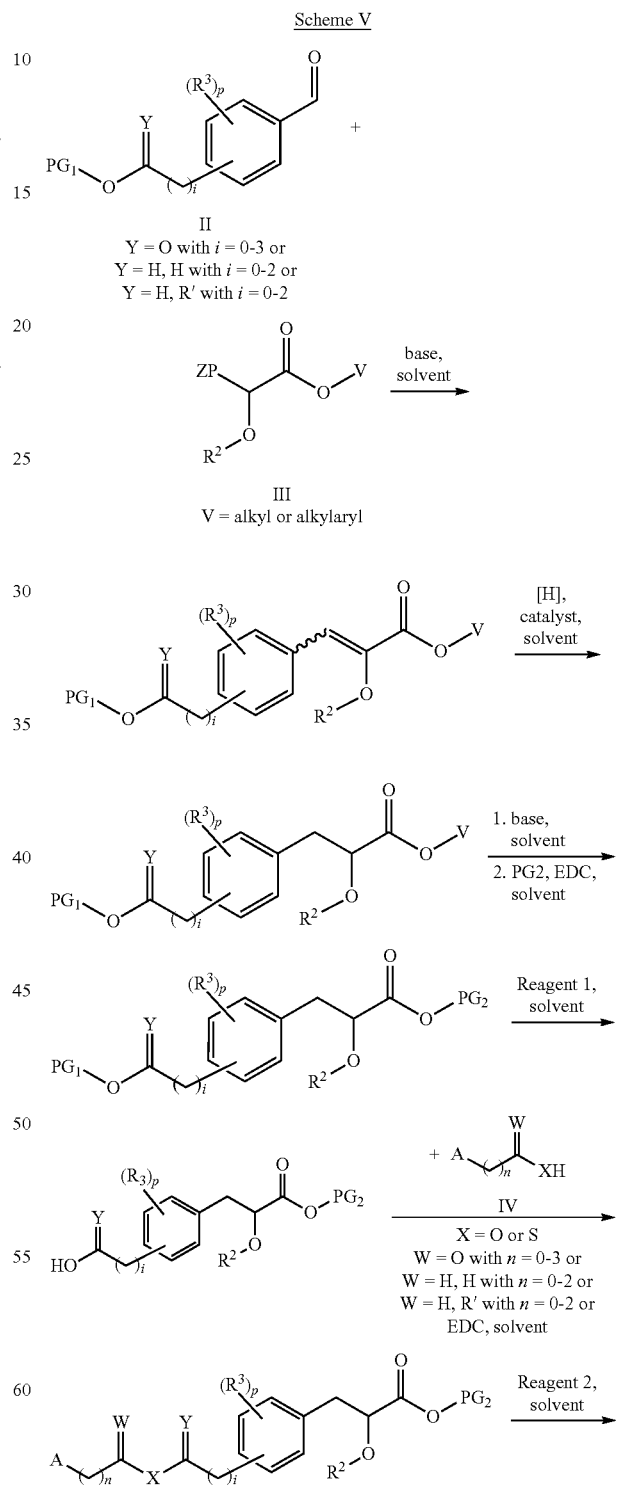

Scheme V

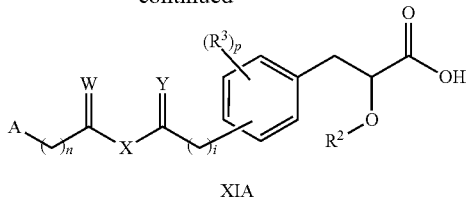

XIA

For formula XIa and V:
X = O or S
if Y = O with $i$ = 0-3 then W = H, H with $n$ = 0-3 or
if Y = O with $i$ = 0-3 then W = H, R' with $n$ = 0-2 or
if Y = H, H with $i$ = 0-3 then W = O with $n$ = 0-3 or
If Y = H, R' with $i$ = 0-2 then W = O with $n$ = 0-2

In scheme V, A, $R^2$, $R^3$, n, i and p are as defined for compounds of formula (XI) above.

In scheme V, the symbols V, W, X and Y are as defined in scheme V.

In scheme V R' represents any substitutent which is inert to the reaction conditions used for the outlined intermediates. Such substituents are for instance alkyl groups or alkoxy groups. Z in formula III refers to any substituents which can be connected to phosphorus and allow to use a compound of formula III in the outlined Wittig or Horner-Wadsworth-Emmons reaction. Examples of such substituents are for instance Z=$Ph_3$ (triphenyl) or Z=$O(OEt)_2$.

In the scheme V above the abbreviation "PG" means protecting group. PG1 and PG2 represent protecting groups for carboxylic hydroxy groups and/or alcoholic hydroxy groups which tolerate the required reaction conditions for the synthesis of the outlined intermediates but can be cleaved off selectively with an appropriate deprotecting reagent. Examples of such protecting groups are described in the standard text book "Protective Groups in the Organic Synthesis", $3^{rd}$ Edition (1999) by T. W. Greene and P. G. M. Wuts.

In the scheme V above the term "reagent" means a reagent that causes the selective cleavage of the protecting group. Reagent 1 represents any reagent which allows the selective deprotection from PG1, reagent 2 represents any reagent which allows the selective deprotection from PG2. Examples of such reagents are described in the standard text book "Protective Groups in the Organic Synthesis", $3^{rd}$ Edition (1999) by T. W. Greene and P. G. M. Wuts.

In scheme V the term "base" refers to any base which is appropriate for the outlined reaction step.

In the scheme V above the expression "solvent" refers to a solvent which does not react with the starting materials, reagents, intermediates or products in a manner which adversely affects the yield of the desired product. Examples of such solvents are for instance dimethylformamide, methylene chloride and acetonitrile.

It is to be understood that 1-ethyl-3-(3-dimethylaminopropyl)carbodiimide hydrochloride (EDC) in scheme V can be exchanged for equivalent reagents.

It shall also be understood that the individual reaction steps in the scheme V above may required a reaction temperature deviating from room temperature. Warming or heating may be achieved by using conventional methods such as heating the reaction mixture on an oil bath or heating the reaction mixture in a microwave oven. Cooling may be achieved by using conventional methods like cooling the reaction mixture in an ice bath or cooling with solid carbon dioxide in an appropriate solvent or by using a cryostatic temperature regulator.

It shall be understood that for the compounds of formula XIb and formula X in scheme V the atom X can be equal in the same molecule but it does not necessarily have to be. X can be only oxygen or only sulfur in the same molecule but it also can be oxygen at one place and sulfur at the other place.

The substituted aldehydes of formula II, the α-substituted carboxylic acid ester derivatives of formula III, the phenol or thiophenol derivatives of formula VI, the carboxylic acid derivatives of formula VII and the carboxylic acids, alcohols or thiols of formula IV in the scheme V above are commercially available or may be prepared as described in the experimental part in this patent application or by methods known to those skilled in the art.

The compounds of the invention may be isolated from their reaction mixtures using conventional techniques.

It shall be understood that enantiomerically pure or enriched compounds of formula XIa and formula XIb in scheme V above can be obtained either through a racemic resolution of any of the outlined racemic intermediates or through a stereoselective synthesis where the reaction step allows.

Methods of Preparation for Formula CI

The compounds of Formula CI of the invention may be prepared as outlined in the schemes VI and VII below. However, the invention is not limited to these methods. The compounds may also be prepared as described for structurally related compounds in the prior art. The reactions can be carried out according to standard procedures or as described in the experimental section.

Scheme VI

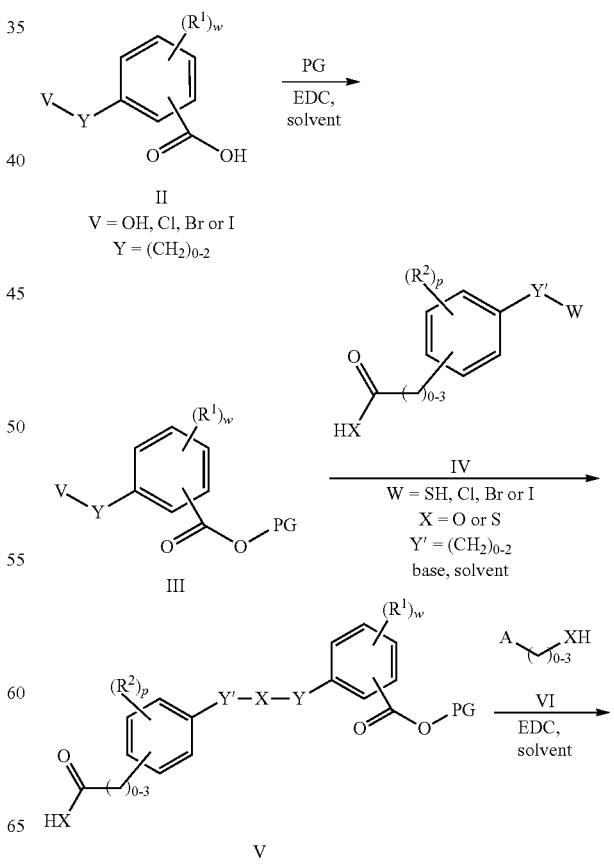

-continued

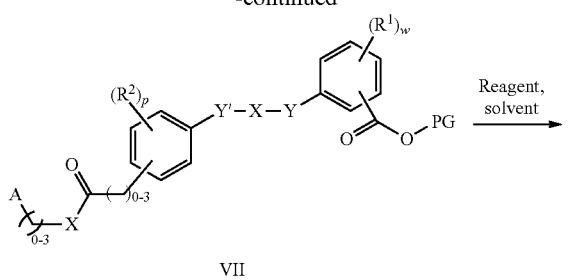

VII

CIa

For formula CIa, V and VII:
X = O or S
if Y = (CH$_2$)$_{1-2}$, then Y' = (CH$_2$)$_0$
if Y = (CH$_2$)$_0$, then Y' = (CH$_2$)$_{1-2}$ Scheme VII

V

VIII

X

CIb

X = O or S
if Y = (CH$_2$)$_{1-2}$ then Y' = (CH$_2$)$_0$
if Y = (CH$_2$)$_0$ then Y' = (CH$_2$)$_{1-2}$ In Schemes VI and VII R$^1$, R$^2$, A, w and p are as defined above for compounds of formula (CI). Furthermore, in Schemes VI and VII it shall be understood that "Y'—X—Y" corresponds to "Q" in compounds of formula (CI).

In the schemes VI and VII above the abbreviation "PG" means protecting group. PG represents a protecting group for carboxylic hydroxy groups which tolerates the required reaction conditions for the synthesis of the outlined intermediates but can be cleaved off with an appropriate deprotecting reagent. Examples of such protecting groups are described in the standard text book "Protective Groups in the Organic Synthesis", 3$^{rd}$ Edition (1999) by T. W. Greene and P. G. M. Wuts.

In the schemes VI and VII above the term "reagent" means a reagent that causes the selective cleavage of the protecting group. This reagent represents any reagent which allows the deprotection from PG. Examples of such reagents are described in the standard text book "Protective Groups in the Organic Synthesis", 3$^{rd}$ Edition (1999) by T. W. Greene and P. G. M. Wuts.

In scheme VII the term "Red. agent" means reducing agent. This reducing agent represents any reagent which allows the reduction of a carboxylic acid to a primary alcohol without reducing any other functional group. An examples of such a reagent is for instance BH$_3$×THF.

In the schemes VI and VII above the expression "solvent" refers to a solvent which does not react with the starting materials, reagents, intermediates or products in a manner which adversely affects the yield of the desired product. Examples of such solvents are for instance dimethylformamide, methylene chloride and acetonitrile.

It shall be understood in schemes VI and VII that for the compounds of formula CI, V, VII, VIII and X the atom X can be equal in the same molecule but it does not have to be. X can be only oxygen or only sulfur in the same molecule but it also can be oxygen at one place and sulfur at the other place.

It is to be understood that 1-ethyl-3-(3-dimethylaminopropyl)carbodiimide (EDC) in schemes VI and VII can be exchanged for equivalent reagents.

It shall also be understood that the individual reaction steps in the schemes VI and VII above may required a reaction temperature deviating from room temperature. Warming or heating may be achieved by using conventional methods such as heating the reaction mixture on an oil bath or heating the reaction mixture in a microwave oven. Cooling may be achieved by using conventional methods like cooling the reaction mixture in an ice bath or cooling with solid carbon dioxide in an appropriate solvent or by using a cryostatic temperature regulator.

The substituted benzoic acid derivatives of formula II, the building blocks formula IV and the building blocks of formula IX in the schemes VI and VII above are commercially available or may be prepared as described in the experimental part in this patent application or by methods known by those skilled in the art.

The compounds of the invention may be isolated from their reaction mixtures using conventional techniques.

Certain intermediates in the schemes VI and VII above are believed to be novel and are claimed herein as useful intermediates in the preparation of compounds of formula CIa and CIb.

Methods of Preparation for Formula MI

The compounds of Formula MI of the invention may be prepared as outlined in the scheme VIII below. However, the invention is not limited to this method. The compounds may also be prepared as described for structurally related compounds in the prior art. The reactions can be carried out according to standard procedures or as described in the experimental section.

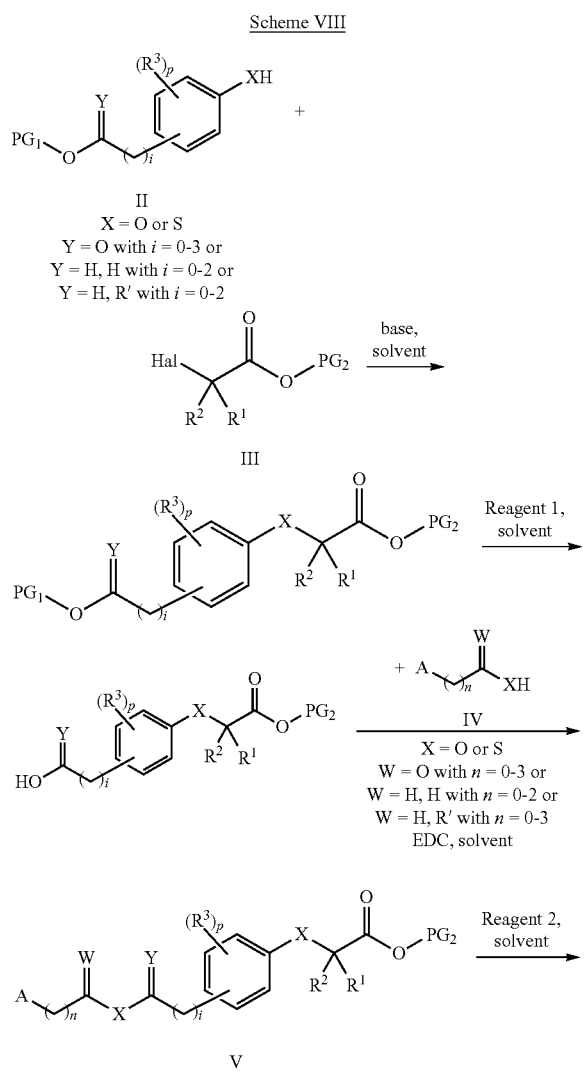

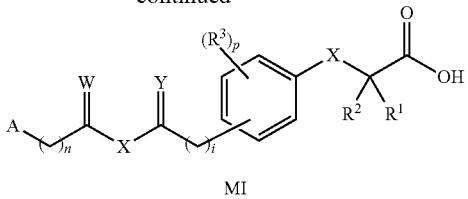

MI

For formula MI and X:
X = O or S
if Y = O, with $i$ = 0-3 then W = H, H with $n$ = 0-2 or
if Y = O, with $i$ = 0-3 then W = H, R' with $n$ = 0-2 or
if Y = H, H with $i$ = 0-2 then W = O with $n$ = 0-3 or
if Y = H, R' with $i$ = 0-2 then W = O with $n$ = 0-3

In scheme VIII $R^1$, $R^2$, X, $R^3$, p, n, i, and A are as defined for compounds of formula MI above.

In scheme VIII R' represents any substituent which is inert to the reaction conditions used for the outlined intermediates. Such substituents are for instance alkyl groups or alkoxy groups.

In the scheme VIII above the abbreviation "PG" means protecting group. PG1 and PG2 represent protecting groups for carboxylic hydroxy groups and/or alcoholic hydroxy groups which tolerate the required reaction conditions for the synthesis of the outlined intermediates but can be cleaved off selectively with an appropriate deprotecting reagent. Examples of such protecting groups are described in the standard text book "Protective Groups in the Organic Synthesis", $3^{rd}$ Edition (1999) by T. W. Greene and P. G. M. Wuts.

In the scheme VIII above the term "reagent" means a reagent that causes the selective cleavage of the protecting group. Reagent 1 represents any reagent which allows the selective deprotection from PG1, reagent 2 represents any reagent which allows the selective deprotection from PG2. Examples of such reagents are described in the standard text book "Protective Groups in the Organic Synthesis", $3^{rd}$ Edition (1999) by T. W. Greene and P. G. M. Wuts.

In scheme VIII the term "base" refers to any base which is appropriate for the outlined reaction step.

In the scheme VIII above the expression "solvent" refers to a solvent which does not react with the starting materials, reagents, intermediates or products in a manner which adversely affects the yield of the desired product. Examples of such solvents are for instance dimethylformamide, methylene chloride and acetonitrile.

It is to be understood that 1-ethyl-3-(3-dimethylaminopropyl)carbodiimide (EDC) in scheme VIII can be exchanged for equivalent reagents.

It shall also be understood that the individual reaction steps in the scheme VIII above may require a reaction temperature deviating from room temperature. Warming or heating may be achieved by using conventional methods such as heating the reaction mixture on an oil bath or heating the reaction mixture in a microwave oven. Cooling may be achieved by using conventional methods like cooling the reaction mixture in an ice bath or cooling with solid carbon dioxide in an appropriate solvent or by using a cryostatic temperature regulator.

It shall be understood that for the compounds of formula MI and formula V in scheme VIII the atom X can be equal in the same molecule but it does not necessarily have to be. X can be only oxygen or only sulfur in the same molecule but it also can be oxygen at one place and sulfur at the other place.

The phenol or thiophenol derivatives of formula II, the carboxylic acid derivatives of formula III and the carboxylic acids, alcohols or thiols of formula IV in the scheme VIII above are commercially available or may be prepared as described in the experimental part in this patent application or by methods known to those skilled in the art.

The compounds of the invention may be isolated from their reaction mixtures using conventional techniques.

It shall be understood that enantiomerically pure or enriched compounds of formula MI can be obtained either through a racemic resolution of any of the outlined racemic intermediates or through a stereoselective synthesis where the reaction step allows.

Certain intermediates in the schemes I-VIII above are believed to be novel and are claimed herein as useful intermediates in the preparation of compounds of formula I, XI, CI or MI.

Persons skilled in the art will appreciate that, in order to obtain compounds of the invention in an alternative and in some occasions, more convenient manner, the individual process steps mentioned hereinbefore may be performed in a different order, and/or the individual reactions may be performed at different stage in the overall route.

Pharmaceutical Preparations

According to one aspect of the invention there is provided a pharmaceutical formulation including any of the compounds of the invention, or pharmaceutically acceptable derivatives thereof, in admixture with pharmaceutically acceptable excipients, diluents and/or carriers.

The effect of a compound, with soft-drug properties, could also be enhanced by an appropriate pharmaceutical formulation. Such formulations can include, but are not constrained to, extended or controlled release formulations. Such formulation can also include appropriate oral, trans-dermal or rectal administrations.

Pharmacological Properties

The compounds of formula I, XI, CI and MI have activity as pharmaceuticals, in particular as modulators of PPAR activity and may be used in the prevention and/or treatment (pro-phylactic or therapeutic) of conditions/diseases in humans or animals with inflammatory responses.

The compounds of formula I, XI, CI and MI are useful for their anti-inflammatory effect on local production of cytokines and chemokines from e.g., macrophages, activated T cells, epithelial cells, repression of adhesion molecules, inhibits expression of other inflammatory markers such as reactive nitrogen derivates and COXs, induces apoptosis in a variety of cell types including T cells and macrophages, represses expression of adhesion molecules, and inhibit production of extra cellular matrix components. As a consequence of these properties, the compounds of formula I, XI, CI and MI are expected to ameliorate inflammatory bowel disorders such as Crohn's disease, ulcerative colitis, proctitis, gastric inflammation, celiac disease, appendicitis, microscopic colitis, distal proctitis, indeterminant colitis. The anti-inflammatory effect of the compound of formula I, XI, CI or MI, serves to improve the clinical signs of disease and the quality of life of the patients. The compound of formula I, XI, CI and MI are also expected to prevent or reduce the risk of clinical relapse of the disease.

The compounds of formula I, XI, CI and MI are also useful in inhibiting release of pro-inflammatory cytokines from e.g., activated macrophages, airway epithelial cells, inhibit neutrophilia, eosinophilia and the associated chemoattractants/survival factors thereof, inhibit vascular smooth muscle cell proliferation, induce apoptosis in a variety of cell types including endothelial cells, T cells and macrophages, and inhibit production of extra cellular matrix components. As an effect of these properties, the compounds of formula I, XI, CI and MI are expected to have anti-inflammatory effects in respiratory diseases such as allergic asthma, chronic obstructive pulmonary disease (COPD), acute respiratory distress syndrome (ARDS) and pulmonary fibrosis.

The compounds of formula I, XI, CI and MI are also useful in primarily inhibiting pro-inflammatory cytokine release from e.g., activated T cells and macrophages, as well as exert effect on epidermal cell growth/termination. As an effect of these properties, compounds of formula I, XI, CI and MI are expected to exert anti-inflammatory action and epidermal regulation in skin inflammatory diseases such as psoriasis, psoriatic arthritis and atopic dermatitis.

The compounds of formula I, XI, CI and MI can serves as anti-inflammatory agents by inhibiting release of pro-inflammatory cytokines, chemokines, reactive nitrogen derivates, COXs. As a consequence of these properties, compounds of formula I, XI, CI and MI are expected to exert anti-inflammatory effects in rheumatoid arthritis, if the compound can be reached by e.g. transdermal formulation.

The compounds of formula I, XI, CI and MI are also useful by inducing cell cycle arrest, as well as exert anti-inflammatory activities by inhibition of pro-inflammatory agents such as COXs, iNOS. As a consequence, compound of formula I, XI, CI and MI may exert anti-proliferative and anti-inflammatory effects in adenocarcinomas or other cancer diseases in the gastrointestinal tract (e.g., gastric cancer, colorectal cancer), respiratory tract (small lung cell cancer), skin or nasal region.

In a further aspect the present invention provides the use of a compound of formula I, XI, CI and MI in the manufacture of a medicament for the treatment and/or prophylaxis of Crohn's disease.

In a further aspect the present invention provides the use of a compound of formula I, XI, CI and MI in the manufacture of a medicament for the treatment and/or prophylaxis of ulcerative colitis.

In a further aspect the present invention provides the use of a compound of formula I, XI, CI and MI in the manufacture of a medicament for the treatment and/or prophylaxis of proctitis.

In a further aspect the present invention provides the use of a compound of formula I, XI, CI and MI in the manufacture of a medicament for the treatment and/or prophylaxis of gastric inflammation.

In a further aspect the present invention provides the use of a compound of formula I, XI, CI and MI in the manufacture of a medicament for the treatment and/or prophylaxis of celiac disease.

In a further aspect the present invention provides the use of a compound of formula I, XI, CI and MI in the manufacture of a medicament for the treatment and/or prophylaxis of appendicitis.

In a further aspect the present invention provides the use of a compound of formula I, XI, CI and MI in the manufacture of a medicament for the treatment and/or prophylaxis of microscopic colitis.

In a further aspect the present invention provides the use of a compound of formula I, XI, CI and MI in the manufacture of a medicament for the treatment and/or prophylaxis of distal proctitis.

In a further aspect the present invention provides the use of a compound of formula I, XI, CI and MI in the manufacture of a medicament for the treatment and/or prophylaxis of indeterminant colitis.

Still in a further aspect the present invention provides a method of treating and/or preventing Crohn's disease comprising the administration of an effective amount of a compound of formula I, XI, CI and MI to a mammal (particularly a human) in need thereof.

Still in a further aspect the present invention provides a method of treating and/or preventing ulcerative colitis comprising the administration of an effective amount of a compound of formula I, XI, CI and MI to a mammal (particularly a human) in need thereof.

Still in a further aspect the present invention provides a method of treating and/or preventing proctitis comprising the administration of an effective amount of a compound of formula I, XI, CI and MI to a mammal (particularly a human) in need thereof.

Still in a further aspect the present invention provides a method of treating and/or preventing gastric inflammation comprising the administration of an effective amount of a compound of formula I, XI, CI and MI to a mammal (particularly a human) in need thereof.

Still in a further aspect the present invention provides a method of treating and/or preventing celiac disease comprising the administration of an effective amount of a compound of formula I, XI, CI and MI to a mammal (particularly a human) in need thereof.

Still in a further aspect the present invention provides a method of treating and/or preventing appendicitis comprising the administration of an effective amount of a compound of formula I, XI, CI and MI to a mammal (particularly a human) in need thereof.

Still in a further aspect the present invention provides a method of treating and/or preventing microscopic colitis comprising the administration of an effective amount of a compound of formula I, XI, CI and MI to a mammal (particularly a human) in need thereof.

Still in a further aspect the present invention provides a method of treating and/or preventing distal proctitis comprising the administration of an effective amount of a compound of formula I, XI, CI and MI to a mammal (particularly a human) in need thereof.

Still in a further aspect the present invention provides a method of treating and/or preventing indeterminant colitis comprising the administration of an effective amount of a compound of formula I, XI, CI and MI to a mammal (particularly a human) in need thereof.

Combination Therapy

The compounds, or a pharmaceutically acceptable salt or solvate thereof, or a solvate of such a salt, of this invention, may be combined with other anti-inflammatory or immunosuppressant therapeutic compounds, therapeutic regimens, compositions, and agents suitable for the treatment of disorders, such that improved effects are reached and/or side effects ameliorated side effects.

Thus, the invention includes combination therapies wherein the compounds, or a pharmaceutically acceptable salt or solvate thereof, or a solvate of such a salt, of this invention are used in conjunction with other therapeutic agents used for the treatment of disorders such as inflammatory bowel disorders (IBD) such as Crohn's disease, ulcerative colitis, proctitis, gastric inflammation, celiac disease, appendicitis, microscopic colitis, distal proctitis, indeterminant colitis, allergic asthma, chronic obstructive pulmonary disease (COPD), acute respiratory distress syndrome (ARDS), pulmonary fibrosis, psoriasis, psoriatic arthritis, atopi cermatitis, rheumatoid arthritis or adenocarcinomas or other cancer disease in gastrointestinal, respiratory tract, skin or nasal region In this aspect of the present invention, the compounds of formula I, XI, CI and MI, or a pharmaceutically acceptable salt or solvate thereof, or a solvate of such a salt, may be administered in association with a GCR active compound e.g. Budesonide, Fluticazone or Prednisolone.

In another aspect of the present invention, the compounds of formula I, XI, CI and MI, or a pharmaceutically acceptable salt or solvate thereof, or a solvate of such a salt, may be administered in association with a 5-ASA compound or an appropriate NSAID. A suitable 5-ASA compound is for example Mesalazine.

In another aspect of the present invention, the compounds of formula I, XI, CI and MI or a pharmaceutically acceptable salt or solvate thereof, or a solvate of such a salt, may be administered in association with an antibiotics eg. Metronidazole, trimethoprim/sulfamthoxazole, ciprofloxacin, and tetracycline.

In another aspect of the present invention, the compounds of formula I, XI, CI and MI or a pharmaceutically acceptable salt or solvate thereof, or a solvate of such a salt, may be administered in association with anti-inflammatory antibodies acting against eg. tumor necrosis factor (TNF) eg. Infliximab.

In another aspect of the present invention, the compounds of formula I, XI, CI and MI or a pharmaceutically acceptable salt or solvate thereof, or a solvate of such a salt, may be administered in association with a dihydrofolate reductase inhibitor.

EXAMPLES

The naming of the compounds in this patent application was made using the function AutoNom within ISIS Draw Version 2.4.

Abbreviations
DCM dichloromethane
DMAP 4-dimethylaminopyridine or N,N'-dimethylaminopyridine
DMF N,N'-dimethylformamide
DMSO dimethylsulfoxide
EDC×HCl 1-ethyl-3-(3-dimethylaminopropyl)carbodiimide hydrochloride
EDC 1-ethyl-3-(3-dimethylaminopropyl)carbodiimide hydrochloride
EtOAc ethyl acetate
EtOH ethanol
HOAt 1-Hydroxy-7-azabenzotriazole
HPFC high performance flash chromatography
GP general procedure
HOAc acetic acid
HPLC high performance liquid chromatography
LC-MS liquid chromatography mass spectroscopy
$LiAlH_4$ lithium aluminium hydride
MeCN acetonitrile
MeOH methanol
NMR nuclear magnetic resonance
iPrOH 2-propanol
$iPr_2O$ Diisopropylether
TBTU O-(Benzotriazol-1-yl)-N,N,N,N-tetramethyluronium tetrafluoroborate
TEA triethylamine
TFA trifluoroacetic acid
THF tetrahydrofuran
atm atmosphere
UV ultra violet
rt room temperature
h hour(s)
min minutes
br broad s singlet
d doublet
t triplet
q quartet
m multiplet
dd double doublet

General Experimental Procedures Regarding Examples 1-20

Phase Separator from IST was used. Flash column chromatography employed normal phase silica gel 60 (0.040-0.063 mm, Merck) or IST Isolute®SPE columns normal phase silica gel or Biotage Horizon™ HPFC System using silica FLASH+™ HPFC™ Cartridges. HPLC purifications were performed on either a Gilson preparative HPLC system with a UV triggered fraction collector, equipped with an ACE C8 5 µm 250 mm×20 mm column, or a Kromasil C18 column, or on a Waters preparative HPLC system equipped with a Kromasil C8 10 µm 250 mm×21.2 mm column, or on a Waters preparative HPLC system equipped with an ACE C8 5 µm 250 mm×50 mm column or an ACE C8 5 µm 250 mm×20 mm column, or on a Waters FractionLynx HPLC system with a mass triggered fraction collector, equipped with a ACE C8 5 nm 100 mm×21.2 mm column; or a Sunfire C18 5µ 19 mm×100 mm column using MeCN/$NH_4$OAc buffer system with a gradient from 100% mobilphase A (5% MeCN+95% 0.1 M $NH_4$OAc) to 100% mobilphase B (100% MeCN) unless otherwise stated. $^1$H NMR and $^{13}$C NMR measurements were performed on a BRUKER ACP 300 or on a Varian Unity Plus 400, 500 or 600 spectrometer, operating at $^1$H frequencies of 300, 400, 500, 600 MHz, respectively, and $^{13}$C frequencies of 75, 100, 125 and 150 MHz, respectively. Chemical shifts are given in δ values (ppm) with the solvents used as internal standard, unless otherwise stated. Mass spectral data were obtained using a Micromass LCT or Waters Q-Tof micro system and, where appropriate, either positive ion data or negative ion data were collected. Microwave heating was performed using single node heating in a Smith Creator or Emrys Optimizer from Personal Chemistry, Uppsala, Sweden. The optical rotation was measured on a Perkin Elmer polarimeter Model 341.

General Experimental Procedures Regarding Examples 21-27

Phase Separator from IST was used. Flash column chromatography employed normal phase silica gel 60 (0.040-0.063 mm, Merck) or IST Isolute®SPE columns normal phase silica gel or Biotage Horizon™ HPFC System using silica FLASH+™ HPFC™ Cartridges. HPLC purifications were performed on either a Gilson preparative HPLC system with a UV triggered fraction collector, equipped with an ACE C8 5 µm 250 mm×20 mm column, or a Kromasil C18 column, or on a Waters preparative HPLC system equipped with a Kromasil C8 10 µm 250 mm×21.2 mm column, or on a Waters preparative HPLC system equipped with an ACE C8 5 µm 250 mm×50 mm column or an ACE C8 5 µm 250 mm×20 mm column, or on a Waters FractionLynx HPLC system with a mass triggered fraction collector, equipped with a ACE C8 5 µm 100 mm×21.2 mm column; or a Sunfire C18 5µ 19 mm×100 mm column using MeCN/$NH_4$OAc buffer system with a gradient from 100% mobilphase A (5% MeCN+95% 0.1 M $NH_4$OAc) to 100% mobilphase B (100% MeCN) unless otherwise stated. $^1$H NMR and $^{13}$C NMR measurements were performed on a BRUKER ACP 300 or on a Varian Unity Plus 400, 500 or 600 spectrometer, operating at $^1$H frequencies of 300, 400, 500, 600 MHz, respectively, and $^{13}$C frequencies of 75, 100, 125 and 150 MHz, respectively. Chemical shifts are given in δ values (ppm) with the solvents used as internal standard, unless otherwise stated. Mass spectral data were obtained using a Micromass LCT or Waters Q-Tof micro system and, where appropriate, either positive ion data or negative ion data were collected. Microwave heating was performed using single node heating in a Smith Creator or Emrys Optimizer from Personal Chemistry, Uppsala, Sweden.

General Experimental Procedures Regarding Examples 28-44

Phase Separator from IST was used. Flash chromatography was performed using standard glass columns employing normal phase silica gel 60 (0.040-0.063 mm, Merck). HPLC purifications were performed on Waters FractionLynx HPLC system with a mass triggered fraction collector, a Sunfire C18 5 µm 19 mm×150 mm column using MeCN/$HCO_2$H buffer system with a gradient from 100% mobilphase A (5% MeCN+95% 0.1 M $HCO_2$H, pH3) to 100% mobilphase B (100% MeCN). $^1$H NMR measurements were performed on a Varian Inova 400 and 600 spectrometer, operating at $^1$H frequencies of 400 and 600 MHz. Chemical shifts are given in δ values (ppm) with the solvent used as internal standard. Explanation for plate-NMR: The solutions are taken from a concentrated sample dissolved in $(CH_3)_2SO$ and are diluted with $(CD_3)_2 50$. Since a substantial amount of $(CH_3)_2SO$ is present in the sample, first a pre-scan is run and analysed to automatically suppress the $(CH_3)_2SO$ (2.54 ppm) and $H_2O$ (3.3 ppm) peaks. This means that in this so-called wetID experiment the intensity of peaks that reside in these areas around 3.3 ppm and 2.54 ppm are reduced. Furthermore impurities are seen in the spectrum which give rise to a triplet at 1.12 ppm, a singlet at 2.96 ppm and two multiplets between 2.76-2.70 ppm and 2.61-2.55 ppm. Mass spectral data were obtained using a Micromass LCT or Waters Q-Tof micro system and, where appropriate, either positive ion data or negative ion data were collected.

General Experimental Procedures Regarding Example 45

Phase Separator from IST was used. Flash column chromatography employed normal phase silica gel 60 (0.040-0.063 mm, Merck) or IST Isolute®SPE columns normal phase silica gel or Biotage Horizon™ HPFC System using silica FLASH+™ HPFC™ Cartridges. HPLC purifications were performed on either a Gilson preparative HPLC system with a UV triggered fraction collector, equipped with an ACE C8 5 µm 250 mm×20 mm column, or a Kromasil C18 column, or on a Waters preparative HPLC system equipped with a Kromasil C8 10 µm 250 mm×21.2 mm column, or on a Waters preparative HPLC system equipped with an ACE C8 5 µm 250 mm×50 mm column or an ACE C8 5 µm 250 mm×20 mm column, or on a Waters FractionLynx HPLC system with a mass triggered fraction collector, equipped with a ACE C8 5 µm 100 mm×21.2 mm column; or a Sunfire C18 5µ 19 mm×100 mm column using MeCN/$NH_4$OAc buffer system with a gradient from 100% mobilphase A (5% MeCN+95% 0.1 M $NH_4$OAc) to 100% mobilphase B (100% MeCN) unless otherwise stated. $^1$H NMR and $^{13}$C NMR measurements were performed on a BRUKER ACP 300 or on a Varian Unity Plus 400, 500 or 600 spectrometer, operating at $^1$H frequencies of 300, 400, 500, 600 MHz, respectively, and $^{13}$C frequencies of 75, 100, 125 and 150 MHz, respectively. Chemical shifts are given in δ values (ppm) with the solvents used as internal standard, unless otherwise stated. Mass spectral data were obtained using a Micromass LCT or Waters Q-Tof micro system and, where appropriate, either positive ion data or negative ion data were collected. Microwave heating was performed using single node heating in a Smith Creator or Emrys Optimizer from Personal Chemistry, Uppsala, Sweden.

Synthesis of Starting Materials and Intermediates Regarding Examples 1-20

(5-Methyl-2-phenyl-oxazol-4-yl)-acetic acid

The title compound is commercially available.

2-(5-Methyl-2-phenyl-oxazol-4-yl)-ethanol

The title compound is commercially available.

2-Phenyl-5-trifluoromethyl-oxazole-4-carboxylic acid

The title compound is commercially available.

2-Phenyl-propionic acid

The title compound is commercially available.

(4-Methoxy-phenyl)-acetic acid

The title compound is commercially available.

2-(4-Isobutyl-phenyl)-propionic acid

The title compound is commercially available.

Pyridin-2-yl-acetic acid

The title compound is commercially available.

(4-Methyl-piperazin-1-yl)-acetic acid

The title compound is commercially available.

(4-Methanesulfonyloxy-phenyl)-acetic acid methyl ester

The title compound was prepared as described in the following reference:
Organic Letters 2006, 8(5), 987-990.

Methanesulfonic acid 2-(4-fluoro-phenyl)-ethyl ester

The title compound was prepared as described in the following reference:
US2005/0261341A1

Thioacetic acid S-[2-(4-fluoro-phenyl)-ethyl]ester

The title compound was prepared as described in the following reference:
WO03/051826A1

Methanesulfonic acid 4-(2-methanesulfonyloxy-ethyl)-phenyl ester

The title compound was prepared as described in the following reference: WO2001040169.

(2-Phenyl-5-trifluoromethyl-oxazol-4-yl)-methanol

Under nitrogen atmosphere 2-phenyl-5-trifluoromethyl-oxazole-4-carboxylic acid (288 mg, 1.12 mmol) was dissolved in a 4:1 mixture of dry DCM and MeOH (12.5 mL) and trimethylsilyl diazomethane (134 mg, 1.176 mmol; 2.0M solution in n-hexane) was added dropwise. After 10 min. stirring at room temperature excess trimethylsilyl diazomethane was destroyed by the addition of a few drops acetic acid. The solvent was evaporated to afford the crude methylester as a yellow solid which was redissolved in dry THF and nitrogen atmosphere. LiAlH$_4$ (50 mg, 1.34 mmol) was added in several small portions and the resulting mixture was stirred at room temperature for 1.5 h. The mixture was cooled down to 0° C. and excess LiAlH$_4$ was hydrolyzed by adding MeOH (5 mL), H$_2$O (10 mL) and 2N aq. HCl (5 mL). After extracting with DCM the combined organic layers were dried (MgSO$_4$) and evaporated under reduced pressure to afford the title compound as an oil. $^1$H NMR (400 MHz, CDCl$_3$): δ 8.05-8.09 (d, 2H), 7.43-7.58 (m, 3H), 4.75 (s, 2H).

2-(4-Fluoro-phenyl)-ethanethiol

Thioacetic acid S-[2-(4-fluoro-phenyl)-ethyl]ester (9.9 g, 50 mmol) was dissolved in anhydrous THF (300 mL) and LiAlH$_4$ (7.5 g, 200 mmol) was added in several small portions. After the addition was completed the mixture was stirred for 2 h at room temperature then cooled down to 0° C. and excess LiAlH$_4$ was hydrolyzed by the addition of H$_2$O (10 mL) and aq. HCl (2N, 200 mL). The resulting clear solution was extracted with EtOAc (3×200 mL) and the combined organic layers were dried (MgSO$_4$) and evaporated under reduced pressure. The unpleasant smelling crude product (8.17 g, 104%) was carried on into the next step as obtained. $^1$H NMR (400 MHz, CDCl$_3$): δ 7.17 (dd, 2H), 7.02 (t, 2H), 2.89 (t, 2H), 2.78 (dd, 2H), 1.38 (t, 1H).

Thioacetic acid S-[2-(4-methanesulfonyloxy-phenyl)-ethyl]ester

Thioacetic acid (0.28 g, 3.73 mmol) was dissolved in anhydrous MeOH (3 mL) and Cs$_2$CO$_3$ (1.10 g, 3.39 mmol) was added. After 15 min. stirring at room temperature the MeOH evaporated under reduced pressure and the remaining oil was redissolved in anhydrous DMF (3 ml). Methanesulfonic acid 4-(2-methanesulfonyloxy-ethyl)-phenyl ester (1.00 g, 3.39 mmol), dissolved in anhydrous DMF (2 mL) was added dropwise and the reaction was stirred at room temperature for 4 h. Additional thioacetic acid (0.14 g, 1.86 mmol) was added to the reaction mixture. After 30 min. stirring, the mixture was partioned between EtOAc and brine. The separated organic layer was dried (Na$_2$SO$_4$) and finally concentration under reduced pressure. The crude material was purified by flash chromatography on silica gel 60 using n-heptan/EtOAc 7:3 as the eluent to afford the title compound as an oil. $^1$H NMR (400 MHz, CDCl$_3$): δ 7.17-7.25 (m, 4H), 3.10 (s, 3H), 3.05-3.08 (t, 2H), 2.83-2.86 (t, 2H), 2.30 (s, 3H).

Methanesulfonic acid 4-(2-mercapto-ethyl)-phenyl ester

Thioacetic acid S-[2-(4-methanesulfonyloxy-phenyl)-ethyl]ester (250 mg, 0.91 mmol) was dissolved in anhydrous THF (2.5 mL) and LiAlH$_4$ (38 mg, 1.0 mmol) was added in portions. After completed addition the mixture was warmed up to 50° C. and stirred for 1.5 h. The mixture was cooled down to 0° C. and excess LiAlH$_4$ was hydrolyzed by the addition of H$_2$O (0.8 mL), 2N aq. NaOH (1.0 mL) and THF (10 mL). Afterwards the reaction mixture was refluxed for 30 min then the precipitated salts were filtered off and the remaining filtrated was diluted with EtOAc. After extraction with brine and drying over Na$_2$SO$_4$, the solvent was evaporated under reduced pressure to afford the crude product as an oil (232 mg, 94.9%). $^1$H NMR (400 MHz, CDCl$_3$): δ 7.29-7.31 (d, 2H), 7.21-7.23 (d, 2H), 3.31 (s, 3H), 2.81-2.85 (m, 2H), 2.68-2.73 (m, 2H).

4-Methanesulfonyloxy-benzoic acid methyl ester

4-Hydroxybenzoic acid methylester (2.29 g, 20 mmol) was dissolved together with pyridine (2.02 mL, 25 mmol) in anhydrous THF (20 mL) and after cooling down to 0° C., methanesulfonyl chloride (2.16 mL, 21 mmol) was added dropwise. After complete addition the ice bath was removed and the mixture was stirred at room temperature for 5 h. The slurry was diluted with DCM and extracted with H$_2$O and aq. HCl (2N). The separated organic layer was finally dried (MgSO$_4$) and evaporated to afford the crude product as an oil (4.38 g, 95%). $^1$H NMR (400 MHz, CDCl$_3$): δ 8.07-8.09 (d, 2H), 7.32-7.34 (d, 2H), 3.90 (s, 3H), 3.16 (s, 3H).

Methanesulfonic acid 4-hydroxymethyl-phenyl ester

4-Methanesulfonyloxy-benzoic acid methyl ester (330 mg, 1.43 mmol) was dissolved in anhydrous THF (10 mL) and LiAlH$_4$ (109 mg, 2.86 mmol) was added. The resulting suspension was stirred at room temperature until no starting material was left. Excess LiAlH$_4$ was hydrolyzed with aq. HCl (2N) and the remaining suspension was extracted with EtOAc. The organic layer was separated, dried (MgSO$_4$) and evaporated and the remaining crude product was purified by flash chromatography using n-heptane/EtOAc 3:7 as the eluent to afford the title compound as an oil (202 mg, 93%). $^1$H NMR (400 MHz, CDCl$_3$): δ 7.37-7.40 (d, 2H), 7.23-7.25 (d, 2H), 4.67 (s br, 2H), 3.10 (s, 3H).

(4-Methanesulfonyloxy-phenyl)-acetic acid (4-Methanesulfonyloxy-phenyl)-acetic acid methyl ester (615 mg, 2.51 mmol) was dissolved in a 1:1 mixture of dioxane and water (6 mL) and an aq. solution of LiOH (2 eq., 5.05 mL, 1N) was added and the mixture was stirred at ambient temperature for 15 min. After the addition of aq. HCl (3N) and EtOAc, the phases were separated and the organic layer was dried (MgSO$_4$), filtered and evaporated under reduced pressure. The title compound was obtained without further purification as a solid (497 mg, 85.7%). $^1$H NMR (400 MHz, CDCl$_3$): δ 7.35-7.38 (d, 2H), 7.25-7.29 (d, 2H), 3.64 (s, 2H), 3.19 (s, 3H).

2-Chloro-3-(4-hydroxymethyl-phenyl)-propionic acid methyl ester

To a solution of the (4-amino phenyl) methanol (18.47 g, 0.15 mol) in acetone (400 mL) and methanol (200 mL) was added conc. HCl (54.69 g, 1.5 mol) followed by the dropwise addition of an aqueous solution of NaNO$_2$ (11.38 g, 0.165 mol) in water (50 mL) under ice bath cooling. The mixture was stirred for 1 h at 0° C. The ice bath was removed and the methyl acrylate (64.56 g, 0.75 mol) was added followed by CuI (4.28 g, 0.022 mol). After being stirred for 6 h at ambient temperature, the mixture was diluted with sat. aq. NaHCO$_3$ solution and extracted with EtOAc. The combined organic layers were dried (MgSO$_4$) and the solvent was subsequently evaporated under reduced. The remaining crude product was purified by chromatography. The crude product was purified by flash chromatography using DCM/MeOH 95:5 as the eluent to afford the product was obtained as an oil (13.8 g, 32%). $^1$H NMR (400 MHz, CDCl$_3$): δ 7.24 (d, 2H), 7.19 (d, 2H), 4.59-4.63 (m, 2H), 4.42 (t, 1H), 3.72 (s, 3H), 3.36-3.31 (dd, 1H), 3.17-3.12 (dd, 1H), 1.87 (s, 1H).

2-Chloro-3-[4-(2-hydroxy-ethyl)-phenyl]-propionic acid 2,2,2-trichloro-ethyl ester The title compound was prepared from 2-(4-amino phenyl) ethanol (6.68 g, 48.7 mmol) and commercially available acrylic acid 2,2,2-trichloroethylester (19.82 g, 97.44 mmol) in the same manner as described for 2-chloro-3-(4-hydroxymethyl-phenyl)-propionic acid methyl ester. The crude product was purified by repeated flash chromatography using DCM/MeOH 95:5 as the eluent and the product was obtained as an oil (1.87 g, 10.7%). $^1$H NMR (300 MHz, CDCl$_3$): δ 7.15-7.29 (m, 4H), 4.54-4.59 (t, 1H), 3.82-3.85 (m, 3H), 3.38-3.45 (dd, 1H), 3.18-3.25 (dd, 1H), 2.79-2.87 (m, 3H).

2-Chloro-3-[4-(3-hydroxy-propyl)-phenyl]-propionic acid 2,2,2-trichloro-ethyl ester The title compound was prepared from 3-(4-amino phenyl)-propan-1-ol (1.02 g, 6.72 mmol) and acrylic acid 2,2,2-trichloroethylester (4.55 g, 22.17 mmol) in the same manner as described for 2-chloro-3-(4-hydroxymethyl-phenyl)-propionic acid methyl ester. The crude product was purified by flash chromatography using DCM/iPrOH 95:5 as the eluent and the product was obtained as an oil (0.74 g, 29.4%). $^1$H NMR (300 MHz, CDCl$_3$): δ 7.08-7.30 (m, 4H), 4.56-4.60 (t, 1H), 3.63-3.65 (m, 3H), 3.35-3.43 (dd, 1H), 3.18-3.25 (dd, 1H), 2.63-2.68 (m, 3H), 1.84-1.86 (m, 2H).

3-(4-Carboxymethyl-phenyl)-2-chloro-propionic acid 2,2,2-trichloro-ethyl ester

The title compound was prepared from 2-(4-amino phenyl)-acetic acid (1.00 g, 6.61 mmol) and acrylic acid 2,2,2-trichloroethyl ester (6.73 g, 33.08 mmol) as described for 2-chloro-3-(4-hydroxymethyl-phenyl)-propionic acid methyl ester. The crude product was purified by flash chromatography using DCM/MeOH 95:5 as the eluent to afford the product as an oil (1.17 g, 47.3%). $^1$H NMR (300 MHz, CDCl$_3$): δ 7.17-7.33 (m, 4H), 4.73 (s, 2H), 4.52-4.56 (t, 1H), 3.60-3.63 (m, 2H), 3.37-3.42 (dd, 1H), 3.17-3.23 (dd, 1H).

3-[4-(tert-Butyl-dimethyl-silanyloxymethyl)-phenyl]-2-chloro-propionic acid methyl ester 2-Chloro-3-(4-hydroxymethyl-phenyl)-propionic acid methyl ester (10.6 g, 46.5 mmol) was dissolved together with imidazole (3.8 g, 55.8 mmol) in anhydrous DCM (200 mL) and tert-butyl-dimethylsilyl chloride (7.0 g, 46.5 mmol) was added in several portions at 0° C. After complete addition the cooling bath was removed and stirring was continued at ambient temperature for 17 h. The mixture was diluted with water (100 mL) and aq. HCl (50 mL, 2N) and extracted. After repeated washing with water (100 mL) the organic layer was dried (MgSO$_4$) and evaporated under reduced pressure to afford the crude product as an oil (15.8 g, 84%). $^1$H NMR (400 MHz, CDCl$_3$): δ 7.17 (d, 2H), 7.08 (d, 2H), 4.63 (s, 2H), 4.34 (t, 1H), 3.64 (s, 3H), 3.27 (dd, 1H), 3.07 (dd, 1H), 0.84 (s, 9H), 0.00 (s, 6H).

3-[4-(tert-Butyl-dimethyl-silanyloxymethyl)-phenyl]-2-[2-(4-fluoro-phenyl)-ethylsulfanyl]-propionic acid methyl ester To a solution of 3-[4-(tert-butyl-dimethyl-silanyloxymethyl)-phenyl]-2-chloro-propionic acid methyl ester (6.56 g, 42 mmol) in anhydrous DMF (200 mL) was added $Cs_2CO_3$ (14.34 g, 44 mmol) at 0° C. After stirring for 30 min 2-(4-fluoro-phenyl)-ethanethiol (13.72 g, 40 mmol), dissolved in anhydrous DMF (100 mL), was added dropwise and the resulting organe mixture was stirred for 18 h without removing the cooling bath. The mixture was diluted with $Et_2O$ and extracted with three times with $H_2O$. The organic phase was concentrated under reduced pressure and the residue was dissolved in $Et_2O$ again and repeatedly extracted with $H_2O$. After drying the separated organic layer over $MgSO_4$, the solvent was removed under reduced pressure to afford the crude product as an orange oil which was purified by chromatography using n-heptane/EtOAc 20:1 as the eluent. The desired product was obtained as an oil (4.93 g, 25.4%). $^1$H NMR (400 MHz, $CDCl_3$): δ 7.16 (d, 2H), 7.06-6.99 (m, 4H), 6.88 (t, 2H), 4.62 (s, 2H), 3.58 (s, 3H), 3.41 (dd, 1H), 3.10 (dd, 1H), 2.82 (dd, 1H), 2.74-2.76 (m, 4H), 0.85 (s, 9H), 0.00 (s, 6H).

3-[4-(tert-Butyl-dimethyl-silanyloxymethyl)-phenyl]-2-[2-(4-fluoro-phenyl)-ethylsulfanyl]-propionic acid 3-[4-(tert-Butyl-dimethyl-silanyloxymethyl)-phenyl]-2-[2-(4-fluoro-phenyl)-ethylsulfanyl]-propionic acid methyl ester (4.93 g, 10.66 mmol) was dissolved in THF (100 mL) and water (50 mL) and cooled down to 0° C. NaOH (6.39 g, 159.88 mmol) was added and the resulting suspension was stirred stirring for 1 h without removing the cooling bath and another 28 h at ambient temperature. 2N HCl was added until pH 2 was reached and the mixture was extracted with EtOAc (3×100 mL). The combined organic layers were dried ($MgSO_4$) and evaporated under reduced pressure to afford the crude product which was directly proceeded to the next step (4.79 g, 95.3%). $^1$H NMR (400 MHz, $CDCl_3$): δ 7.16 (d, 2H), 7.06 (d, 2H), 6.99 (m, 2H), 6.85 (t, 2H), 4.62 (s, 2H), 3.38 (t, 1H), 3.09 (dd, 1H), 2.71-2.82 (m, 5H), 0.844 (s, 9H), 0.00 (s, 6H). Mass Spectrum: M–H$^+$ 447.10.

3-[4-(tert-Butyl-dimethyl-silanyloxymethyl)-phenyl]-2-[2-(4-fluoro-phenyl)-ethylsulfanyl]-propionic acid 2,2,2-trichloro-ethyl ester To a solution of 3-[4-(tert-tutyl-dimethyl-silanyloxymethyl)-phenyl]-2-[2-(4-fluoro-phenyl)-ethylsulfanyl]-propionic acid (4.79 g, 10.68 mmol) and 2,2,2-trichloroethanol (1.67 g, 11.22 mmol) in anhydrous DCM (300 mL) was first added EDC×HCl (2.66 g, 13.89 mmol) then DMAP (13 mg, 0.1 mmol) under nitrogen atmosphere at 0° C. After complete addition the cooling bath was removed and the reaction mixture was stirred at ambient temperature until no starting material was left. The mixture was diluted with water and aq. HCl (2N) and extracted with DCM. The combined organic layers were dried ($MgSO_4$) and the solvent was evaporated under reduced pressure to afford the crude product which was directly proceeded to the next step (5.47 g, 88.3%). $^1$H NMR (400 MHz, $CDCl_3$): δ 7.16 (t, 2H), 7.10 (d, 2H), 7.01 (t, 2H), 6.87 (t, 2H), 4.61 (q, 4H), 3.48 (dd, 1H), 3.12 (dd, 1H), 2.73-2.89 (m, 5H), 0.85 (s, 9H), 0.00 (s, 6H). Mass Spectrum: M–H$^+$ 579.03.

2-[2-(4-Fluoro-phenyl)-ethylsulfanyl]-3-(4-hydroxymethyl-phenyl)-propionic acid 2,2,2 trichloro-ethyl ester To a solution of 3-[4-(tert-butyl-dimethyl-silanyloxymethyl)-phenyl]-2-[2-(4-fluoro-phenyl)-ethylsulfanyl]-propionic acid 2,2,2-trichloro-ethyl ester (5.47 g, 9.43 mmol) in anhydrous acetonitrile (200 mL) was dropwise added $BF_3 \times Et_2O$ (1.10 mL, 9.43 mmol) at 0° C. The mixture was stirred for 30 min. 2N aq. HCl (50 mL) and $H_2O$ (100 mL) were added and the mixture was extracted with DCM. The combined organic layers were dried ($MgSO_4$) and evaporated to give the crude product which was purified by flash chromatography using DCM/MeOH 95:5 as the eluent. The product was obtained as an (3.62 g, 82.5%). $^1$H NMR (400 MHz, $CDCl_3$): δ 7.19 (d, 2H), 7.10 (d, 2H), 7.01 (m, 2H), 6.87 (t, 2H), 4.65 (d, 1H), 4.56 (m, 3H), 3.48 (dd, 1H), 3.12 (dd, 1H), 2.73-2.91 (m, 5H). Mass Spectrum: M–H$^+$ 464.90.

2-[2-(4-Fluoro-phenyl)-ethylsulfanyl]-3-[4-(2-hydroxy-ethyl)-phenyl]-propionic acid 2,2,2-trichloro-ethyl ester The title compound was prepared from 2-chloro-3-[4-(2-hydroxy-ethyl)-phenyl]-propionic acid 2,2,2-trichloro-ethyl ester (2.57 g, 7.14 mmol) and 2-(4-fluoro-phenyl)-ethanethiol (1.23 g, 7.85 mmol) as described for 3-[4-(tert-butyl-dimethyl-silanyloxy-methyl)-phenyl]-2-[2-(4-fluoro-phenyl)-ethylsulfanyl]-propionic acid methyl ester. After purification by flash chromatography with n-heptane/EtOAc 5:1 as the eluent the product was obtained as an oil (1.0 g, 29.2%). $^1$H NMR (300 MHz, $CDCl_3$): δ 7.10-7.14 (m, 6H), 6.93-6.99 (t, 2H), 4.65-4.76 (q, 2H), 3.82-3.86 (t, 2H), 3.55-3.60 (dd, 2H), 3.17-3.25 (dd, 2H), 2.81-3.00 (m, 7H).

2-[2-(4-Fluoro-phenyl)-ethylsulfanyl]-3-[4-(3-hydroxy-propyl)-phenyl]-propionic acid 2,2,2-trichloro-ethyl ester The title compound was prepared from 2-chloro-3-[4-(3-hydroxy-propyl)-phenyl]-propionic acid 2,2,2-trichloro-ethyl ester (0.74 g, 1.98 mmol) and 2-(4-fluoro-phenyl)-ethanethiol (0.34 g, 2.17 mmol) as described for 3-[4-(tert-butyl-dimethyl-silanyloxy-methyl)-phenyl]-2-[2-(4-fluoro-phenyl)-ethylsulfanyl]-propionic acid methyl ester. After repeated purification by flash chromatography with n-heptane/EtOAc 9:1 as the eluent the product was obtained as an oil (94 mg, 9.6%). $^1$H NMR (300 MHz, $CDCl_3$): δ 7.10-7.11 (m, 6H), 6.94-6.98 (t, 2H), 4.65-4.75 (q, 2H), 3.64-3.68 (t, 2H), 3.58-3.61 (dd, 2H), 3.17-3.23 (dd, 2H), 2.80-2.97 (m, 5H), 2.65-2.70 (t, 2H), 1.86-1.89 (m, 2H).

3-(4-Carboxymethyl-phenyl)-2-[2-(4-fluoro-phenyl)-ethylsulfanyl]-propionic acid 2,2,2-trichloro-ethyl ester The title compound was prepared from 3-(4-carboxymethyl-phenyl)-2-chloro-propionic acid 2,2,2-trichloro-ethyl ester (1.17 g, 3.13 mmol) and 2-(4-fluoro-phenyl)-ethanethiol (0.53 g, 3.44 mmol) as described for 3-[4-(tert-butyl-dimethyl-silanyloxy-methyl)-phenyl]-2-[2-(4-fluoro-phenyl)-ethylsulfanyl]-propionic acid methyl ester. After purification by flash chromatography with n-heptane/EtOAc 10:1 as the eluent the product was obtained as a solid (611 mg, 39.6%). $^1$H NMR (300 MHz, $CDCl_3$): δ 7.09-7.23 (m, 6H), 6.94-6.99 (m, 2H), 4.65-4.77 (q, 2H), 3.56-3.61 (m, 3H), 3.18-3.28 (dd, 1H), 2.78-3.02 (m, 5H).

4-[2-[2-(4-Fluoro-phenyl)-ethylsulfanyl]-2-(2,2,2-trichloro-ethoxycarbonyl)-ethyl]-benzoic acid 2-[2-(4-Fluoro-phenyl)-ethylsulfanyl]-3-(4-hydroxymethyl-phenyl)-propionic acid 2,2,2-trichloro ethyl ester (0.81 g, 1.74 mmol) was dissolved in acetone (75 mL) and potassium permanganate (0.33 g, 2.09 mmol) was added. The resulting purple solution was stirred at for 18 h. First sat. aq. Na₂SO₃ (15 mL) was added and after stirring for 5 min. 2N aq. HCl (30 mL) was added as well. The resulting clear and colorless solution was extracted with EtOAc and CH₂Cl₂ and the combined organic layers were dried (MgSO₄) and evaporated under reduced pressure to afford the crude product which was purified by flash chromatography on silica gel using DCM/MeOH 95:5 as the eluent. The title product was obtained as a solid (556 mg, 66.6%). ¹H NMR (400 MHz, CDCl₃): δ 8.02 (d, 2H), 7.29 (d, 2H), 7.07-7.10 (m, 2H), 6.94 (t, 2H), 4.70 (q, 2H), 3.57 (dd, 1H), 3.29 (dd, 1H), 3.05 (dd, 1H), 2.81-2.91 (m, 4H). Mass Spectrum: M−H⁺ 478.93.

3-(4-Carboxymethyl-phenyl)-2-[2-(4-fluoro-phenyl)-ethanesulfonyl]-propionic acid 2,2,2-trichloro-ethyl ester A solution of 3-(4-carboxymethyl-phenyl)-2-[2-(4-fluoro-phenyl)-ethylsulfanyl]-propionic acid 2,2,2-trichloro-ethyl ester (400 mg, 0.81 mmol) in anhydrous DCM was cooled down to 0° C. and 3-chloroperbenzoic acid (294 mg, 1.70 mmol) was added in several portions. The ice bath was removed after 15 min stirring and the reaction was proceeded at ambient temperature for 36 h. THF was added to the reaction causing a precipitation of a white solid. The inhomogeneous reaction mixture was filtered through a phase separator filled with NaHCO₃. The filtrate was dried (Na₂SO₄) and evaporated under reduced pressure to afford a slightly yellow solid which was dissolved in EtOAc and extracted with sat. aq. NaHCO₃ and brine. After drying the organic phase over Na₂SO₄, the solvent was evaporated again and the title compound was obtained as a solid (372 mg, 87.2%). No further purification was done. ¹H NMR (400 MHz, CDCl₃): δ 6.71-6.79 (m, 6H), 6.56-6.60 (t, 2H), 4.28 (d, 2H), 3.05-3.17 (m, 6H), 2.90-2.98 (m, 3H), 2.73-2.77 (t, 2H).

4-[2-[2-(4-Fluoro-phenyl)-ethylsulfanyl]-2-(2,2,2-trichloro-ethoxycarbonyl)-ethyl]-benzoic acid 2-phenyl-5-trifluoromethyl-oxazol-4-ylmethylester To a solution of 4-[2-[2-(4-fluoro-phenyl)-ethylsulfanyl]-2-(2,2,2-trichloro-ethoxy-carbonyl)-ethyl]-benzoic acid (278 mg, 0.58 mmol) and (2-phenyl-5-trifluoromethyl-oxazol-4-yl)-methanol (155 mg, 0.64 mmol) in anhydrous DCM (20 mL) was first added EDC×HCl (144 mg, 0.75 mmol) then DMAP (1.0 mg, 0.006 mol) under nitrogen atmosphere at 0° C. After complete addition the cooling bath was removed and the reaction mixture was stirred at ambient temperature until no starting material was left. The mixture was diluted with water and aq. HCl (2N) and extracted with DCM. The combined organic layers were dried (MgSO₄) and the solvent was evaporated under reduced pressure. The crude product was purified by flash chromatography using n-heptane/EtOAc 4:1 as the eluent to afford the final product as an oil (289 mg, 56.6%). ¹H NMR (400 MHz, CDCl₃): δ 8.02 (d, 2H), 7.93 (d, 1H), 7.40-7.47 (m, 2H), 7.19-7.29 (m, 4H), 7.02 (dt, 2H), 6.89 (dt, 2H), 5.34 (d, 2H), 4.64 (q, 2H), 3.50 (dd, 1H), 3.18-3.24 (dd, 1H), 2.73-2.98 (m, 5H), 1.1 (s, 2H). Mass Spectrum: M−H⁺ 703.91.

2-Phenyl-5-trifluoromethyl-oxazole-4-carboxylic acid 4-[2-[2-(4-fluoro-phenyl)ethylsulfanyl]-2-(2,2,2-trichloro-ethoxycarbonyl)-ethyl]-benzyl ester The title compound was prepared from 2-[2-(4-fluoro-phenyl)-ethylsulfanyl]-3-(4-hydroxymethyl-phenyl)-propionic acid 2,2,2 trichloro-ethyl ester (675 mg, 1.45 mmol) and 2-phenyl-5-trifluoromethyl-oxazole-4-carboxylic acid (410 mg, 1.59 mmol) in the same manner as described for 4-[2-[2-(4-fluoro-phenyl)-ethylsulfanyl]-2-(2,2,2-trichloro-ethoxycarbonyl)-ethyl]-benzoic acid 2-phenyl-5-trifluoromethyl-oxazol-4-ylmethylester. The crude product was obtained as an oil which was carried on to the next step without further purification (892 mg, 79.4%). ¹H NMR (500 MHz, CDCl₃): δ 8.15 (d, 2H), 7.57 (d, 1H), 7.52 (t, 2H), 7.41 (d, 2H), 7.12 (t, 2H), 6.97 (t, 2H), 5.42 (s, 2H), 4.72 (q, 2H), 3.59 (dd, 1H), 3.25 (dd, 1H), 2.78-3.05 (m, 5H). Mass Spectrum: M+H⁺ 705.89.

4-[2-[2-(4-Fluoro-phenyl)-ethylsulfanyl]-2-(2,2,2-trichloro-ethoxycarbonyl)-ethyl]-benzoic acid 2-(5-methyl-2-phenyl-oxazol-4-yl)-ethyl ester The title compound was prepared from 4-[2-[2-(4-fluoro-phenyl)-ethylsulfanyl]-2-(2,2,2-trichloro-ethoxycarbonyl)-ethyl]-benzoic acid (220 mg, 0.46 mmol) and 2-(5-methyl-2-phenyl-oxazol-4-yl)-ethanol (103 mg, 0.50 mmol) in the same manner as described for 4-[2-[2-(4-fluoro-phenyl)-ethylsulfanyl]-2-(2,2,2-trichloro-ethoxy-carbonyl)-ethyl]-benzoic acid 2-phenyl-5-trifluoromethyl-oxazol-4-ylmethylester. The crude product was purified by flash chromatography using n-heptane/EtOAc 7:3 as the eluent to afford the final product as an oil (280 mg, 83.5%). ¹H NMR (400 MHz, CDCl₃): δ 7.91-7.96 (m, 3H), 7.39-7.41 (m, 3H), 7.22-7.25 (m, 3H), 7.06-7.09 (m, 2H), 6.94 (t, 2H), 4.71 (m, 1H), 4.64 (m, 1H), 4.56 (t, 1H), 3.88-3.92 (m, 2H), 3.55 (m, 1H), 3.29 (m, 1H), 2.69-2.04 (m, 6H), 2.32 (s, 3H). Mass Spectrum: M+H⁺ 666.14, M−H⁺ 664.39.

2-[2-(4-Fluoro-phenyl)-ethylsulfanyl]-3-{4-[2-(5-methyl-2-phenyl-oxazo-1-4-yl) acetoxymethyl]-phenyl}-propionic acid 2,2,2-trichloro-ethyl ester The title compound was prepared from 2-[2-(4-fluoro-phenyl)-ethylsulfanyl]-3-(4-hydroxymethyl-phenyl)-propionic acid 2,2,2-trichloroethyl ester (512 mg, 1.1 mmol) and 2-(5-methyl-2-phenyl-oxazol-4-yl)-acetic acid (261 mg, 1.2 mmol) in the same manner as described for 4-[2-[2-(4-fluoro-phenyl)-ethylsulfanyl]-2-(2,2,2-trichloro-ethoxy-carbonyl)-ethyl]-benzoic acid 2-phenyl-5-trifluoromethyl-oxazol-4-ylmethyl ester. The product was obtained without further purification as an oil (751 mg, 94.1%). ¹H NMR (500 MHz, CDCl₃): δ 8.06 (d, 2H), 7.44 (m, 3H), 7.29 (m, 2H), 7.20 (d, 2H), 7.10-7.13 (m, 2H), 6.98 (t, 2H), 5.16 (s, 2H), 4.73 (q, 2H), 3.58 (dd, 1H), 3.22 (dd, 1H), 2.84-3.00 (m, 5H). Mass Spectrum: M+H⁺666.00.

4-[2-[2-(4-Fluoro-phenyl)-ethylsulfanyl]-2-(2,2,2-trichloro-ethoxycarbonyl)-ethyl]-benzoic acid 4-methanesulfonyloxy-benzyl ester The title compound was prepared from 4-[2-[2-(4-fluoro-phenyl)-ethylsulfanyl]-2-(2,2,2-trichloro-ethoxycarbonyl)- ethyl]-benzoic acid (65 mg, 0.135 mmol) and methane-sulfonic acid 4-hydroxymethyl-phenyl ester (27.4 mg, 0.136 mmol) in the same manner as described for 4-[2-[2-(4-fluoro-phenyl)-ethylsulfanyl]-2-(2,2,2-trichloro-ethoxy-carbonyl)-ethyl]-benzoic acid 2-phenyl-5-trifluoromethyl-oxazol-4-yl-methylester. The crude product was purified by flash chromatography using n-heptane/EtOAc 7:3 as the eluent to afford the final product as an oil (47.6 mg, 45%). $^1$H NMR (400 MHz, CDCl$_3$): δ 7.95-7.97 (d, 2H), 7.47-7.49 (d, 2H), 7.24-7.29 (m, 4H), 7.07-7.08 (m, 2H), 6.91-6.95 (m, 2H), 5.33 (s, 2H), 4.62-4.75 (dd, 2H), 3.55 (t, 1H), 3.25 (t, 1H), 3.13 (s, 3H), 2.79-3.04 (m, 6H). Mass Spectrum: M–H$^+$ 663.04.

2-[2-(4-Fluoro-phenyl)-ethanesulfonyl]-3-[4-(4-trifluoromethyl-benzyloxycarbonylmethyl)-phenyl]-propionic acid 2,2,2-trichloro-ethyl ester 3-(4-Carboxymethyl-phenyl)-2-[2-(4-fluoro-phenyl)-ethanesulfonyl]-propionic acid 2,2,2-trichloro-ethyl ester (121 mg, 0.23 mmol) was dissolved in anhydrous DMF (2.0 mL) and TBTU (147 mg, 0.46 mmol), N-methyl morpholine (46.5 mg, 0.46 mmol) and 4-(trifluoromethyl)benzyl alcohol (81.06 mg, 0.46 mmol) were added under nitrogen atmosphere. The reaction was stirred at ambient temperature for 18 h. EtOAc was added and the mixture was extracted with water and brine. After drying the organic layer over Na$_2$SO$_4$ the solvent was evaporated under reduced pressure to afford the crude product as an oil (161 mg, 102.3%). No further purification was done. $^1$H NMR (400 MHz, CDCl$_3$): δ 7.44-7.62 (m, 6H), 7.12-7.23 (m, 4H), 6.97-7.02 (t, 2H) 5.14 (s, 2H), 4.74 (s, 2H), 4.69 (d, 1H), 3.62 (s, 2H), 3.34-58 (m, 4H), 3.15-3.19 (t, 2H).

2-[2-(4-Fluoro-phenyl)-ethylsulfanyl]-3-{4-[2-(4-methanesulfonyloxy-phenyl)-ethylsulfanylcarbonyl]-phenyl}-propionic acid 2,2,2-trichloro-ethyl ester 4-[2-[2-(4-Fluoro-phenyl)-ethylsulfanyl]-2-(2,2,2-trichloro-ethoxycarbonyl)-ethyl]-benzoic acid (60 mg, 0.125 mmol) was dissolved in anhydrous DCM and oxalyl chloride (0.14 mmol) was added followed by a catalytic amount of DMF. After 30 min stirring at ambient temperature, the reaction was concentrated by evaporating the solvent under reduced pressure. The remaining oil was dissolved in anhydrous DCM again and DMAP (1.0 mg) was added under nitrogen atmosphere. Methanesulfonic acid 4-(2-mercapto-ethyl)-phenyl ester, dissolved in anhydrous DCM was added dropwise and the reaction was stirred for 18 h at ambient temperature. EtOAc was added and the mixture was extracted with aq. KHSO$_4$, aq. Na$_2$CO$_3$ and brine. The organic layer was dried (Na$_2$SO$_4$), filtered and finally concentrated under reduced pressure to afford the crude title compound as an oil (78 mg, 89.9%). No further purification was done. $^1$H NMR (400 MHz, CDCl$_3$): δ 7.06-7.24 (m, 10H), 6.93-6.95 (t, 2H), 4.65-4.70 (dd, 2H), 3.58 (m, 2H), 3.18 (m, 2H), 3.10 (s, 3H), 2.87-2.95 (m, 4H), 2.74-2.82 (m, 3H).

Synthesis of Starting Materials and Intermediates Regarding Examples 21-27

(5-Methyl-2-phenyl-oxazol-4-yl)-acetic acid

The title compound is commercially available.

(4-tert-Butoxycarbonylamino-phenyl)-acetic acid

The title compound is commercially available.

4-Hydroxy-benzoic acid methyl ester

The title compound is commercially available.

3-Benzyl-4-benzyloxy-benzaldehyde

The title compound was synthesized according the following reference:
WO2001040172A1

4-Benzyloxy-3-methyl-benzaldehyde

The title compound was synthesized according the following reference:
Bioorganic & Medicinal Chemistry Letters 13(3), 399-403, 2003.

(Diethoxy-phosphoryl)-ethoxy-acetic acid ethyl ester

The title compound was synthesized according the following reference:
Organic Process Research & Development 7(1), 82-88, 2003.

4-(tert-Butyl-dimethyl-silanyloxymethyl)-benzaldehyde

Bioorganic & Medicinal Chemistry Letters 5(4), 363-366, 1995.

(S)-2-Ethoxy-3-(4-hydroxy-phenyl)-propionic acid ethyl ester

The title compound was prepared according the following reference:
WO2001040159A1

4-Methanesulfonyloxy-benzoic acid methyl ester

4-Hydroxy-benzoic acid methyl ester (3.19 g, 21 mmol) was dissolved together with pyridine (1.97 g, 25 mmol) in dry THF (20 mL) and after cooling down to 0° C., methanesulfonyl chloride (2.29 g, 20 mmol) was added dropwise. The ice bath was removed and mixture was stirred at r.t. for 5 h. After diluting with DCM and extraction with water and aq. HCl (2N), the organic layer was dried (MgSO$_4$) and evaporated to afford the crude but highly pure product as a solid which was used in the next step without further purification (4.38 g, 95.1%). $^1$H NMR (400 MHz, CDCl$_3$): δ 8.07-8.09 (d, 2H), 7.32-7.34 (d, 2H), 3.90 (s, 3H), 3.16 (s, 3H).

Methanesulfonic acid 4-hydroxymethyl-phenyl ester

Under nitrogen atmosphere 4-methanesulfonyloxy-benzoic acid methyl ester (2.3 g, 10 mmol) was dissolved in dry THF (50 mL) and LiAlH$_4$ (0.28 g, 10 mmol) was added at 0° C. After the addition was completed the ice bath was removed and stirring was continued at r.t. for 2 h. The mixture was cooled down to 0° C. again and excess LiAlH$_4$ was hydrolyzed by the addition of MeOH, H$_2$O and aq. HCl (2N). After extracting DCM the combined organic layers were dried (MgSO$_4$) and evaporated under reduced pressure to afford the crude but mainly pure product as an oil which was used in the next step without further purification (1.95 g, 96.4%). $^1$H NMR (400 MHz, CDCl$_3$): δ 7.35-7.37 (d, 2H), 7.21-7.23 (d, 2H), 4.65 (s, 2H), 3.09 (s, 3H).

(S)-2-Ethoxy-3-(4-hydroxy-phenyl)-propionic acid benzyl ester (S)-2-Ethoxy-3-(4-hydroxy-phenyl)-propionic acid ethyl ester (8.1 g, 34 mmol) was dissolved in benzylic alcohol (14.7 g, 135 mmol) and freshly washed sodium hydride (1.63 g, 41 mmol) was cautiously added under nitrogen atmosphere. The resulting mixture was warmed up to 50° C. under vacuum and after 6 h toluene was added and the mixture was extracted with aq. KHSO$_4$ (2N). The combined organic layers were dried and evaporated under high vacuum at 70° C. to afford title compound as an oil (9.51 g, 93.1%). $^1$H NMR (400 MHz, CDCl$_3$): δ 7.19-7.40 (m, 5H), 7.03-7.06 (d, 2H), 6.68-6.71 (d, 2H), 5.14 (s, 2H), 4.03-4.06 (t, 1H), 3.57-3.61 (m, 1H), 3.36-3.40 (m, 1H), 2.97 (s, 1H), 1.14-1.18 (t, 3H).

(S)-3-{4-[2-(4-tert-Butoxycarbonylamino-phenyl)-acetoxy]-phenyl}-2-ethoxy-propionic acid benzyl ester To a solution of (4-tert-butoxycarbonylamino-phenyl)-acetic acid (100 mg, 0.39 mmol), N,N'-diisopropylcarbodiimide (60 mg, 0.47 mmol) and DMAP (15 mg, 0.12 mmol) in dry acetonitrile (15 mL) was added (S)-2-ethoxy-3-(4-hydroxy-phenyl)-propionic acid benzyl ester (120 mg, 0.39 mmol). The mixture was stirred for 3 h at r.t. before the solvent was evaporated and the remaining crude product directly purified by HPLC. The title compound was obtained as a solid (48 mg, 22.6%). $^1$H NMR (400 MHz, CDCl$_3$): δ 7.25-7.36 (m, 9H), 7.16-7.18 (d, 2H), 6.91-6.93 (d, 2H), 5.12 (s, 2H), 4.00-4.03 (dd, 1H), 3.77 (s, 2H), 3.55-3.29 (m, 1H), 3.30-3.36 (m, 1H), 2.97-2.99 (m, 2H), 1.51 (s, 9H), 1.11-1.14 (t, 3H).

(S)-2-Ethoxy-3-{4-[2-(5-methyl-2-phenyl-oxazol-4-yl)-acetoxy]-phenyl}-propionic acid benzyl ester To a solution of (5-methyl-2-phenyl-oxazol-4-yl)-acetic acid (3.29 g, 15.2 mmol) and (S)-2-ethoxy-3-(4-hydroxy-phenyl)-propionic acid benzyl ester (4.56 g, 15.2 mmol) in dry DCM (70 mL) was added EDC×HCl (3.49 g, 18.22 mmol) and DMAP (0.37 g, 3.03 mmol) under nitrogen atmosphere. After stirring for 1 h at ambient temperature the mixture was extracted with saturated aq. NaHCO$_3$, aq. HCl (0.05N) and with saturated aq. NaHCO$_3$ again. The organic layer was dried and the remaining crude product purified by HPLC. The title compound was obtained as an oil (4.15 g, 54.7%). $^1$H NMR (400 MHz, CDCl$_3$): δ 7.99-7.80 (d, 2H), 7.25-7.43 (m, 8H), 7.18-7.20 (d, 2H), 6.99-7.01 (d, 2H), 5.12 (s, 2H), 4.01-4.04 (m, 1H), 3.80 (s, 2H), 3.57-3.61 (m, 1H), 3.31-3.35 (m, 1H), 2.98-3.00 (m, 2H), 2.41 (s, 3H), 1.11-1.15 (t, 3H).

(E/Z)-3-(3-Benzyl-4-benzyloxy-phenyl)-2-ethoxy-acrylic acid ethyl ester

Under nitrogen atmosphere freshly prepared KOtBu (5.01 g, 44.6 mmol) was suspended in tert-butyl methyl ether (150 mL) and (diethoxy-phosphoryl)-ethoxy-acetic acid ethyl ester (7.98 g, 29.7 mmol) was added dropwise. After 60 min. stirring the mixture was cooled down to 0° C. and 3-benzyl-4-benzyloxy-benzaldehyde (4.50 g, 14.88 mmol) was added in small portions. The ice bath was removed and the homogenous mixtures was stirred at r.t. for another 60 min. before it was diluted with water and diethylether. The phases were separated and the aq. layer was re-extracted with diethylether. The combined organic layers were dried (Na$_2$SO$_4$) and evaporated and the remaining crude product was purified by column chromatography using n-heptane/EtOAc (4:1) as the eluent. The title compound was obtained as an oil as a mixture of E/Z isomers (3.96 g, 51.2%). $^1$H NMR (400 MHz, CDCl$_3$): δ 7.60-7.63 (m, 2H), 7.18-7.39 (m, 10H), 6.91 (s, 1H), 5.10 (s, 2H), 4.22-4.30 (q, 2H), 4.09 (s, 2H), 3.89-3.95 (q, 2H), 1.33-1.39 (t, 3H), 1.27-1.31 (t, 3H).

(E/Z)-3-(4-Benzyloxy-3-methyl-phenyl)-2-ethoxy-acrylic acid ethyl ester

The title compound was prepared from (diethoxy-phosphoryl)-ethoxy-acetic acid ethyl ester (9.53 g, 35.53 mmol) and 4-benzyloxy-3-methyl-benzaldehyde (2.68 g, 11.85 mmol) in the same manner as described for 3-(3-benzyl-4-benzyloxy-phenyl)-2-ethoxy-acrylic acid ethyl ester. The crude product was purified by flash chromatography using with n-heptane/EtOAc/DCM (8:1:1) as the eluent. The title compound was obtained as an oil as a mixture of E/Z isomers (2.70 g, 53.6%). $^1$H NMR (400 MHz, CDCl$_3$): δ 7.69 (s, 1H), 7.61 (s, 1H), 7.29-7.48 (m, 10H), 6.99-7.02 (m, 2H), 6.96 (s, 1H), 6.88 (d, 1H), 6.78 (d, 1H), 6.08 (s, 1H), 5.11 (s, 2H), 5.09 (s, 2H), 4.27-4.33 (q, 2H), 4.12-4.19 (q, 2H), 3.96-4.02 (q, 2H), 3.87-3.94 (q, 2H), 2.32 (s, 3H), 2.25 (s, 3H), 1.31-1.42 (m, 9H), 1.10-1.18 (t, 3H).

(E/Z)-3-[4-(tert-Butyl-dimethyl-silanyloxymethyl)-phenyl]-2-ethoxy-acrylic acid ethyl ester The title compound was prepared from 4-(tert-butyl-dimethyl-silanyloxymethyl)-benzaldehyde (5.88 g, 23.5 mmol) and 4-benzyloxy-3-methyl-benzaldehyde (12.6 g, 47 mmol) in the same manner as described for 3-(3-benzyl-4-benzyloxy-phenyl)-2-ethoxy-acrylic acid ethyl ester. The crude product was used as a mixture of E/Z isomers in the next step without further purification (8.85 g, 103%). $^1$H NMR (400 MHz, CDCl$_3$): δ 7.65-7.67 (d, 2H), 7.07-7.24 (3d, 6H), 6.89 (s, 1H), 6.01 (s, 1H), 4.65 (s, 2H), 4.62 (s, 2H), 3.82-4.22 (5m, 8H), 1.18.1.28 (m, 12H), 0.86 (s, 9H), 0.85 (s, 9H), 0.02 (s, 6H), 0.00 (s, 6H).

3-(3-Benzyl-4-hydroxy-phenyl)-2-ethoxy-propionic acid ethyl ester

Under nitrogen atmosphere (E/Z)-3-(3-benzyl-4-benzyloxy-phenyl)-2-ethoxy-acrylic acid ethyl ester (2.3 g, 5.5 mmol) was dissolved in EtOH (50 mL) and Pd/C (10% Pd, 0.1 g) was added. The reaction vessel was sealed, evacuated and connected to a hydrogene line. After 24 h stirring at room temperature under atmospheric pressure, the catalyst was filtered off, repeatedly washed with EtOH and the combined filtrates were concentrated in vacuo to afford the crude product which was purified by column chromatography using n-heptane/EtOAc (7:3) as the eluent. The title compound was obtained as an (2.02 g, 90%). $^1$H NMR (400 MHz, CDCl$_3$): δ 7.19-7.25 (m, 5H), 6.96-6.99 (m, 2H), 6.66-6.68 (d, 1H), 4.09-4.15 (q, 2H), 3.94-3.97 (m, 3H), 3.56-3.59 (m, 1H), 3.31-3.36 (m, 1H), 2.91-2.92 (d, 2H), 1.12-1.16 (t, 3H), 1.18-1.22 (t, 3H). Mass Spectrum: M−H$^+$ 327.08.

2-Ethoxy-3-(4-hydroxy-3-methyl-phenyl)-propionic acid ethyl ester

The title compound was prepared from (E/Z)-3-(4-benzyloxy-3-methyl-phenyl)-2-ethoxy-acrylic acid ethyl ester (2.7 g, 7.93 mmol) in the same manner as described for 3-(3-benzyl-4-hydroxy-phenyl)-2-ethoxy-propionic acid ethyl ester. The crude product was used in the next step without further purification (1.9 g, 85%). $^1$H NMR (400 MHz, CDCl$_3$): δ 6.96 (s, 1H), 6.88-6.92 (d, 1H), 6.64-6.67 (d, 1H), 4.13-4.20 (q, 2H), 3.96-4.00 (t, 1H), 3.56-3.62 (m, 1H), 3.34-3.39 (m, 1H), 2.90-2.92 (d, 2H), 2.19 (s, 3H), 1.14-1.28 (m, 6H).

3-[4-(tert-Butyl-dimethyl-silanyloxymethyl)-phenyl]-2-ethoxy-propionic acid ethyl ester The title compound was prepared from (E/Z)-3-[4-(tert-butyl-dimethyl-silanyloxymethyl)-phenyl]-2-ethoxy-acrylic acid ethyl ester (8.7 g, 23.8 mmol) in the same manner as described for 3-(3-benzyl-4-hydroxy-phenyl)-2-ethoxy-propionic acid ethyl ester. The crude product was proceeded on to the next step without further purification (7.78 g, 89%). $^1$H NMR (400 MHz, CDCl$_3$): δ 7.10-7.19 (m, 4H), 4.62 (s, 2H), 4.04-4.10 (q, 2H), 3.89-3.92 (t, 1H), 3.48-3.53 (m, 1H), 3.23-3.27 (m, 1H), 2.89-2.91 (m, 2H), 1.08 (t, 3H), 1.05 (t, 3H), 0.85 (s, 9H), 0.00 (s, 6H).

3-(3-Benzyl-4-hydroxy-phenyl)-2-ethoxy-propionic acid

To a solution of 3-(3-benzyl-4-hydroxy-phenyl)-2-ethoxy-propionic acid ethyl ester (0.38 g, 1.16 mmol) in MeOH (5 mL), a solution of KOH (1.62 g, 29 mmol) in H$_2$O (5 mL) was added. The mixture was stirred for 2 h at room temperature then acidified with aq. HCl (10%) and extracted with dichloromethane. The combined organic layers were dried and evaporated and the remaining crude product was purified by column chromatography to yield the title compound as an oil (0.35 g, 74.8%). Mass Spectrum: M+H$^+$ 300.94, M−H$^+$ 298.99.

2-Ethoxy-3-(4-hydroxy-3-methyl-phenyl)-propionic acid

The title compound was prepared from 2-ethoxy-3-(4-hydroxy-3-methyl-phenyl)-propionic acid ethyl ester (0.85 g, 2.28 mmol) in the same manner as described for 3-(3-benzyl-4-hydroxy-phenyl)-2-ethoxy-propionic acid. The crude product was used in the next step without further purification (0.71 g, 85%). $^1$H NMR (400 MHz, CDCl$_3$): δ 6.98 (s, 1H), 6.90-6.93 (d, 1H), 6.64-6.66 (d, 1H), 4.03-4.07 (dd, 1H), 3.57-3.65 (m, 1H), 3.41-3.46 (m, 1H), 2.88-3.05 (ddd, 2H), 2.20 (s, 3H), 1.15-1.20 (t, 3H).

3-[4-(tert-Butyl-dimethyl-silanyloxymethyl)-phenyl]-2-ethoxy-propionic acid

The title compound was prepared from 3-[4-(tert-butyl-dimethyl-silanyloxymethyl)-phenyl]-2-ethoxy-propionic acid ethyl ester (1.1 g, 3.0 mmol) in the same manner as described for 3-(3-benzyl-4-hydroxy-phenyl)-2-ethoxy-propionic acid. The crude product was obtained as a solid and used in the next step without further purification (0.73 g, 65%). $^1$H NMR (400 MHz, CDCl$_3$): δ 7.11-7.18 (m, 4H), 4.63 (s, 2H), 3.96-3.99 (m, 1H), 3.48-3.52 (m, 1H), 3.31-3.37 (m, 1H), 3.01-3.05 (dd, 1H), 2.87-2.92 (dd, 1H), 1.07 (t, 3H), 0.85 (s, 9H), 0.00 (s, 6H).

3-(3-Benzyl-4-hydroxy-phenyl)-2-ethoxy-propionic acid benzyl ester

Oxalyl chloride (0.364 g, 2.87 mmol) was added dropwise to a mixture of 3-(3-benzyl-4-hydroxy-phenyl)-2-ethoxy-propionic acid (0.345 g, 1.15 mmol) and a catalytic amount of DMF in dry DCM (2.0 mL). The mixture was stirred for 17 h at room temperature before the excess oxalyl chloride was evaporated in vacuo. The remaining carboxylic acid chloride was redissolved in dry DCM (3.0 mL) and benzyl alcohol (0.15 g, 1.38 mmol) was added under nitrogen atmosphere. After stirring for 24 h at room temperature the solvent was removed in vacuo and the resulting oil was purified by column chromatography using DCM/MeOH (96:4) as the eluent to afford the title compound as an oil (0.22 g, 36.8%). Mass Spectrum: M−H$^+$ 388.94.

2-Ethoxy-3-(4-hydroxy-3-methyl-phenyl)-propionic acid benzyl ester

The title compound was prepared from 2-ethoxy-3-(4-hydroxy-3-methyl-phenyl)-propionic acid (0.71 g, 3.15 mmol) in the same manner as described for 3-(3-benzyl-4-hydroxy-phenyl)-2-ethoxy-propionic acid benzyl ester. The crude product was purified by column chromatography using n-heptane/EtOAc (3:2) as the eluent and the title compound was obtained as an oil (0.51 g, 51.6%). $^1$H NMR (400 MHz, CDCl$_3$): δ 7.26-7.38 (m, 5H), 6.96 (s, 1H), 6.97-6.91 (d, 1H), 6.65-6.67 (d, 1H), 5.16 (s, 2H), 4.08-4.12 (t, 1H), 3.61-3.66 (m, 1H), 3.39-3.44 (m, 1H), 2.96-2.99 (d, 2H), 2.20 (s, 3H), 1.17-1.22 (t, 3H).

3-[4-(tert-Butyl-dimethyl-silanyloxymethyl)-phenyl]-2-ethoxy-propionic acid 2,2,2-trichloro-ethyl ester Under nitrogen atmosphere 3-[4-(tert-butyl-dimethyl-silanyloxymethyl)-phenyl]-2-ethoxy-propionic acid (0.135 g, 0.4 mmol) and 2,2,2-trichloro ethanol (0.06 g, 0.4 mmol) were dissolved in dry DCM (5 mL) and DMAP (2 mg, 0.02 mmol) was added followed by EDC×HCl (0.092 g, 0.48 mmol) at 0° C. The mixture was stirred for 18 h at ambient temperature, then diluted with DCM and extracted with aq. HCl (2N) and water. The organic layer was separated, dried (MgSO$_4$) and evaporated to afford the crude product which was used in the next step without further purification (0.176 g, 93.6%). $^1$H NMR (400 MHz, CDCl$_3$): δ 7.12-7.19 (m, 4H), 4.62-4.71 (q, 2H), 4.63 (s, 2H), 4.05-4.08 (m, 1H), 3.55-3.59 (m, 1H), 3.27-3.31 (m, 1H), 2.92-3.03 (m, 2H), 1.08 (t, 3H).

2-Ethoxy-3-(4-hydroxymethyl-phenyl)-propionic acid 2,2,2-trichloro-ethyl ester To a solution of 3-[4-(tert-butyl-dimethyl-silanyloxymethyl)-phenyl]-2-ethoxy-propionic acid 2,2,2-trichloro ethyl ester (0.07 g, 0.15 mmol) in acetonitrile was added BF$_3$×Et$_2$O (0.02 mL, 0.15 mmol) at 0° C. The mixture was allowed to stir for 30 min. at this temperature before it was quenched with aq. HCl (2N) and extracted with DCM. The separated organic layer was washed with water, dried (MgSO$_4$) and evaporated under reduced pressure to afford the title compound which was proceeded on to the next step without purification (0.044 g, 83%). $^1$H NMR (400 MHz, CDCl$_3$): δ 7.24-7.29 (m, 4H), 4.70-4.80 (q, 2H), 4.65 (s, 2H), 4.13-4.16 (dd, 1H), 3.63-3.67 (m, 1H), 3.35-3.39 (m, 1H), 3.01-3.13 (m, 2H), 1.16 (t, 3H).

4-[2-Ethoxy-2-(2,2,2-trichloro-ethoxycarbonyl)-ethyl]-benzoic acid

2-Ethoxy-3-(4-hydroxymethyl-phenyl)-propionic acid 2,2,2-trichloroethyl ester (0.044 g, 0.125 mmol) was dissolved in acetone (3 mL) and KMnO$_4$ (0.039 g, 0.247 mmol)

was added and the purple solution was stirred for 4 h at room temperature. Saturated aq. Na₂SO₃ solution was added and after 2 min. stirring, the mixture was diluted with EtOAc and aq. HCl (2N) resulting in two clear and colorless phases. The organic layer was separated and dried (MgSO₄) and evaporated to afford the desired carboxylic acid which was proceeded on to the next step without further purification (0.034 g, 75%). ¹H NMR (400 MHz, CDCl₃): δ 8.01-8.03 (d, 2H), 7.36-7.38 (d, 2H), 4.73-4.83 (q, 2H), 4.15-4.18 (m, 1H), 3.65-3.69 (m, 1H), 3.33-3.37 (m, 1H), 3-07-3.20 (m, 2H), 1.14 (t, 3H).

3-{3-Benzyl-4-[2-(5-methyl-2-phenyl-oxazol-4-yl)-acetoxy]-phenyl}-2-ethoxy-propionic acid benzyl ester To a solution of 3-(3-benzyl-4-hydroxy-phenyl)-2-ethoxy-propionic acid benzyl ester (45 mg, 0.11 mol) and (5-methyl-2-phenyl-oxazol-4-yl)-acetic acid (25 mg, 0.11 mmol) in dry DCM (2.0 mL) first DMAP (2.8 mg, 0.02 mmol) and then EDC×HCl (26.5 mg, 0.13 mmol) was added and the mixture was stirred under nitrogen atmosphere at room temperature for 17 h. The solvent was removed under vacuo and the product was isolated out of the remaining oil by column chromatography using n-heptane/EtOAc (4:1) as the eluent. The title compound was obtained as an oil (56.1 mg, 82.6%). ¹H NMR (400 MHz, CDCl₃): δ 7.95 (m, 2H), 7.40 (m, 2H), 7.32 (m, 2H), 7.25 (m, 2H), 6.98-67.20 (m, 10H), 5.08, (d, 2H), 3.97 (t, 1H), 3.85 (s, 2H), 3.70 (s, 2H), 3.55 (m, 1H), 3.28 (m, 1H), 2.93 (d, 2H), 2.32 (s, 3H), 1.1 (t, 3H).

3-{3-Benzyl-4-[2-(4-tert-butoxycarbonylamino-phenyl)-acetoxy]-phenyl}-2-ethoxy-propionic acid benzyl ester The title compound was prepared from 3-(3-benzyl-4-hydroxy-phenyl)-2-ethoxy-propionic acid benzyl ester (48 mg, 0.123 mol) and (4-tert-butoxycarbonylamino-phenyl)-acetic acid (31 mg, 0.123 mmol) in the same manner as described for 3-{3-benzyl-4-[2-(5-methyl-2-phenyl-oxazol-4-yl)-acetoxy]-phenyl}-2-ethoxy-propionic acid benzyl ester. The crude product was purified by column chromatography using n-heptane/EtOAc (7:3) as the solvent to afford the product as a as an oil (65.1 mg, 72.2%). ¹H NMR (400 MHz, CDCl₃): δ 6.90-7.32 (m, 17H), 6.42 (br s, 1H), 5.08 (d, 2H), 3.97-3.98 (m, 1H), 3.73 s, 2H), 3.67 (s, 2H), 3.51-3.60 (m, 1H), 3.22-3.32 (m, 1H), 2.92-2.94 (m, 2H), 1.51 (s, 9H), 1.06-1.10 (t, 3H). Mass Spectrum: M–H⁺ 622.87.

2-Ethoxy-3-{3-methyl-4-[2-(5-methyl-2-phenyl-oxazol-4-yl)-acetoxy]-phenyl}-propionic acid benzyl ester The title compound was prepared from 2-ethoxy-3-(4-hydroxy-3-methyl-phenyl)-propionic acid benzyl ester (311 mg, 0.98 mmol) and (5-methyl-2-phenyl-oxazol-4-yl)-acetic acid (215 mg, 0.98 mmol) in the same manner as described for 3-{3-benzyl-4-[2-(5-methyl-2-phenyl-oxazol-4-yl)-acetoxy]-phenyl}-2-ethoxy-propionic acid benzyl ester. The crude product was purified by column chromatography using DCM/iPrOH (95:5) as the eluent to afford the pure product as a solid (480 mg, 94.5%). ¹H NMR (400 MHz, CDCl₃): δ 7.98-8.02 (m, 2H), 7.26-7.44 (m, 8H), 6.91-7.05 (m, 3H), 5.12 (s, 2H), 4.01-4.05 (t, 1H), 3.82 (s, 2H), 3.56-3.59 (m, 1H), 3.34-3.37 (m, 1H), 2.95-2.97 (d, 2H), 2.43 (s, 3H), 2.11 (s, 3H), 1.12-1.17 (t, 3H).

3-{4-[2-(4-tert-Butoxycarbonylamino-phenyl)-acetoxy]-3-methyl-phenyl}-2-ethoxy-propionic acid benzyl ester The title compound was prepared from 2-ethoxy-3-(4-hydroxy-3-methyl-phenyl)-propionic acid benzyl ester (38 mg, 0.15 mmol) and (4-tert-butoxycarbonylamino-phenyl)-acetic acid (47 mg, 0.15 mmol) in the same manner as described for 3-{3-benzyl-4-[2-(5-methyl-2-phenyl-oxazol-4-yl)-acetoxy]-phenyl}-2-ethoxy-propionic acid benzyl ester. The crude product was purified by column chromatography using n-heptane/EtOAc (2:3) as the eluent to afford the product as a solid (32 mg, 85%). ¹H NMR (400 MHz, CDCl₃): δ 7.26-7.38 (m, 9H), 6.99-7.02 (m, 2H), 6.83-6.86 (d, 1H), 6.49 (br s, 1H), 5.12 (s, 2H), 4.00-4.05 (t, 1H), 3.80 (s, 2H), 3.58-3.61 (m, 1H), 3.31-3.36 (m, 1H), 2.94-2.96 (d, 2H), 1.98 (s, 3H), 1.52 (s, 9H), 1.12-1.16 (t, 3H).

4-[2-Ethoxy-2-(2,2,2-trichloro-ethoxycarbonyl)-ethyl]-benzoic acid 4-methane sulfonyloxy-benzyl ester The title compound was prepared from 4-[2-ethoxy-2-(2,2,2-trichloro-ethoxy carbonyl)-ethyl]-benzoic acid (0.032 g, 0.087 mmol) and methanesulfonic acid 4-hydroxymethyl-phenyl ester (0.018 g, 0.09 mmol) in the same manner as described for 3-{3-benzyl-4-[2-(5-methyl-2-phenyl-oxazol-4-yl)-acetoxy]-phenyl}-2-ethoxy-propionic acid benzyl ester. The crude product was purified by column chromatography using n-heptane/EtOAc (2:3) as the eluent to afford the title compound as a solid (0.023, 47%). ¹H NMR (400 MHz, CDCl₃): δ 7.96-7.98 (d, 2H), 7.47-7.49 (d, 2H), 7.33-7.35 (d, 2H), 7.27-7.29 (d, 2H), 5.33 (s, 2H), 4.68-4.81 (q, 2H), 4.15 (m, 1H), 3.65 (m, 1H), 3.32 (m, 1H), 3.08-3.15 (m, 2H), 3.13 (s, 3H), 1.13 (t, 3H).

Synthesis of Starting Material and Intermediates Regarding Examples 28-44

2-Bromomethyl-benzoic acid 2,2,2-trichloro-ethyl ester

To a suspension of 2-(bromomethyl)benzoic acid (1.0 g, 4.65 mmol), β-trichloroethanol (0.54 mL, 5.58 mmol) and DMAP (0.057 g, 0.465 mmol) in DCM (20 mL) was added EDC×HCl (1.34 g, 6.98 mmol) at 0° C. The solution was stirred at 0° C. for 0.5 h and thereafter allowed to reach rt and stirred overnight. Water was added and the phases were separated through a phase separator. The organic portion was concentrated and the crude was submitted to flash chromatography using heptane and EtOAc (90/10) as eluent to yield the titled compound (0.80 g, 50%) as an oil; ¹H NMR (400 MHz, CDCl₃): δ 4.99 (s, 2H), 5.08 (s, 2H), 7.46 (m, 1H), 7.60 (m, 2H), 8.13 (d, 1H).

2-(3-Carboxymethyl-phenylsulfanylmethyl)-benzoic acid 2,2,2-trichloro-ethyl ester Cesium carbonate (1.69 g, 5.20 mmol) was added to a mixture of 3-mercapto-phenylacetic acid (0.73 g, 4.33 mmol) and 2-bromomethyl-benzoic acid 2,2,2-trichloro-ethyl ester (1.50 g, 4.33 mmol) in DMF (25 mL). The mixture was stirred for 1 h at rt. Water was added and the mixture was washed with diethyl ether. The aqueous phase was made acidic (pH5-3) with 2M HCl and thereafter extracted with diethyl ether. The combined organic phases were dried (Na₂SO₄) and concentrated to give the titled compound (1.88 g, 100%); ¹H NMR (400 MHz, CDCl$_3$): δ 3.50 (s, 2H), 4.46 (s, 2H), 4.88 (s, 2H), 7.01-7.08 (m, 1H), 7.10-7.16 (m, 4H), 7.22-7.35 (m, 2H), 8.00 (d, 1H); Mass spectrum: M–H$^+$ 432.

2-[3-(4-Trifluoromethyl-benzyloxycarbonylmethyl)-phenylsulfanylmethyl]-benzoic acid 2,2,2-trichloro-ethyl ester (4-Trifluoromethyl-phenyl)-methanol (58 mg, 0.332 mmol) was added to a stirred mixture of 2-(3-carboxymethyl-phenylsulfanylmethyl)-benzoic acid 2,2,2-trichloro-ethyl ester (120 mg, 0.277 mmol), EDC×HCl (80 mg, 0.415 mmol), DMAP (3.4 mg, 0.028 mmol) and DCM (4 mL). The reaction mixture was stirred at rt overnight. More DCM was added and the mixture was washed with 0.25M HCl, the organic phase was dried through a phase separator and concentrated. The crude was submitted to flash chromatography using heptane and EtOAc (90/10) as the eluent to yield the titled compound (105 mg, 64%) as a colourless oil; $^1$H NMR (400 MHz, CDCl$_3$): δ 3.62 (s, 2H), 4.54 (s, 2H), 4.96 (s, 2H), 5.18 (s, 2H), 7.09-7.15 (m, 1H), 7.18-7.24 (m, 4H), 7.30-7.43 (m, 4H), 7.60 (d, 2H), 8.08 (d, 1H); Mass spectrum: M–H$^+$ 590.

2-(4-Carboxy-phenylsulfanylmethyl)-benzoic acid 2,2,2-trichloro-ethyl ester

The titled compound was prepared according to the method described for 2-(3-carboxymethyl-phenylsulfanylmethyl)-benzoic acid 2,2,2-trichloro-ethyl ester above from 4-mercapto-benzoic acid (60 mg, 0.389 mmol), 2-bromomethyl-benzoic acid 2,2,2-trichloro-ethyl ester (135 mg, 0.389 mmol), cesium carbonate (152 mg, 0.467 mmol) and DMF (2 mL). The crude material (85 mg, 52%) was used for the next step without further purification; $^1$H NMR (400 MHz, CDCl$_3$): δ 4.70 (s, 2H), 5.15 (s, 2H), 7.40 (d, 2H), 7.44-7.60 (m, 3H), 7.82 (d, 2H), 7.96 (d, 1H), 12.9 (br s, 1H); Mass spectrum: M–H$^+$ 418.

2-(4-Hydroxymethyl-phenylsulfanylmethyl)-benzoic acid 2,2,2-trichloro-ethyl ester To a solution of 2-(4-Carboxy-phenylsulfanylmethyl)-benzoic acid 2,2,2-trichloro-ethyl ester (80 mg, 0.191 mmol) in THF (1 mL) at 0° C. was added dropwise BH$_3$-THF (0.4 mL, 1.0M solution in THF). The reaction was stirred at 0° C. for 0.5 h after the addition was complete, thereafter the cooling bath was removed and the reaction was stirred for 2 h at rt. The reaction was quenched at 0° C. by careful addition of THF/H$_2$O, 80/20 followed by dropwise addition of 2M HCl. The mixture was stirred for an additional 10 minutes and thereafter diluted with water. THF was removed and the water phase was extracted with DCM and the combined organic phase was dried through a phase separator and concentrated to give the titled compound (70 mg, 91%) as an oil; $^1$H NMR (400 MHz, CDCl$_3$): δ 4.53 (s, 2H), 4.64 (s, 2H), 4.94 (s, 2H), 7.19-7.30 (m, 5H), 7.30-7.36 (m, 1H), 7.37-7.44 (m, 1H), 8.06 (d, 1H).

2-{4-[2-(4-Trifluoromethyl-phenyl)-acetoxymethyl]-phenylsulfanylmethyl}benzoic acid 2,2,2-trichloro-ethyl ester 2-(4-Hydroxymethyl-phenylsulfanylmethyl)-benzoic acid 2,2,2-trichloro-ethyl ester (70 mg, 0.173 mmol) was added to a stirred mixture of (4-trifluoromethyl-phenyl) acetic acid (39 mg, 0.190 mmol), EDC×HCl (50 mg, 0.259 mmol), DMAP (2.1 mg, 0.017 mmol) and DCM (3 mL). The reaction mixture was stirred at rt overnight, according to LC-MS analysis the reaction was uncomplete. Additional EDC×HCl (50 mg, 0.259 mmol), DMAP (2.1 mg, 0.017 mmol) and 2-(4-hydroxymethyl-phenylsulfanylmethyl)-benzoic acid 2,2,2-trichloro-ethyl ester (70 mg, 0.173 mmol) were added and the mixture was stirred for 3 h. More DCM was added and the mixture was washed with 0.25M HCl, the organic portion was dried through a phase separator and concentrated to give the titled compound (112 mg, 100%); Mass spectrum: M–H$^+$ 590.

2-(4-Carboxymethyl-phenylsulfanylmethyl)-benzoic acid 2,2,2-trichloro-ethyl ester The titled compound was prepared according to the method described for 2-(3-carboxymethyl-phenylsulfanylmethyl)-benzoic acid 2,2,2-trichloro-ethyl ester above from 4-mercapto-phenylacetic acid (0.73 g, 4.33 mmol), 2-bromomethyl-benzoic acid 2,2,2-trichloro-ethyl ester (1.50 g, 4.33 mmol), cesium carbonate (1.69 g, 5.20 mmol) and DMF (25 mL). The crude material (1.88 g, 100%) was used for the next step without further purification; Mass spectrum: M–H$^+$ 432.

2-[4-(4-Trifluoromethyl-benzyloxycarbonylmethyl)-phenylsulfanylmethyl]-benzoic acid 2,2,2-trichloro-ethyl ester The titled compound was prepared according to the method described for 2-[3-(4-trifluoromethyl-benzyloxycarbonylmethyl)-phenylsulfanylmethyl]-benzoic acid 2,2,2-trichloro-ethyl ester above from 2-(4-carboxymethyl-phenylsulfanylmethyl)-benzoic acid 2,2,2-trichloro-ethyl ester (155 mg, 0.357 mmol), (4-trifluoromethyl-phenyl)-methanol (157 mg, 0.893 mmol), EDC×HCl (206 mg, 1.072 mmol), DMAP (4.4 mg, 0.036 mmol) and DCM (3 mL). The crude was submitted to flash chromatography using heptane and EtOAc (90/10) as eluent to yield the titled compound (74 mg, 35%) as an oil; $^1$H NMR (400 MHz, CDCl$_3$): δ 3.64 (dd, 2H), 4.54 (s, 2H), 4.96 (s, 2H), 5.17 (s, 2H), 7.16 (d, 2H), 7.18-7.28 (m, 3H), 7.31-7.44 (m, 4H), 7.60 (d, 2H), 8.08 (d, 1H)); Mass spectrum: M–H$^+$ 590.

2-{3-[1-(4-Trifluoromethyl-phenyl)-ethoxycarbonylmethyl]phenylsulfanylmethyl}-benzoic acid 2,2,2-trichloro-ethyl ester The titled compound was prepared according to the method described for 2-[3-(4-trifluoromethyl-benzyloxycarbonylmethyl)-phenylsulfanylmethyl]-benzoic acid 2,2,2-trichloro-ethyl ester above from 2-(3-carboxymethyl-phenylsulfanylmethyl)-benzoic acid 2,2,2-trichloro-ethyl ester (168 mg, 0.387 mmol), 1-(4-trifluoromethyl-phenyl)-ethanol (88 mg, 0.465 mmol), EDC×HCl (111 mg, 0.581 mmol), DMAP (4.7 mg, 0.039 mmol) and DCM (5 mL). The crude was submitted to flash chromatography using heptane and EtOAc (90/10) as eluent to yield the titled compound (157 mg, 67%) as an oil; $^1$H NMR (400 MHz, CDCl$_3$): δ 1.52 (d, 3H), 3.59 (dd, 2H), 4.52 (s, 2H), 4.96 (s, 2H), 5.90 (m, 2H), 7.09-7.12 (m, 1H), 7.17-7.23 (m, 4H), 7.30-7.42 (m, 4H), 7.57 (d, 2H), 8.08 (d, 1H); Mass spectrum: M–H$^+$ 604.

2-{3-[2-(4-Trifluoromethyl-phenyl)-ethoxycarbonylmethyl]phenylsulfanylmethyl}-benzoic acid 2,2,2-trichloro-ethyl ester The titled compound was prepared according to the method described for 2-[3-(4-trifluoromethyl-benzyloxycarbonylmethyl)-phenylsulfanylmethyl]-benzoic acid 2,2,2-trichloro-ethyl ester above from 2-(3-carboxymethyl-phenyl-sulfanylmethyl)-benzoic acid 2,2,2-trichloro-ethyl ester (168 mg, 0.387 mmol), 1-(4-trifluoromethyl-phenyl)-ethanol (88 mg, 0.465 mmol), EDCxHCl (111 mg, 0.581 mmol), DMAP (4.7 mg, 0.039 mmol) and DCM (4 mL). The crude was submitted to flash chromatography using heptane and EtOAc (90/10) as eluent to yield the titled compound (160 mg, 68%) as an oil; $^1$H NMR (400 MHz, CDCl$_3$): δ 2.67 (dd, 2H), 3.23 (s, 2H), 4.03 (dd, 2H), 4.27 (s, 2H), 4.67 (s, 2H), 6.74 (br d, 1H), 6.85-6.99 (m, 6H), 7.06 (dd, 1H), 7.13 (dd, 1H), 7.22 (d, 2H), 7.79 (d, 1H); Mass spectrum: M−H$^+$ 604.

Synthesis of Starting Materials and Intermediates Regarding Example 45

4-Hydroxy-benzoic acid benzyl ester

The title compound is commercially available.

2-Bromo-2-methyl-propionic acid tert-butyl ester

The title compound is commercially available.

5-Chloromethyl-4-methyl-2-(4-trifluoromethyl-phenyl)-thiazole

The title compound is commercially available.

4-(1-tert-Butoxycarbonyl-1-methyl-ethoxy)-benzoic acid benzyl ester

Sodium hydride (0.664 g, 26.28 mmol) was added to a solution of 4-hydroxy-benzoic acid benzyl ester (5.0 g, 21.90 mmol) and 2-bromo-2-methyl-propionic acid tert-butyl ester (5.86 g, 26.28 mmol) in DMF (50 mL). The resulting mixture was warmed up to 80° C. and stirred for 1 h before additional 2-bromo-2-methyl-propionic acid tert-butyl ester (5.86 g, 26.28 mmol) and sodium hydride (0.664 g, 26.28 mmol) was added. After 18 h at 80° C. about 50% product could be detected by LC-MS. The reaction mixture was diluted with water and extracted with Et$_2$O. The combined organic layers were dried (MgSO$_4$) and evaporated and the desired product was isolated from the remaining mixture by HPLC. The title compound was obtained as an oil (2.5 g, 30.8%). $^1$H NMR (500 MHz, CDCl$_3$): δ 7.96 (d, 2H), 7.43 (d, 2H), 7.37 (t, 2H), 7.33 (d, 1H), 6.82 (d, 2H), 5.32 (s, 2H), 1.60 (s, 6H), 1.40 (s, 9H).

4-(1-tert-Butoxycarbonyl-1-methyl-ethoxy)-benzoic acid 4-(1-tert-Butoxycarbonyl-1-methyl-ethoxy)-benzoic acid benzyl ester (2.75 g, 7.42 mmol) was dissolved in EtOAc and Pd/C (10% Pd, ca. 100 mg) was added. The reaction vessel was evacuated and connected to a hydrogen line. After 3 h stirring at r.t. under H$_2$ atmosphere the catalyst was filtered off and the filtrate was evaporated. The crude product was used in the next step without further purification (2.0 g, 96.1%). $^1$H NMR (500 MHz, CDCl$_3$): δ 7.99 (d, 2H), 6.84 (d, 2H), 1.62 (s, 6H), 1.41 (s, 9H).

4-(1-tert-Butoxycarbonyl-1-methyl-ethoxy)-benzoic acid 4-methyl-2-(4-trifluoromethyl-phenyl)-thiazol-5-yl methyl ester A mixture of 4-(1-tert-butoxycarbonyl-1-methyl-ethoxy)-benzoic acid (0.112 g, 0.4 mmol) and 5-chloromethyl-4-me-thyl-2-(4-trifluoromethyl-phenyl)-thiazole (0.117 g, 0.4 mmol), Cs$_2$CO$_3$ (0.261 g, 0.8 mmol) and KI (7 mg, 0.04 mmol) in DMF (5 mL) was warmed up to 50° C. and stirred for 30 min. After diluting with H$_2$O the mixture was extracted with Et$_2$O and the combined organic layers were dried (Na$_2$SO$_4$) and evaporated. The crude product was used in the next step without further purification although a significant amount of DMF was left (0.535 mg, 40.8%). $^1$H NMR (500 MHz, CDCl$_3$): δ 7.99 (d, 2H), 7.92 (d, 2H), 7.64 (d, 2H), 6.80 (d, 2H), 5.44 (s, 2H), 2.54 (s, 3H), 1.58 (s, 6H), 1.38 (s, 9H).

Synthesis of Examples

Example 1

4-Methanesulfonyloxy-benzoic acid 4-{2-carboxy-2-[2-(4-fluoro-phenyl)-ethylsulfanyl]-ethyl}-benzyl ester

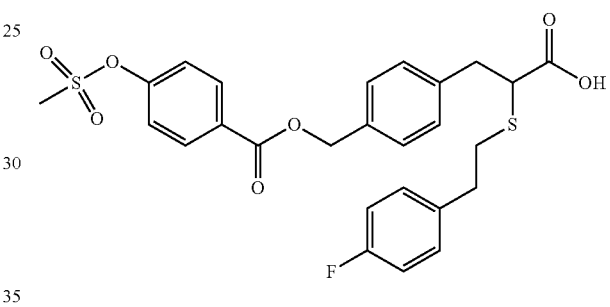

Step 1: To a solution of 2-[2-(4-fluoro-phenyl)-ethylsulfa-nyl]-3-(4-hydroxymethyl-phenyl)-propionic acid 2,2,2 trichloro-ethyl ester (70 mg, 0.15 mmol) and (4-methane-sulfonyloxy-phenyl)-acetic acid (32.5 mg, 0.15 mmol) in anhydrous DCM (3.0 mL) was added EDCxHCl (37.5 mg, 0.195 mmol) and DMAP (0.18 mg, 0.002 mmol) under nitrogen atmosphere at 0° C. After complete addition the cooling bath was removed and the homogenous mixture was stirred at ambient temperature until no starting material was left. The mixture was diluted with water and 2N aq. HCl and extracted with DCM. The combined organic layers were dried (MgSO$_4$) and the solvent subsequently evaporated under reduced pressure to afford the desired ester intermediate which was used in the next step without further purification.

Step 2: The crude 2,2,2-trichloro ethyl ester derivative (68.7 mg, 0.10 mmol) was dissolved in DCM (5.0 mL) and zinc (135 mg, 2.0 mmol) was added followed by acetic acid (0.6 mL, 10 mmol). The resulting suspension was stirred at ambient temperature until no starting material was left. After filtering off and washing the zinc with MeOH and EtOAc, the combined organic layers were extracted with water, dried (MgSO$_4$) and evaporated under reduced pressure. The title compound was obtained through purification of the crude product by column chromatography using CH$_2$Cl$_2$/MeOH 95:5 as the eluent. The pure product was obtained as an oil (19.7 mg, 35.8%). $^1$H NMR (400 MHz, CD$_3$OD): δ 8.09-8.11 (d, 2H), 7.31-7.34 (m, 4H), 7.19-7.21 (d, 2H), 7.04-7.07 (m, 2H), 6.90-6.94 (t, 2H), 5.31 s, 2H), 3.44-3.46 (t, 1H), 3.12-3.18 (t, 1H), 3.15 (s, 1H), 2.79-2.92 (m, 5H). Mass Spectrum: M+H− 531.04.

Example 2

2-[2-(4-Fluoro-phenyl)-ethylsulfanyl]-3-{4-[2-(4-methanesulfonyloxy-phenyl)-acetoxymethyl]-phenyl}-propionic acid

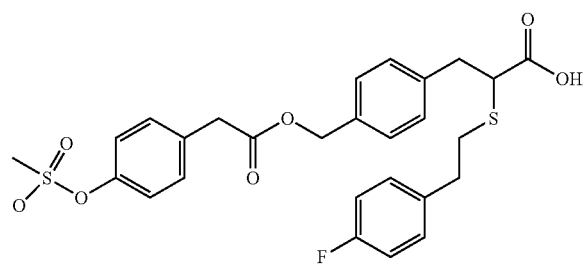

The title compound was prepared from 2-[2-(4-fluoro-phenyl)-ethylsulfanyl]-3-(4-hydroxymethyl-phenyl)-propionic acid 2,2,2 trichloro-ethyl ester (33 mg, 0.072 mmol) and (4-methanesulfonyloxy-phenyl)-acetic acid (15 mg, 0.065 mmol) in the same manner as described for example 1. The crude product was purified by flash chromatography (yield: 2.0 mg, 5.6%). Mass Spectrum: M+H⁺ 547.10.

Example 3

2-[2-(4-Fluoro-phenyl)-ethylsulfanyl]-3-[4-(4-trifluoromethyl-benzyloxycarbonylmethyl)-phenyl]-propionic acid

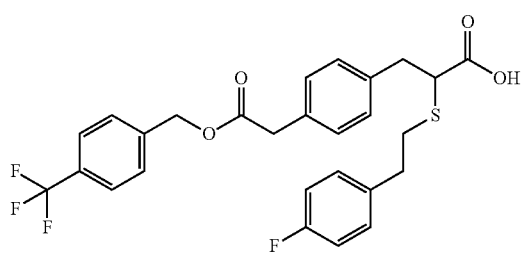 [SMILES: O=C(Cc1ccc(CC(SCCc2ccc(F)cc2)C(=O)O)cc1)OCc1ccc(C(F)(F)F)cc1]

The title compound was prepared from 3-(4-carboxymethyl-phenyl)-2-[2-(4-fluoro-phenyl)-ethylsulfanyl]-propionic acid 2,2,2-trichloro ethyl ester (30 mg, 0.061 mmol) and 4-trifluoromethylbenzyl alcohol (12 mg, 0.067 mmol) in the same manner as described for example 1. The crude product was purified by HPLC (yield: 3.0 mg, 9.4%). ¹H NMR (400 MHz, CDCl₃): δ 7.56 (d, 2H), 7.36 (d, 2H), 7.08-7.19 (m, 6H), 6.90-7.04 (m, 2H), 5.14 (s, 2H), 3.63 (s, 2H), 3.45 (dd, 2H), 3.15 (dd, 2H), 2.80-2.92 (m, 3H).

Example 4

2-[2-(4-Fluoro-phenyl)-ethylsulfanyl]-3-[4-(4-methanesulfonyloxy-benzyloxycarbonylmethyl)-phenyl]-propionic acid

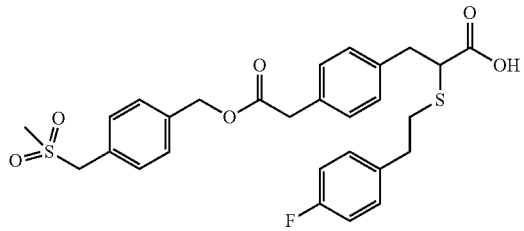 [SMILES: CS(=O)(=O)Cc1ccc(COC(=O)Cc2ccc(CC(SCCc3ccc(F)cc3)C(=O)O)cc2)cc1]

The title compound was prepared from 3-(4-carboxymethyl-phenyl)-2-[2-(4-fluoro-phenyl)-ethylsulfanyl]-propionic acid 2,2,2-trichloro-ethyl ester (30 mg, 0.01 mmol) and methanesulfonic acid 4-hydroxymethyl-phenyl ester (14 mg, 0.067 mmol) in the same manner as described for example 1. The crude product was purified by HPLC (yield: 0.47 mg, 1.4%). Mass Spectrum: M−H⁺ 545.50.

Example 5

2-[2-(4-Fluoro-phenyl)-ethylsulfanyl]-3-(4-{2-[2-(4-methanesulfonyloxy-phenyl)-acetoxy]-ethyl}-phenyl)-propionic acid

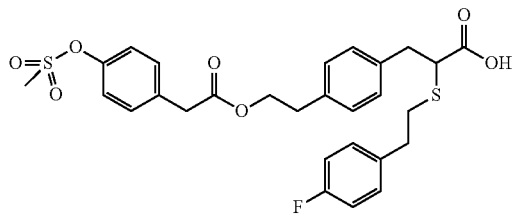 [SMILES: CS(=O)(=O)Oc1ccc(CC(=O)OCCc2ccc(CC(SCCc3ccc(F)cc3)C(=O)O)cc2)cc1]

The title compound was prepared from 2-[2-(4-fluoro-phenyl)-ethylsulfanyl]-3-[4-(2-hydroxy-ethyl)-phenyl]-propionic acid 2,2,2-trichloro-ethyl ester (34 mg, 0.072 mmol) and methanesulfonic acid (4-methanesulfonyloxy-phenyl)-acetic acid (15 mg, 0.065 mmol) in the same manner as described for example 1. The crude product was purified by HPLC (yield: 3.0 mg, 8.2%). ¹H NMR (400 MHz, CDCl₃): δ 7.17-7.24 (m, 4H), 7.00-7.10 (m, 6H), 6.89-6.93 (m, 2H), 4.26 (t, 2H), 3.80 (t, 2H), 3.46-3.50 (dd, 2H), 3.11 (s, 3H), 2.77-2.91 (m, 8H).

Example 6

2-[2-(4-Fluoro-phenyl)-ethylsulfanyl]-3-(4-{3-[2-(4-methanesulfonyloxy-phenyl)-acetoxy]-propyl}-phenyl)-propionic acid The title compound was prepared from 2-[2-(4-fluoro-phenyl)-ethylsulfanyl]-3-[4-(3-hydroxy-propyl)-phenyl]-propionic acid 2,2,2-trichloro-ethyl ester (45 mg, 0.091 mmol) and (4-methanesulfonyloxy-phenyl)-acetic acid (19 mg, 0.083 mmol) in the same manner as described for example 1. The crude product was purified by HPLC (yield: 3.0 mg, 4.2%). $^1$H NMR (400 MHz, CDCl$_3$): δ 7.30-7.32 (d, 2H), 7.21-7.23 (d, 2H), 7.05-7.08 (m, 4H), 6.98-7.00 (d, 2H), 6.90-6.94 (t, 2H), 4.04-4.07 (t, 2H), 3.63 (m, 2H), 3.46 (m, 2H), 3.08 (s, 3H), 2.79-2.90 (m, 5H), 2.54-2.58 (t, 2H), 1.87-1.90 (t, 2H).

Example 7

2-[2-(4-Fluoro-phenyl)-ethylsulfanyl]-3-[4-(2-phenyl-propionyloxymethyl)-phenyl]-propionic acid Step 1: 2-Phenyl-propionic acid (0.112 g, 0.1 mmol) was weighted in the tube, 2-[2-(4-fluoro-phenyl)-ethylsulfanyl]-3-(4-hydroxymethyl-phenyl)-propionic acid 2,2,2-trichloro-ethyl ester (0.516 g, 0.065 mmol) dissolved in 1.0 mL DCM was added followed by EDC×HCl (0.020 g, 0.1 mmol). The reaction was stirred at r.t. for 18 h, then 3.0 mL water was added and the organic layer was isolated via phase separator.

Step 2: First zinc (0.085 g, 1.3 mmol), then acetic acid (2 mL, 33 mmol) was added to the organic phase and the resulting inhomogeneous mixture was stirred at r.t. for 4 h. The zinc was filtered off and subsequently washed with DCM. The combined organic layers were evaporated and the remaining crude product was purified by HPLC to afford the pure product (6.5 g, 21%). $^1$H-NMR (300 MHz, CDCl$_3$): δ 1.51 (d, 3H), 2.75-2.96 (m, 5H), 3.12-3.23 (m, 1H), 3.42-3.51 (m, 1H), 3.71-3.82 (m, 1H), 5.01-5.13 (m, 2H), 6.91-6.99 (m, 2H), 7.04-7.11 (m, 2H), 7.13-7.16 (m, 4H), 7.26-7.32 (m, 5H); Mass Spectrum: M−H+ 465.

Example 8

2-[2-(4-Fluoro-phenyl)-ethylsulfanyl]-3-{4-[2-(4-methoxylphenylacetoxymethyl]phenyl}-propionic acid The title compound was prepared starting from 4-methoxyphenylacetic acid and 2-[2-(4-fluoro-phenyl)-ethylsulfanyl]-3-(4-hydroxymethyl-phenyl)-propionic acid 2,2,2-trichloro-ethyl ester in the same manner as described for example 7 (yield: 6.3 mg, 20%). $^1$H-NMR (300 MHz, CDCl$_3$): δ 2.76-2.99 (m, 5H), 3.13-3.25 (m, 1H), 3.43-3.53 (m, 1H), 3.60 (s, 2H), 3.79 (s, 3H), 5.09 (s, 2H), 6.82-6.89 (m, 2H), 6.91-7.00 (m, 2H), 7.05-7.12 (m, 2H), 7.14-7.30 (m, 6H); Mass Spectrum: M−H+ 481.

Example 9

2-[2-(4-Fluoro-phenyl)-ethylsulfanyl]-3-{4-[2-(4-isobutyl-phenyl)-propionyloxymethyl]-phenyl}-propionic acid The title compound was prepared starting from 2-(4-isobutyl-phenyl)-propionic acid and 2-[2-(4-fluoro-phenyl)-ethylsulfanyl]-3-(4-hydroxymethyl-phenyl)-propionic acid 2,2,2-trichloro-ethyl ester in the same manner as described for example 7 (yield: 5.6 mg, 17%). $^1$H-NMR (300 MHz, CDCl$_3$): δ 0.90 (d, 6H), 1.50 (d, 3H), 1.77-1.92 (m, 1H), 2.45 (d, 2H), 2.75-2.96 (m, 5H), 3.12-3.23 (m, 1H), 3.41-3.50 (m, 1H), 3.74 (q, 1H), 5.00-5.13 (m, 2H), 6.91-6.99 (m, 2H), 7.04-7.23 (m, 10H); Mass Spectrum: M−H+ 521.

Example 10

2-[2-(4-Fluoro-phenyl)-ethylsulfanyl]-3-[4-(2-pyridin-2-yl-acetoxymethyl)-phenyl]-propionic acid The title compound was prepared starting from 2-pyridineacetic acid (HCl salt) and 2-[2-(4-fluoro-phenyl)-ethylsulfanyl]-3-(4-hydroxymethyl-phenyl)-propionic acid 2,2,2-trichloro-ethyl ester in the same manner as described for example 7 (yield: 8.6 mg, 29%). $^1$H-NMR (300 MHz, CDCl$_3$): δ 2.83-3.16 (m, 6H), 3.54-3.71 (m, 1H), 3.64 (s, 2H), 5.06-5.20 (m, 2H), 6.91-7.00 (m, 2H), 7.09-7.35 (m, 7H), 7.66 (brd, 1H), 8.06 (brs, 1H), 8.45 (brd, 1H); Mass Spectrum: M+H$^+$ 455.

Example 11

2-[2-(4-Fluoro-phenyl)-ethylsulfanyl]-3-{4-[2-(4-methyl-piperazin-1-yl)-acetoxymethyl]-phenyl}-propionic acid The title compound was prepared starting from N-methyl piperazino acetic acid and 2-[2-(4-fluoro-phenyl)-ethylsulfanyl]-3-(4-hydroxymethyl-phenyl)-propionic acid 2,2,2-trichloro-ethyl ester in the same manner as described for example 7 (yield: 7.9 mg, 26%). $^1$H-NMR (300 MHz, CDCl$_3$): δ 2.28-2.54 (m, 4H), 2.42 (s, 3H), 2.63-2.88 (m, 4H), 2.88-3.29 (m, 10H), 3.60-3.67 (m, 1H), 5.00-5.21 (m, 2H), 6.91-7.00 (m, 2H), 7.13-7.20 (m, 2H), 7.22-7.33 (m, 4H); Mass Spectrum: M+H+475.

Example 12

4-{2-Carboxy-2-[2-(4-fluoro-phenyl)-ethylsulfanyl]-ethyl}-benzoic acid 2-phenyl-5 trifluoromethyl-oxazol-4-ylmethyl ester 4-[2-[2-(4-Fluoro-phenyl)-ethylsulfanyl]-2-(2,2,2-trichloro-ethoxycarbonyl)-ethyl]-benzoic acid 2-phenyl-5-trifluoromethyl-oxazol-4-ylmethylester (289 mg, 0.41 mmol) was dissolved in DCM (30 mL) and zinc (530 mg, 8.1 mmol) was added followed by acetic acid (2.5 mL, 41.6 mmol). The resulting suspension was stirred for 6 h at ambient temperature. After filtering off and washing the zinc with MeOH and EtOAc, the combined organic layers were extracted with water, dried (MgSO$_4$) and evaporated under reduced pressure. The remaining crude product was purified by flash chromatography using Et$_2$O/DCM/EtOAc 6:3:1 as the eluent to afford the title compound as a solid (yield: 24 mg, 10%). $^1$H NMR (400 MHz, CDCl$_3$): δ 8.07 (d, 2H), 7.98 (d, 2H), 7.43-7.55 (m, 3H), 7.24 (d, 2H), 7.07 (m, 2H), 6.92 (t, 2H), 5.39 (s, 2H), 3.43 (t, 1H), 3.22 (dd, 1H), 2.75-2.99 (m, 5H). Mass spectrum: M+H$^+$ 574.14, M−H$^+$ 572.24.

Example 13

2-Phenyl-5-trifluoromethyl-oxazole-4-carboxylic acid 4-{2-carboxy-2-[2-(4-fluoro-phenyl)-ethylsulfanyl]-ethyl}-benzyl ester The title compound was prepared from 2-Phenyl-5-trifluoromethyl-oxazole-4-carboxylic acid 4-[2-[2-(4-fluoro-phenyl)ethylsulfanyl]-2-(2,2,2-trichloro-ethoxy-carbonyl)-ethyl]-benzyl ester (892 mg, 1.26 mmol) in the same manner as described for example 12. The reaction time was 17 h and the crude product was purified by flash chromatography using n-heptan/EtOAc 1:1 as the eluent. The pure product was obtained as a solid (yield: 275 mg, 38%). $^1$H NMR (400 MHz, CDCl$_3$): δ 8.05 (d, 2H), 7.44-7.58 (m, 3H), 7.37-7.40 (d, 2H), 7.19-7.23 (d, 2H), 7.07 (dt, 2H), 6.92 (dt, 2H), 5.38 (s, 2H), 3.48 (t, 1H), 3.17-3.22 (dd, 1H), 2.76-2.96 (m, 5H). Mass Spectrum: M−H$^+$ 572.02.

Example 14

4-{2-Carboxy-2-[2-(4-fluoro-phenyl)-ethylsulfanyl]-ethyl}-benzoic acid 2-(5-methyl-2 phenyl-oxazol-4-yl)-ethyl ester The title compound was prepared from 4-[2-[2-(4-fluoro-phenyl)-ethylsulfanyl]-2-(2,2,2-trichloro-ethoxycarbonyl)-ethyl]-benzoic acid 2-(5-methyl-2-phenyl-oxazol-4-yl)-ethyl ester (37 mg, 0.056 mmol) in the same manner as described for example 12. The reaction time was 4 h and the crude product was purified by HPFC using n-heptan/EtOAc 4:1 as the eluent. The pure product was obtained as a solid (yield: 10.5 mg, 35.4%). $^1$H NMR (400 MHz, CDCl$_3$): δ 7.90-7.99 (m, 4H), 7.39 (m, 3H), 7.25 (d, 2H), 7.08 (m, 2H), 6.92 (t, 2H), 4.50 (t, 2H), 3.48 (t, 1H), 3.21 (dd, 1H), 2.78-3.00 (m, 7H), 2.36 (s, 3H). Mass spectrum: M+H$^+$ 534.18, M–H$^+$ 532.33.

Example 15

2-[2-(4-Fluoro-phenyl)-ethylsulfanyl]-3-{4-[2-(5-methyl-2-phenyl-oxazol-4-yl) acetoxymethyl]-phenyl}-propionic acid The title compound was synthesized from 2-[2-(4-fluoro-phenyl)-ethylsulfanyl]-3-{4-[2-(5-methyl-2-phenyl-oxazol-1-4-yl)acetoxymethyl]-phenyl}-propionic acid 2,2,2-trichloro-ethyl ester (751 mg, 1.23 mmol) in the same manner as described for example 12. The reaction time was 17 h and the crude product was purified by recrystallisation from iPrOH/iPr$_2$O/n-heptane. The pure product was obtained as a solid (yield: 184 mg, 31%). $^1$H NMR (400 MHz, CDCl$_3$): δ 7.96 (m, 2H), 7.38-7.41 (m, 3H), 7.23-7.28 (d, 2H), 7.15-7.19 (d, 2H), 7.03-7.10 (m, 2H), 6.89-6.96 (dt, 2H), 5.08 (s, 2H), 3.59 (s, 2H), 3.42-3.37 (t, 1H), 3.12-3.20 (dd, 1H), 2.77-2.95 (m, 5H), 2.32 (s, 2H). Mass Spectrum: M+H$^+$ 535.03, M–H$^+$ 532.08.

Example 16

4-{2-Carboxy-2-[2-(4-fluoro-phenyl)-ethylsulfanyl]-ethyl}-benzoic acid 4-methanesulfonyloxy-benzyl ester The title compound was prepared from 4-[2-[2-(4-fluoro-phenyl)-ethylsulfanyl]-2-(2,2,2-trichloro-ethoxycarbonyl)-ethyl]-benzoic acid 4-methanesulfonyloxy-benzyl ester (43.8 mg, 0.066 mmol) in the same manner as described for example 12. The reaction time was 5 h and the crude product was purified by flash chromatography using DCM/MeOH 95:5 as the eluent. The pure product was obtained as an oil (yield: 14.3 mg, 40.7%). $^1$H NMR (400 MHz, CDCl$_3$): δ 7.95 (d, 2H), 7.47 (d, 2H), 7.22-7.28 (m, 4H), 7.03 (m, 2H), 6.90 (m, 2H), 5.32 (s, 2H), 3.42-3.46 (t, 1H), 3.18-3.23 (dd, 1H), 3.12 (s, 3H), 2.75-2.97 (m, 5H). Mass Spectrum: M+H$^+$ 532.96; M–H$^+$ 531.01

Example 17

2-[2-(4-Fluoro-phenyl)-ethanesulfonyl]-3-[4-(4-trifluoromethyl-benzyloxycarbonylmethyl)-phenyl]-propionic acid The title compound was prepared from 2-[2-(4-fluoro-phenyl)-ethanesulfonyl]-3-[4-(4-trifluoromethyl-benzyloxycarbonylmethyl)-phenyl]-propionic acid 2,2,2-trichloro-ethyl ester (170 mg, 0.25 mmol) in the same manner as described for example 12. The reaction time was 2 h and the crude product was purified by HPLC. The pure product was obtained as a solid (yield: 100 mg, 73%). $^1$H NMR (400 MHz, CDCl$_3$) δ 7.48-7.56 (m, 2H), 7.38-7.46 (m, 2H), 7.00-7.17 (m, 6H), 6.91-6.83 (t, 2H), 5.06 (s, 2H), 3.92-4.00 (m, 1H), 3.56 (s, 2H), 3.33-3.44 (m, 1H), 3.10-3.27 (m, 3H), −2.91-3.01 (m, 2H). Mass Spectrum: M–H+ 551.11.

Example 18

2-[2-(4-Fluoro-phenyl)-ethylsulfanyl]-3-{4-[2-(4-methanesulfonyloxy-phenyl)-ethylsulfanylcarbonyl]-phenyl}-propionic acid The title compound was prepared from 2-[2-(4-fluoro-phenyl)-ethylsulfanyl]-3-{4-[2-(4-methanesulfonyloxy-phenyl)-ethylsulfanylcarbonyl]-phenyl}-propionic acid 2,2,2-trichloro-ethyl ester (yield: 100 mg, 0.144 mmol) in the same manner as described for example 12. The reaction time was 18 h and the crude product was purified by HPLC. The pure product was obtained as a solid (yield: 5.0 mg, 6.2%). $^1$H NMR (400 MHz, CDCl$_3$) δ 7.14-7.16 (m, 8H), 7.04-7.07 (m, 2H), 6.89-6.94 (m, 2H), 3.43-3.45 (m, 1H), 3.12-3.17 (dd, 1H), 3.09 (s, 3H), 3.02-3.06 (t, 2H), 2.78-2.91 (m, 7H).

Example 19

(−)-2-[2-(4-Fluoro-phenyl)-ethylsulfanyl]-3-{4-[2-(5-methyl-2-phenyl-oxazol-4-yl)-acetoxymethyl]-phenyl}-propionic acid The two enantiomers of (±)-2-[2-(4-fluoro-phenyl)-ethylsulfanyl]-3-{4-[2-(5-methyl-2-phenyl-oxazol-4-yl)-acetoxymethyl]-phenyl}-propionic acid (200 mg, 0.375 mmol) were separated by chiral chromatography using the column Chiralpak AD™ 250×20 mm (column temperature: 40° C.) with EtOH/formic acid 100/0.1 as the mobile phase. The enantiomer with the negative optical rotation was obtained in 99.1% enantiomeric excess and 87% yield (87 mg). $[\alpha]_D^{20}$=−37.3 (c 0.6 g/ml, MeOH). $^1$H NMR (400 MHz, CDCl$_3$): δ 8.45 (s, 1H), 7.94 (m, 2H), 7.37-7.38 (m, 3H), 7.23-7.25 (d, 2H), 7.15-7.17 (d, 2H), 7.02-7.05 (m, 2H), 6.88-6.92 (t, 2H), 5.08 (s, 2H), 3.60 (s, 2H), 3.43-3.47 (m, 1H), 3.13-3.18 (dd, 1H), 2.76-2.90 (m, 5H), 2.30 (s, 2H). $^{13}$C NMR (400 MHz, CDCl$_3$): δ 176.09, 170.06, 162.71, 160.27, 159.69, 145.89, 137.94, 135.54, 134.22, 130.11, 129.96, 129.88, 129.17, 128.98, 128.64, 128.38, 127.09, 126.08, 115.25, 115.04, 66.60, 47.77, 36.97, 34.77, 33.16, 31.72, 10.20. Mass Spectrum: M+H$^+$ 534.17.

Example 20

4-{(−)-2-Carboxy-2-[2-(4-fluoro-phenyl)-ethylsulfanyl]-ethyl}-benzoic acid 2-(5-methyl-2-phenyl-oxazol-4-yl)-ethyl ester The two enantiomers of 4-{(±)-2-carboxy-2-[2-(4-fluoro-phenyl)-ethylsulfanyl]-ethyl}-benzoic acid 2-(5-methyl-2-phenyl-oxazol-4-yl)-ethyl ester (200 mg, 0.375 mmol) were separated by chiral chromatography using the column Chiralpak AD™ 250×20 mm (column temperature: 40° C.) with EtOH/formic acid 100/0.1 as the mobile phase. The enantiomer with the negative optical rotation was obtained in 99.0% enantiomeric excess and 99% yield (99 mg). $[\alpha]_D^{20}$=−30.0 (c 1 g/ml, MeOH). $^1$H NMR (400 MHz, CDCl$_3$): δ 8.75 (s, 1H), 7.89-7.94 (m, 4H), 7.36-7.38 (m, 3H), 7.24-7.26 (d, 2H), 7.04-7.06 (m, 2H), 6.88-6.92 (t, 2H), 4.46-4.49 (t, 2H), 3.48

(t, 1H), 3.22 (dd, 1H), 2.77-2.97 (m, 7H), 2.30 (s, 3H). $^{13}$C NMR (400 MHz, CDCl$_3$): δ 175.70, 166.20, 162.70, 160.27, 159.77, 145.03, 143.27, 135.50, 135.47, 131.93, 130.10, 129.93, 129.85, 129.73, 129.06, 128.72, 128.66, 127.06, 126.03, 115.26, 115.05, 63.52, 47.56, 37.31, 34.82, 33.21, 25.31, 10.05. Mass Spectrum: M+H+534.17.

Example 21

(S)-2-Ethoxy-3-{4-[2-(5-methyl-2-phenyl-oxazol-4-yl)-acetoxy]-phenyl}-propionic acid

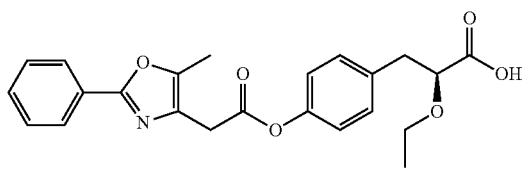 [SMILES: CCO[C@@H](Cc1ccc(OC(=O)Cc2nc(-c3ccccc3)oc2C)cc1)C(=O)O]

(S)-2-Ethoxy-3-{4-[2-(5-methyl-2-phenyl-oxazol-4-yl)-acetoxy]-phenyl}-propionic acid benzyl ester (0.1 g, 0.2 mmol) was dissolved in EtOAc (4 mL) and 10% Pd/C (0.04 g, 0.037 mmol) was added. After evacuation the reaction vessel was connected to a hydrogen line and the hydrogenation was performed at atmospheric pressure at room temperature for 3 h. The catalyst was filtered off, washed with EtOAc and the combined organic filtrates were evaporated under reduced pressure to afford the product as a solid (0.079 g, 96.4%). $^1$H NMR (400 MHz, CDCl$_3$): δ 7.98-7.99 (d, 2H), 7.42 (m, 3H), 7.23-7.25 (d, 2H), 7.02-7.04 (m, 2H), 6.71 (br s, 1H), 4.01-4.02 (m, 1H), 3.80 (s, 2H), 3.57-3.60 (m, 1H), 3.36-3.39 (m, 1H), 3.07-3.10 (m, 1H), 2.94-2.99 (m, 1H), 2.40 (s, 3H), 1.11-1.14 (t, 3H).

Example 22

(S)-3-{4-[2-(4-tert-Butoxycarbonylamino-phenyl)-acetoxy]-phenyl}-2-ethoxy-propionic acid

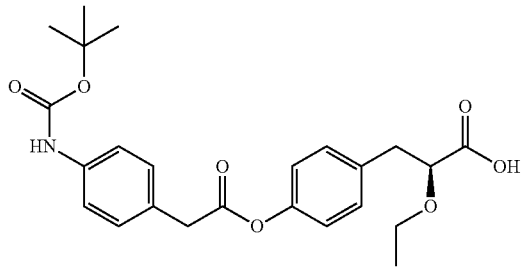 [SMILES: CCO[C@@H](Cc1ccc(OC(=O)Cc2ccc(NC(=O)OC(C)(C)C)cc2)cc1)C(=O)O]

The title compound was prepared from (S)-3-{4-[2-(4-tert-butoxycarbonylamino-phenyl)-acetoxy]-phenyl}-2-ethoxy-propionic acid benzyl ester (0.048 g, 0.09 mmol) in the same manner as described for example 1 (yield: 0.028 g, 70.2%). $^1$H NMR (500 MHz, CD$_3$OD): δ 7.37-7.39 (d, 2H), 7.25-7.28 (m, 4H), 6.92-6.94 (d, 2H), 3.84-3.86 (dd, 1H), 3.80 (s, 2H), 3.57-3.59 (m, 1H), 3.23-3.27 (m, 1H), 2.97-3.03 (dd, 1H), 2.79-2.87 (dd, 1H), 1.51 (s, 9H), 1.07-1.10 (t, 3H).

Example 23

3-{3-Benzyl-4-[2-(5-methyl-2-phenyl-oxazol-4-yl)-acetoxy]-phenyl}-2-ethoxy-propionic acid

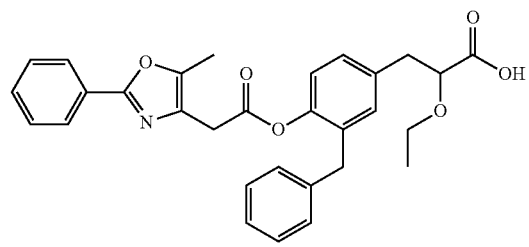 [SMILES: CCOC(Cc1ccc(OC(=O)Cc2nc(-c3ccccc3)oc2C)c(Cc2ccccc2)c1)C(=O)O]

The title compound was prepared from 3-{3-benzyl-4-[2-(5-methyl-2-phenyl-oxazol-4-yl)-acetoxy]-phenyl}-2-ethoxy-propionic acid benzyl ester (0.054 g, 0.09 mmol) in the same manner as described for example 1 with the difference that EtOH was used as the solvent instead of EtOAc. The crude product was purified by column chromatography using DCM/MeOH (95:5) as the eluent and the desired compound was obtained as an oil (0.019 g, 41.3%). $^1$H NMR (400 MHz, CDCl$_3$): δ 7.93-7.96 (m, 2H), 7.39-7.41 (m, 3H), 7.02-7.19 (m, 8H), 3.99 (m, 1H), 3.86 (s, 2H), 3.69 (s, 2H), 3.48 (m, 1H), 3.32 (m, 1H), 3.03-3.09 (dd, 1H), 2.90-2.93 (dd, 1H), 2.29 (s, 3H), 1.04-1.07 (t, 3H).

Example 24

3-{3-Benzyl-4-[2-(4-tert-butoxycarbonylamino-phenyl)-acetoxy]-phenyl}-2-ethoxy-propionic acid

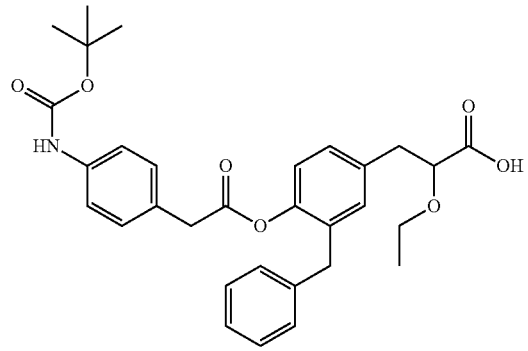 [SMILES: CCOC(Cc1ccc(OC(=O)Cc2ccc(NC(=O)OC(C)(C)C)cc2)c(Cc2ccccc2)c1)C(=O)O]

The title compound was prepared from 3-{3-benzyl-4-[2-(4-tert-butoxycarbonylamino-phenyl)-acetoxy]-phenyl}-2-ethoxy-propionic acid benzyl ester (0.06 g, 0.096 mmol) in the same manner as described for example 1 with the difference that EtOH was used as the solvent instead of EtOAc. The crude product was purified by column chromatography using DCM/MeOH (9:1) as the eluent and the title compound was obtained as an oil (0.047 g, 24.2%). $^1$H NMR (400 MHz, CDCl$_3$): δ 9.28 (s, 1H), 7.38-7.29 (d, 2H), 7.02-7.21 (m, 9H), 6.88-6.91 (d, 1H), 3.79 (s, 2H), 3.50-3.55 (m, 1H), 3.15-3.19

(m, 1H), 2.85-2.87 (dd, 1H), 2.64-2.69 (m, 1H), 2.48-2.50 (m, 1H), 1.45 (s, 9H), 0.91-0.95 (t, 3H). Mass spectrum: M–H⁺ 531.93.

Example 25

2-Ethoxy-3-{3-methyl-4-[2-(5-methyl-2-phenyl-oxazol-4-yl)-acetoxy]-phenyl}-propionic acid

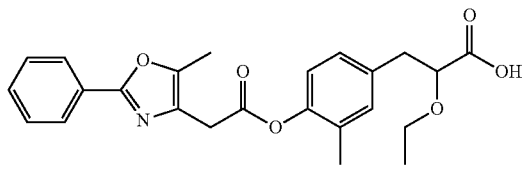 [SMILES: CCOC(Cc1ccc(OC(=O)Cc2nc(-c3ccccc3)oc2C)c(C)c1)C(=O)O]

The title compound was prepared from 2-ethoxy-3-{3-methyl-4-[2-(5-methyl-2-phenyl-oxazol-4-yl)-acetoxy]-phenyl}-propionic acid benzyl ester (0.63 g, 1.22 mmol) in the same manner as described for example 1 with the difference that MeOH was used as the solvent instead of EtOAc. The crude product was purified by column chromatography using DCM/iPrOH (95:5) as the eluent and the title compound was obtained as a solid (0.303 g, 58.3%). ¹H NMR (500 MHz, CDCl₃): δ 7.99-8.02 (m, 2H), 7.43-7.46 (m, 3H), 7.08-7.11 (m, 2H), 6.96-6.97 (d, 1H), 4.01-4.03 (m, 1H), 3.85 (s, 2H), 3.61 (m, 1H), 3.37 (m, 1H), 3.04-3.07 (dd, 1H), 2.95-2.97 (dd, 1H), 2.43 (s, 3H), 2.13 (s, 3H), 1.12-1.14 (t, 3H).

Example 26

3-{4-[2-(4-tert-Butoxycarbonylamino-phenyl)-acetoxy]-3-methyl-phenyl}-2-ethoxy-propionic acid The title compound was prepared from 3-{4-[2-(4-tert-butoxycarbonylamino-phenyl)-acetoxy]-3-methyl-phenyl}-2-ethoxy-propionic acid benzyl ester (0.035 g, 0.064 mmol) in the same manner as described for example 1 with the difference that MeOH was used as the solvent instead of EtOAc. The crude product was purified by column chromatography using DCM/iPrOH (95:5) as the eluent and the title compound was obtained as a solid (0.02 g, 68.4%). ¹H NMR (500 MHz, CD₃OD): δ 7.40-7.42 (d, 2H), 7.29-7.31 (d, 2H), 7.10-7.15 (m, 2H), 6.86-6.87 (d, 1H), 3.84-3.88 (m, 3H), 3.60-3.62 (m, 1H), 3.26-3.29 (m, 1H), 2.96-3.02 (dd, 1H), 2.80-2.86 (dd, 1H), 1.53 (s, 9H), 1.10-1.13 (t, 3H).

Example 27

4-(2-Carboxy-2-ethoxy-ethyl)-benzoic acid 4-methanesulfonyloxy-benzyl ester

To a solution of 4-[2-ethoxy-2-(2,2,2-trichloro-ethoxycarbonyl)-ethyl]-benzoic acid 4-methane sulfonyloxy-benzyl ester (0.02 g, 0.036 mmol) in dry DCM (2 mL) was first added zinc dust (0.047 g, 0.722 mmol), then acetic acid (1.08 mL, 18.06 mmol) at 0° C. The resulting inhomogeneous mixture was stirred for 17 h without removing the ice bath. The zinc was filtered off and washed with DCM and MeOH and the remaining filtrates were combined and evaporated under reduced pressure. The crude product was purified by column chromatography using DCM/MeOH (92:8) as the eluent. The title compound was obtained as an oil (0.005 g, 36%). ¹H NMR (400 MHz, CDCl₃): δ 7.91-7.93 (d, 2H), 7.42-7.44 (d, 2H, 7.19-7.24 (m, 4H), 5.27 (s, 2H), 4.03 (m, 1H), 3.52 (m, 1H), 3.37 (m, 1H), 2.99-3.14 (m, 2H), 3.08 (s, 3H), 2.63 (t, 3H). Mass Spectrum: M–H⁺ 421.23.

Example 28

2-[3-(4-Trifluoromethyl-benzyloxycarbonylmethyl)-phenylsulfanylmethyl]-benzoic acid

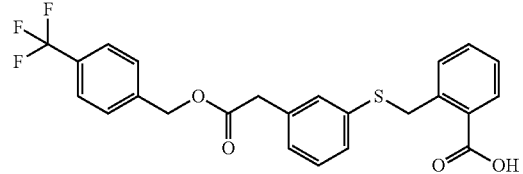 [SMILES: O=C(Cc1cccc(SCc2ccccc2C(=O)O)c1)OCc1ccc(C(F)(F)F)cc1]

2-[3-(4-Trifluoromethyl-benzyloxycarbonylmethyl)-phenylsulfanylmethyl]-benzoic acid 2,2,2-trichloro-ethyl ester (105 mg, 0.177 mmol) was dissolved in DCM (8 mL) and zinc (232 mg, 3.55 mmol) was added. After stirring for 5 minutes HOAc, 97% (1 mL, 18 mmol) was added dropwise. The resulting slurry was stirred for 1.5 h before zinc was filtered off and washed with DCM. The organic phase was washed with water, dried through a phase separator and concentrated. The crude was submitted to flash chromatography using heptane and EtOAc (70/30-60/40) as eluent to give the titled compound (57 mg, 70%) as an oil; ¹H NMR (400 MHz, CDCl₃): δ 3.64 (s, 2H), 4.56 (s, 2H), 5.18 (s, 2H), 7.09-7.14 (m, 1H), 7.16-7.21 (m, 2H), 7.22-7.34 (m, 3H), 7.36-7.43 (m, 3H), 7.60 (d, 2H), 8.00 (d, 1H); Mass spectrum: M–H⁺ 459.

Example 29

2-{4-[2-(4-Trifluoromethyl-phenyl)-acetoxymethyl]-phenylsulfanylmethyl}-benzoic acid

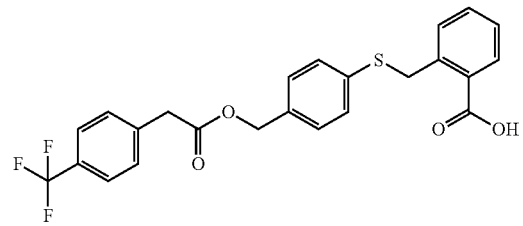 [SMILES: O=C(Cc1ccc(C(F)(F)F)cc1)OCc1ccc(SCc2ccccc2C(=O)O)cc1]

The titled compound was prepared according to the method described for example 1 above from 2-{4-[2-(4-trifluoromethyl-phenyl)-acetoxymethyl]phenylsulfanylmethyl}benzoic acid 2,2,2-trichloro-ethyl ester (112 mg, 0.189 mmol), zinc (247 mg, 3.79 mmol), HOAc, 97% (1.08 mL, 18.9 mmol) and DCM (9 mL). The crude was submitted to flash chromatography using heptane and EtOAc (70/30-60/40) as eluent to give the titled compound (60 mg, 69%) as a solid; ¹H NMR (400 MHz, CDCl₃): δ 3.72 (s, 2H), 4.57 (s, 2H), 5.09 (s, 2H), 7.18 (d, 2H), 7.24-7.30 (m, 3H), 7.31-7.46 (m, 4H), 7.48 (d, 2H), 8.05 (d, 1H); Mass spectrum: M–H⁺ 459.

Example 30

2-[4-(4-Trifluoromethyl-benzyloxycarbonylmethyl)-phenylsulfanylmethyl]-benzoic acid

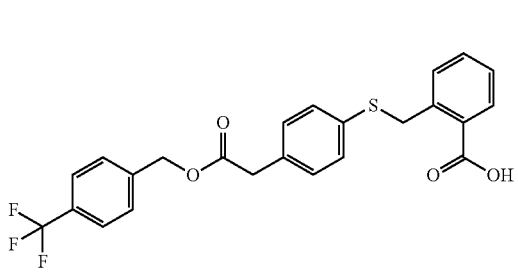 [SMILES: O=C(Cc1ccc(SCc2ccccc2C(=O)O)cc1)OCc1ccc(C(F)(F)F)cc1]

The titled compound was prepared according to the method described for example 1 above from 2-[4-(4-trifluoromethyl-benzyloxycarbonylmethyl)phenylsulfanylmethyl]-benzoic acid 2,2,2-trichloro-ethyl ester (74 mg, 0.125 mmol), zinc (164 mg, 2.50 mmol), HOAc, 97% (0.72 mL, 12.5 mmol) and DCM (5 mL). The crude was submitted to flash chromatography using heptane and EtOAc (70/30-60/40) as eluent to give the titled compound (36 mg, 63%) as a solid; $^1$H NMR (400 MHz, CDCl$_3$): δ 3.64 (s, 2H), 4.54 (s, 2H), 5.18 (s, 2H), 7.16 (d, 2H), 7.23-7.29 (m, 3H), 7.29-7.35 (m, 3H), 7.37-7.43 (m, 3H), 7.60 (d, 2H), 8.03 (d, 1H); Mass spectrum: M–H⁺ 459.

Example 31

2-{3-[1-(4-Trifluoromethyl-phenyl)-ethoxycarbonylmethyl]phenylsulfanylmethyl}-benzoic acid

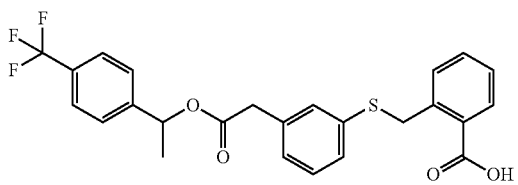

The titled compound was prepared according to the method described for example 1 above from 2-{3-[1-(4-Trifluoromethyl-phenyl)-ethoxycarbonylmethyl]phenylsulfanylmethyl}-benzoic acid 2,2,2-trichloro-ethyl ester (157 mg, 0.0.259 mmol), zinc (339 mg, 5.18 mmol), HOAc, 97% (1.48 mL, 25.9 mmol) and DCM (12 mL). The crude was submitted to flash chromatography using heptane and EtOAc (70/30-60/40) as eluent to give the titled compound (94 mg, 77%) as an oil; $^1$H NMR (400 MHz, CDCl$_3$): δ 1.53 (s, 3H), 3.60 (dd, 2H), 4.54 (dd, 2H), 5.91 (m, 1H), 7.07-7.12 (m, 1H), 7.15-7.20 (m, 2H), 7.21-7.32 (m, 3H), 7.35-7.42 (m, 3H), 7.58 (d, 2H), 7.98 (d, 1H); Mass spectrum: M–H⁺ 473.

Example 32

2-{3-[2-(4-Trifluoromethyl-phenyl)-ethoxycarbonylmethyl]-phenylsulfanylmethyl}-benzoic acid

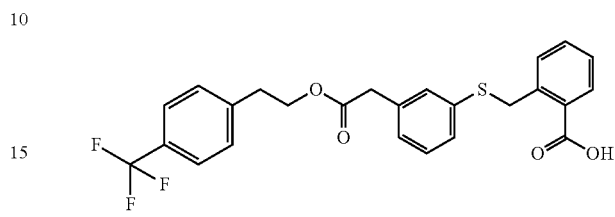

The titled compound was prepared according to the method described for example 1 above from 2-{3-[2-(4-trifluoromethyl-phenyl)-ethoxycarbonylmethyl]phenylsulfanylmethyl}-benzoic acid 2,2,2-trichloro-ethyl ester (160 mg, 0.264 mmol), zinc (345 mg, 5.28 mmol), HOAc, 97% (1.51 mL, 26.4 mmol) and DCM (12 mL). The crude was submitted to flash chromatography using heptane and EtOAc (70/30-60/40) as eluent to give the titled compound (87 mg, 69%) as an oil; $^1$H NMR (400 MHz, CDCl$_3$): δ 2.97 (dd, 2H), 3.54 (s, 2H), 4.34 (dd, 2H), 4.58 (s, 2H), 7.00-7.06 (m, 1H), 7.12-7.18 (m, 2H), 7.21-7.34 (m, 5H), 7.42 (dd, 1H), 7.52 (d, 2H), 7.98 (d, 1H); Mass spectrum: M–H⁺ 473.

General Procedure 1 (GP1)

Step 1

To the commercially available alcohols (0.288 mmol), placed in vials (20 mL) equipped with screw caps, were added a solution of 2-(4-carboxymethyl-phenylsulfanylmethyl)-benzoic acid 2,2,2-trichloro-ethyl ester (125 mg, 0.288 mmol), EDC×HCl (83 mg, 0.435 mmol), DMAP (3.5 mg, 0.029 mmol) and DCM (4 mL). The reaction mixtures were stirred at rt overnight. The mixtures were quenched with 0.25M HCl (4 mL) and the two phases were separated through phase separators. The organic phases were concentrated and used without further purification into the next step.

Step 2

The crudes from step 1 were dissolved in DCM (10 mL) and zinc (377 mg, 5.76 mmol) were added to each of the reactions followed by the addition of HOAc, 97% (1.65 mL). The reaction mixtures were stirred for 4 h, unless otherwise stated. The zinc were filtered off through phase separators. The filtrates, collected into new vials (40 mL), were washed with water and the two phases were separated through phase separators. The DCM were removed and the crudes were dissolved in DMSO (1.8 mL) before being purified by HPLC.

General Procedure 2 (GP2)

Step 1

To the commercially available alcohols (0.288 mmol), placed in vials (20 mL) equipped with screw caps, were added a solution of 2-(3-carboxymethyl-phenylsulfanylmethyl)-benzoic acid 2,2,2-trichloro-ethyl ester (125 mg, 0.288 mmol), EDC×HCl (83 mg, 0.435 mmol), DMAP (3.5 mg, 0.029 mmol) and DCM (4 mL). The reaction mixtures were stirred at rt overnight. The mixtures were quenched with 0.25M HCl (4 mL) and the two phases were separated through phase separators. The organic phases were concentrated and used without further purification into the next step.

Step 2

The crudes from step 1 were dissolved in DCM (10 mL) and zinc (377 mg, 5.76 mmol) were added to each of the reactions followed by the addition of HOAc, 97% (1.65 mL). The reaction mixtures were stirred for 4 h, unless otherwise stated. The zinc were filtered off through phase separators. The filtrates, collected into new vials (40 mL), were washed with water and the two phases were separated through phase separators. The DCM were removed and the crudes were dissolved in DMSO (1.8 mL) before being purified by HPLC.

Example 33

2-[4-(2,6-Dimethyl-benzyloxycarbonylmethyl)-phenylsulfanylmethyl]-benzoic acid

The titled compound was prepared according to GP1. Step 1: Using (2,6-dimethyl-phenyl)-methanol as the alcohol. Step 2: The reaction time was 2 days. Yield: 37 mg (31%). $^1$H NMR (600 MHz, $(CD_3)_2SO$, $(CH_3)_2SO$): δ 2.24 (s, 6H), 3.61 (s, 2H), 4.54 (s, 2H), 5.10 (s, 2H), 7.00 (d, 2H), 7.08-7.14 (m, 3H), 7.22 (d, 2H), 7.27-7.34 (m, 2H), 7.36-7.40 (m, 1H), 7.82 (d, 1H); Mass spectrum: M−H$^+$ 419.

Example 34

2-[4-(1-Phenyl-but-3-enyloxycarbonylmethyl)-phenylsulfanylmethyl]-benzoic acid

The titled compound was prepared according to GP1. Step 1: Using 1-phenyl-but-3-en-1-ol as the alcohol. Yield: 32 mg (26%). $^1$H NMR (600 MHz, $(CD_3)_2SO$, $(CH_3)_2SO$): δ 3.64 (s, 2H), 4.54 (s, 2H), 4.94-5.20 (m, 2H), 5.58-5.66 (m, 1H), 5.72 (t, 1H), 7.13 (d, 2H), 7.20-7.33 (m, 9H), 7.36-7.39 (m, 1H), 7.81 (d, 1H); Mass spectrum: M−H$^+$ 431.

Example 35

2-[3-(1-Methoxycarbonyl-2-phenyl-ethoxycarbonylmethyl)-phenylsulfanylmethyl]-benzoic acid The titled compound was prepared according to GP2. Step 1: Using 2-hydroxy-3-phenyl-propionic acid methyl ester as the alcohol. Step 2: The reaction time was 2 days. Yield: 43 mg (33%). $^1$H NMR (600 MHz, $(CD_3)_2SO$, $(CH_3)_2SO$): δ 2.99-3.10 (m, 2H), 3.59 (s, 3H), 3.64 (s, 2H), 4.54 (s, 2H), 5.14-5.18 (m, 1H), 6.94-6.97 (m, 1H), 7.11-7.25 (m, 8H), 7.29-7.34 (m, 2H), 7.36-7.40 (m, 1H), 7.81 (d, 1H); Mass spectrum: M−H$^+$ 463.

Example 36

2-{4-[2-(3,4-Dimethoxy-phenyl)-ethoxycarbonylmethyl]-phenylsulfanylmethyl}-benzoic acid The titled compound was prepared according to GP1. Step 1: Using 2-(3,4-dimethoxy-phenyl)-ethanol as the alcohol. Step 2: The reaction time was 10 days. Yield: 41 mg (30%). $^1$H NMR (600 MHz, $(CD_3)_2SO$, $(CH_3)_2SO$): δ 2.76 (t, 2H), 3.58 (s, 2H), 3.68 (s, 6H), 4.18 (t, 2H), 4.54 (s, 2H), 6.65 (d, 1H), 6.78-6.80 (m, 2H), 7.10 (d, 2H), 7.21 (d, 2H), 7.29-7.34 (m, 2H), 7.38-7.42 (m, 1H), 7.82 (d, 1H); Mass spectrum: M−H$^+$ 465.

Example 37

2-[4-(1-Methoxycarbonyl-2-phenylethoxycarbonylmethyl)phenylsulfanylmethyl]-benzoic acid The titled compound was prepared according to GP1. Step 1: Using 2-hydroxy-3-phenyl-propionic acid methyl ester as the alcohol. Yield: 45 mg (34%). $^1$H NMR (600 MHz, $(CD_3)_2SO$, $(CH_3)_2SO$): δ 2.98-3.10 (m, 2H), 3.60 (s, 3H), 3.63 (s, 2H), 4.54 (s, 2H), 5.15 (t, 1H), 7.05 (d, 2H), 7.12 (d, 2H), 7.18-7.24 (m, 5H), 7.30-7.34 (m, 2H), 7.38-7.42 (m, 1H), 7.82 (d, 1H); Mass spectrum: M−H$^+$ 463.

Example 38

2-{3-[2-(2-Trifluoromethylphenyl)ethoxycarbonylmethyl]phenylsulfanylmethyl}-benzoic acid The titled compound was prepared according to GP2. Step 1: Using 2-(2-trifluoromethyl-phenyl)-ethanol as the alcohol. Yield: 54 mg (40%). $^1$H NMR (600 MHz, $(CD_3)_2SO$, $(CH_3)_2SO$): δ 3.02 (t, 2H), 3.58 (s, 2H), 4.26 (t, 2H), 4.54 (s, 2H), 7.0 (d, 1H), 7.15-7.21 (m, 3H), 7.29-7.33 (m, 2H), 7.36-7.44 (m, 3H), 7.52-7.56 (m, 1H), 7.66 (d, 1H), 7.81 (d, 1H); Mass spectrum: M−H$^+$ 473.

Example 39

2-[4-(Oxazol-2-yl-phenyl-methoxycarbonylmethyl)-phenylsulfanylmethyl]-benzoic acid The titled compound was prepared according to GP1. Step 1: Using oxazol-2-yl-phenyl-methanol as the alcohol. Yield: 55 mg (42%). $^1$H NMR (600 MHz, $(CD_3)_2SO$, $(CH_3)_2SO$): δ 3.77 (d, 2H), 4.53 (s, 2H), 6.82 (s, 1H), 7.16 (d, 2H), 7.21 (s, 1H), 7.23 (d, 2H), 7.28-7.33 (m, 2H), 7.34-7.41 (m, 6H), 7.81 (d, 1H), 8.09 (s, 1H); Mass spectrum: M−H$^+$ 458.

Example 40

2-{4-[2-(2-Trifluoromethylphenyl)ethoxycarbonylmethyl]phenylsulfanylmethyl}-benzoic acid The titled compound was prepared according to GP1. Step 1: Using 2-(2-trifluoromethyl-phenyl)-ethanol as the alcohol. Step 2: The reaction time was 2 days. Yield: 41 mg (30%). $^1$H NMR (600 MHz, $(CD_3)_2SO$, $(CH_3)_2SO$): δ 3.02 (dd, 2H), 3.57 (s, 2H), 4.24 (dd, 2H), 4.54 (s, 2H), 7.09 (d, 2H), 7.21 (d, 2H), 7.30-7.34 (m, 2H), 7.38-7.43 (m, 3H), 7.53 (dd, 1H), 7.66 (d, 1H), 7.82 (d, 2H); Mass spectrum: M−H$^+$ 473.

Example 41

2-[3-(2,6-Dimethyl-benzyloxycarbonylmethyl)-phenylsulfanylmethyl]-benzoic acid

The titled compound was prepared according to GP2. Step 1: Using (2,6-dimethyl-phenyl)-methanol as the alcohol. Yield: 38 mg (31%). $^1$H NMR (600 MHz, $(CD_3)_2SO$, $(CH_3)_2SO$): δ 2.45 (s, 6H), 3.62 (s, 2H), 4.52 (s, 2H), 5.11 (s, 2H), 7.0 (d, 2H), 7.13 (d, 1H), 7.08-7.12 (m, 1H), 7.14-7.21 (m, 3H), 7.27-7.34 (m, 2H), 7.36-7.40 (m, 1H), 7.81 (d, 1H); Mass spectrum: M−H$^+$ 419.

Example 42

2-[3-(4-Pyrazol-1-yl-benzyloxycarbonylmethyl)-phenylsulfanylmethyl]-benzoic acid The titled compound was prepared according to GP2. Step 1: Using (4-pyrazol-1-yl-phenyl)-methanol as the alcohol. Yield: 56 mg (43%); Mass spectrum: M–H$^+$ 457.

Example 43

2-[4-(4-Pyrazol-1-yl-benzyloxycarbonylmethyl)-phenylsulfanylmethyl]-benzoic acid The titled compound was prepared according to GP1. Step 1: Using (4-pyrazol-1-yl-phenyl)-methanol as the alcohol. Yield: 52 mg (40%); Mass spectrum: M–H$^+$ 457.

Example 44

2-{3-[2-(3,4-Dimethoxy-phenyl)-ethoxycarbonylmethyl]-phenylsulfanylmethyl}-benzoic acid The titled compound was prepared according to GP2. Step 1: Using 2-(3,4-dimethoxy-phenyl)-ethanol as the alcohol. Yield: 47 mg (35.3%); Mass spectrum: M–H$^+$ 465.

Example 45

4-(1-Carboxy-1-methyl-ethoxy)-benzoic acid 4-methyl-2-(4-trifluoromethyl-phenyl)-thiazol-5-ylmethyl ester

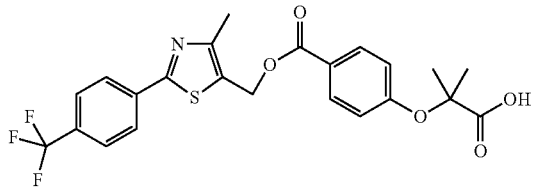 [SMILES: Cc1nc(-c2ccc(C(F)(F)F)cc2)sc1COC(=O)c1ccc(OC(C)(C)C(=O)O)cc1]

To a solution of 4-(1-tert-butoxycarbonyl-1-methyl-ethoxy)-benzoic acid 4-methyl-2-(4-trifluoro-methyl-phenyl)-thiazol-5-yl methyl ester (0.175 g, 0.327 mmol) in DCM (4 mL) trifluoroacetic acid (0.745 g, 6.53 mmol) was added and the mixture was stirred for 18 h at room temperature. After diluting with Et$_2$O the mixture was extracted with saturated aq. NaHCO$_3$. The organic layer was dried (Na$_2$SO$_4$) and evaporated and the obtained crude product was purified by HPLC. The title compound was obtained as a solid (10 mg, 6.4%). $^1$H NMR (500 MHz, CDCl$_3$): δ 7.99 (d, 2H), 7.96 (d, 2H), 7.64 (d, 2H), 6.89 (d, 2H), 5.46 (s, 2H), 2.55 (s, 3H), 1.66 (s, 6H).

Biological Activity

Transactivation Assay Expression vectors were prepared by inserting the ligand binding domain cDNA (complementary DNA) of human PPARalpha (amino acid 168-468) and human PPARgamma (amino acid 205-505), 3' to and in frame with, the yeast GAL4 transcription factor DNA binding domain and the nuclear localization signal from the T-antigen of Polyoma Virus into the mammalian expression vector pSGS (Stratagene). The resulting expression vectors pSG-GAL-PPARalpha and pSGGAL-PPARgamma were used in co-transfection experiments together with a modified pGL3 promoter plasmid (Promega) containing five copies of the UAS GAL4 recognition site. 2.5 µg pSGGAL-PPARalpha or pSGGAL-PPARgamma were mixed with 25 µg pGL3p 1×UAS and 22.5 µg pBluescript (Stratagene) in 0.95 mL ice cold PBS containing between 9-12 million U-2 OS (human osteosarcoma) cells. The cell/DNA mixture was incubated on ice for 5 minutes and then divided between two 0.4 cm cuvettes and electroporated at 960 µF, 230 V using a BioRad electroporator. The two electroporation mixes were combined in assay medium [Dulbecco's Modified Eagle Medium w/o phenol red, (Gibco 11880-028) including 10% FBS (Foetal Bovine Serum), 1% PEST (Penicillin & Streptomycin), 20 mM Hepes, 2 mM L-Glutamine and 0.36% Glucose (Gibco 31966-021)] at 0.32 million cells/ml. 25 µl diluted, electroporated cells, were seeded into 384-well plates and allowed to adhere for 3-4 h at 37° C., 5% CO$_2$ in a cell culture incubator. Test compounds in DMSO were diluted 40 fold in assay medium. 7 µl of diluted compound was added to the adhered electroporated cells and incubation was continued for 40 h in a cell culture incubator. Cells were lysed by adding 32 µl/well LucLite (Packard) and incubated at room temperature for 15 minutes. Luciferase activity was measured using a luminometry protocol on a Wallac Victor2 plate reader. 16 µM ETYA was used as the 100% control for humanPPARalpha activity and 16 µM Pioglitazone was used as the 100% control for humanPPARgamma activity.

In Vivo Assay

Determination of Plasma Clearance and Oral Bioavailability in Hamster or Mouse

Plasma clearance and oral bioavailability is estimated in Syrian male hamster or in female C57Bl/6 mice.

Hamsters are prepared 2 days prior to dosing by cannulation of the left carotid artery for blood sampling and, when applicable, by cannulation of the right jugular vein for intravenous administration. The cannulae are filled with heparin (100 IU/ml), extorized at the nape of the neck and sealed. The surgery is performed under isoflurane (Forene®, Abbott) anaesthesia. After surgery and under the experiment, the hamsters are housed individually and have free access to food and water.

Also mice have free access to food and water prior and during the experiment. Intravenous administration occurs in the tail vein. At pre-defined timepoints the mouse is anaesthetized with isoflurane and blood is taken from a vein.

The compound is dissolved in TEG:DMA:water (1:1:1) or another appropriate vehicle. For determination of plasma clearance the compound is administered as an intravenous (iv) bolus injection at a dose of ~2 µmol/kg. Blood samples are collected at frequent intervals up to at least 6 hours after drug administration. For bioavailability estimates the compound is administered orally at ~8 µmol/kg via gavage and blood samples are collected frequently up to at least 6 hours after dosing.

Blood samples are collected in heparinized tubes, kept on ice and centrifuged within 30 min for 5 min at 10000 g and 4° C. An aliquot of 50 µl plasma is transferred to 96-well plate and stored at −20° C. For analysis, samples are precipitated with 150 µl cold acetonitrile and centrifuged for 20 min at 2900 g. The supernatant is diluted 1:1 with water and analysed by LCMSMS. The concentrations of the soft drug and, if possible, at least of one of the expected metabolites, are determined using standard curves. The concentrations of the compound in the formulation are confirmed by LCMSMS.

The area under the plasma concentration-time curve following oral and intravenous administration, AUC$_{(0-t)}$, is calculated using a combination of the linear and logarithmic trapezoidal rule from the time of administration to the sampling time with the last determinable plasma concentration. For the intravenous bolus dose, the concentration at time zero, C(0), is estimated by log linear regression of the first two concentration-time points. The $AUC_{(0-t)}$ is extrapolated to AUC by adding $C_t/k$. $C_t$ is the predicted plasma concentration at the time of the last plasma sample with a determinable concentration, and k is the apparent terminal rate constant. $C_t$ and k were obtained by linear least squares regression analysis of the logarithm of the last 3 to 5 plasma concentrations versus time. The apparent terminal half-life $(t_{1/2})$ is calculated as ln 2/k.

The bioavailability (F) is calculated as $(AUC_{p.o.} \times Dose_{i.v., mean}/AUC_{i.v., mean} \times Dose_{p.o.}) \times 100\%$.

Estimates of total plasma clearance and of volumes of distribution are calculated from plasma concentration data obtained after intravenous administration of the test item. The total plasma clearance, CL, is calculated as $Dose_{i.v.}/AUC_{i.v.}$, and the apparent volume of distribution, $V_z$, as $Dose_{i.v.}/(k_{i.v.} \times AUC_{i.v.})$. The volume of distribution at steady state, $V_{ss}$, is calculated as $MRT_{i.v.} \times CL$. The mean residence time after intravenous administration, $MRT_{i.v.}$, is calculated as AUMC/AUC for bolus injection. After intravenous infusion, the mean residence time is calculated as $(AUMC/AUC)-t_{inf}/2$. AUMC is the area under the first-moment versus time curve.

Determination of In Vitro Stability

Liver microsomes are prepared from human liver samples according to internal SOPs, whereas Syrian male hamster liver microsomes are purchased (Biopredic). The compounds are incubated at 37° C. at a total microsome protein concentration of 0.5 mg/mL in a 0.1 mol/L potassium phosphate buffer at pH 7.4, in the presence of the cofactor, NADPH (1.0 mmol/L). The initial concentration of compound is 1.0 µmol/L. Samples are taken for analysis at 5 time points, 0, 7, 15, 20 and 30 minutes after the start of the incubation. The enzymatic activity in the collected sample is immediately stopped by adding acetonitrile (1:3.5), thereafter the sample is diluted 1:1 with water. The concentration of compound remaining in each of the collected samples is determined by means of LCMSMS. The elimination rate constant (k) of the soft drug is calculated as the slope of the plot of ln[soft drug] against incubation time (minutes). The elimination rate constant is then used to calculate the half-life $(T_{1/2})$ of the soft drug, which is subsequently used to calculate the intrinsic clearance (CLint) of the soft drug in liver microsomes as:

$CLint.=(\ln 2 \times incubation\ volume)/(T_{1/2} \times protein\ concentration)=\mu l/min/mg$ In Vitro Potency The compounds of formula I, XI, CI, MI have an $EC_{50}$ of less than 30 µmol/l for PPARα and/or γ in reporter gene assays (Table I). For example, the compounds of Example 1 and Example 14 have $EC_{50}$'s for PPARα of 0.24 µmol/l and 1.4 µmol/l, respectively and $EC_{50}$'s for PPARγ of 1.8 µmol/l and 0.11 µmol/l, respectively in reporter gene assays.

TABLE I

| Example | $EC_{50}$ PPARα (µmol/l) | $EC_{50}$ PPARγ (µmol/l) |
| --- | --- | --- |
| 1 | 0.24 | 1.8 |
| 2 | 0.24 | 1.7 |
| 3 | 0.056 | 1.7 |
| 4 | 1.4 | NT |
| 5 | 0.2 | 6 |
| 6 | 0.33 | 18 |
| 7 | 18 | 1.7 |
| 8 | 0.27 | 2.5 |
| 9 | 1.5 | 0.93 |
| 10 | 1.5 | 2.1 |
| 11 | 0.15 | 0.81 |
| 12 | NT | 0.058 |
| 13 | 0.012 | 0.03 |
| 14 | 1.4 | 0.11 |
| 15 | 0.13 | 0.84 |
| 16 | 1.1 | NT |
| 17 | 4.4 | 18 |
| 18 | 3.4 | NT |
| 19 | 0.072 | 0.47 |
| 20 | 0.84 | 0.072 |
| 21 | NT | NT |
| 22 | 18 | 18 |
| 23 | NT | 0.053 |
| 24 | NT | 0.0052 |
| 25 | NT | 0.043 |
| 26 | NT | 0.073 |
| 27 | NT | 1.4 |
| 28 | 1.3 | 2.5 |
| 29 | 0.029 | 0.76 |
| 30 | 0.16 | 1.7 |
| 31 | 18 | 3.5 |
| 32 | 5.5 | 3 |
| 33 | 0.62 | 18 |
| 34 | 18 | 15 |
| 35 | 22 | 6 |
| 36 | 21 | 7 |
| 37 | 2.2 | 3.9 |
| 38 | 3.8 | 9 |
| 39 | 13 | 18 |
| 40 | 0.76 | 8.2 |
| 41 | 15 | 3.8 |
| 42 | 18 | 4.2 |
| 43 | 16 | 4.2 |
| 44 | 18 | 11 |
| 45 | NT | NT |

(NT = not tested)

The skilled person will recognise that care needs to be taken when the activity of the compounds of formula (I), (XI), (CI), (MI) are measured in a cell based assay containing endogenous esterases. An observed lack of activity maybe due to how the compounds are affected by assay specific factors rather than inactivity of the compounds per se for example, ester hydrolysis during compound handling or susceptibility to inactivation during prolonged incubation times.

If necessary, the skilled person should be able to adapt the disclosed test conditions to make a suitable assessment of the compound activity, for example by adjusting the incubation time. Furthermore, it is anticipated that the compounds of formula (I), (XI), (CI), (MI) would have activity in a cell free assay, e.g. a binding assay.

Example of Binding Assay

The binding assay may be a scintillation proximity assay (SPA). In an SPA a protein is coated on scintillant incorporated beads. A radiolabelled ligand which can bind to the protein stimulates the beads to emit a signal. Binding affinities of unlabelled ligands can be determined by competitive displacement of the radioligand. These assays do not require separation of free from bound radioligand.

Recombinant 6-histidine tagged PPARLBD protein can be expressed and purified from *E. coli*.

Immobilisation of the PPAR protein on the beads can be achieved through electrostatic interactions using yttrium silicate SPA beads precoated with polylysine. Assays can be performed in multi-well format. Reaction mixes may contain, polylysine coated SPA beads, a fixed concentration of a tritiated PPAR ligand, recombinant 6-His PPAR and assay buffer.

The amounts and concentrations of the reaction mix components and incubation times are determined experimentally.

The formation of a radioligand/PPAR complex can be measured in a scintillation counter. Affinities of test compounds can be determined by incorporating increasing concentrations of unlabelled test compound into the assay which will lead to displacement of the radiolabelled ligand from the complex which is detected as loss of radioactive signal. Competition curves can be generated by plotting % binding versus concentration and equilibrium dissociation constants determined.

The invention claimed is:

1. A method of treatment of a disease or disorder selected from the group consisting of: Crohn's disease, ulcerative colitis, proctitis, gastric inflammation, celiac disease, appendicitis, microscopic colitis, distal proctitis, and indeterminant colitis in a mammal in need thereof, the method comprising administration of a therapeutically effective amount of a compound according general formula (I),

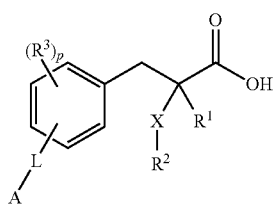

formula (I)

wherein:
$R^1$ represents H, F, $CH_3$ or $CF_3$;
X represents S, S(O) or $SO_2$;
$R^2$ represents $C_1$-$C_3$ alkylaryl or $C_1$-$C_3$ alkylheteroaryl, wherein aryl or heteroaryl each optionally is substituted by one or more of the following: halogen, OH, $OSO_2R^b$, $C_1$-$C_2$ alkoxy, $C_1$-$C_4$ alkyl, which $C_1$-$C_2$ alkoxy or $C_1$-$C_4$ alkyl substituents is each optionally substituted by one or more F;
$R^3$ is situated in the ortho, meta or para position and represents F, $C_1$-$C_4$ alkyl or $C_1$-$C_2$ alkoxy, which $C_1$-$C_4$ alkyl or $C_1$-$C_2$ alkoxy substituents is each optionally substituted by one or more F;
or $R^3$ is $CH_2Ph$, or $NHC(O)OC(CH_3)_3$;
p is an integer 0-4;
L is situated in the meta or para position and represents $(CH_2)_nC(O)O(CH_2)_i$, $(CH_2)_nC(O)S(CH_2)_i$, $(CH_2)_nOC(O)(CH_2)_i$ or $(CH_2)_nSC(O)(CH_2)_i$, each optionally substituted on any available carbon atom with one or more of the following substituents independently selected from: F, $C_2$-$C_3$ alkenyl, $C_1$-$C_3$ alkyl, $C_1$-$C_2$ alkoxy, which $C_1$-$C_3$ alkyl or $C_1$-$C_2$ alkoxy each optionally is substituted with one or more F;
n is an integer 0-3;
i is an integer 0-3;
A represents aryl or heteroaryl, each optionally substituted by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)$ $OR^b$, $OC(O)NR^aR^a$, $NR^aC(O)NR^aR^a$, $OSO_2R^b$, $NO_2$, $C_1$-$C_4$alkyl which is optionally substituted by one or more F; monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_1$-$C_4$alkyl which is optionally substituted by one or more F; monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $S(O)R^b$, $SO_2R^b$, $OSO_2R^b$, $NO_2$, $C(O)R^b$, $C_1$-$C_4$alkyl which is optionally substituted by one or more F, or A is cycloalkyl or heterocyclyl, each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, $C_1$-$C_4$alkyl which is optionally substituted by one or more F; monocyclic heterocyclyl, monocyclic cycloalkyl, wherein said monocyclic heterocyclyl or monocyclic cycloalkyl are each optionally substituted by one or more of the following independently selected from: F, OH, oxo, CN, $NR^aR^a$, $OR^b$, $SR^b$, $SiR^bR^bR^b$, $S(O)R^b$, $SO_2R^b$, $C(O)R^b$, $C_4$ alkyl which is optionally substituted by one or more F; monocyclic aryl, monocyclic heteroaryl, wherein said monocyclic aryl or monocyclic heteroaryl are each optionally substituted by one or more of the following independently selected from: halogens, OH, CN, $NR^aR^a$, $OR^b$, $SR^b$, $SiR^bR^bR^b$, $OS(O)R^b$, $S(O)R^b$, $SO_2R^b$, $NO_2$, $C(O)R^b$, $C_1$-$C_4$alkyl which is optionally substituted by one or more F;

and in the above definitions
$C_1$-$C_3$ alkylaryl binds to X via the alkyl chain;
$C_1$-$C_3$ alkylheteroaryl binds to X via the alkyl chain;
$R^a$ independently represents H or a straight or branched, saturated or unsaturated $C_1$-$C_4$ alkyl chain optionally substituted by one or more F; and
$R^b$ independently represents a straight or branched, saturated or unsaturated $C_1$-$C_4$ alkyl chain optionally substituted by one or more F;
or a pharmaceutically acceptable salt thereof.

2. The method according to claim 1, wherein
$R^1$ represents H;
X represents S or $SO_2$;
$R^2$ represents $C_2$alkylaryl, wherein aryl optionally is substituted by one or more of F;
L is situated in the meta or para position and represents $(CH_2)11C(O)O(CH_2)_i$, $(CH_2)_nOC(O)(CH_2)_i$, or $(CH_2)_nSC(O)(CH_2)_i$, each optionally substituted on any available carbon atom with one $C_1$alkyl;
n is an integer 0-2;
i is an integer 0-3;
p is 0;
A represents aryl or heteroaryl, each optionally substituted by one or more of the following: $OR^b$, $OSO_2R^b$, $C_1$-$C_4$alkyl (which is optionally substituted by one or more F); monocyclic aryl;
or A is heterocyclyl optionally substituted by $C_1$alkyl, which $C_i$ alkyl optionally is substituted by one or more F;
or a pharmaceutically acceptable salt thereof.

3. The method according to claim 1, wherein
$R^1$ represents H;
X represents S;
$R^2$ represents $C_2$alkylaryl, wherein aryl is substituted by one F;
L is situated in the meta or para position and represents $(CH_2)_nC(O)O(CH_2)_i$ or $(CH_2)_nOC(O)(CH_2)_i$;
n is an integer 0-1;
i is an integer 0-1;
p is 0;

A represents aryl or heteroaryl, each optionally substituted by one or more of the following: $OR^b$, $OSO_2R^b$, $C_1$alkyl (which is optionally substituted by one or more F); monocyclic aryl;

or A is heterocyclyl optionally substituted by $C_i$alkyl, which $C_1$alkyl optionally is substituted by one or more F;

or a pharmaceutically acceptable salt thereof.

4. The method of claim 1, wherein the disease or disorder is Crohn's disease.

5. The method of claim 1, wherein the disease or disorder is ulcerative colitis.

6. The method of claim 1, wherein the disease or disorder is proctitis.

7. The method of claim 1, wherein the disease or disorder is gastric inflammation.

8. The method of claim 1, wherein the disease or disorder is celiac disease.

9. The method of claim 1, wherein the disease or disorder is appendicitis.

10. The method of claim 1, wherein the disease or disorder is microscopic colitis.

11. The method of claim 1, wherein the disease or disorder is distal proctitis.

12. The method of claim 1, wherein the disease or disorder is indeterminant colitis.

13. A method of treatment for Crohn's disease, ulcerative colitis, proctitis, gastric inflammation, celiac disease, appendicitis, microscopic colitis, distal proctitis, or indeterminant colitis in a mammal in need thereof, the method comprising administration of a therapeutically effective amount of a compound selected from the group consisting of:

4-Methanesulfonyloxy-benzoic acid 4-{2-carboxy-2-[2-(4-fluoro-phenyl)-ethylsulfanyl]-ethyl}-benzyl ester;

2-[2-(4-Fluoro-phenyl)-ethylsulfanyl]-3-{4-[2-(4-methanesulfonyloxy-phenyl)-acetoxymethyl]-phenyl}-propionic acid;

2-[2-(4-Fluoro-phenyl)-ethylsulfanyl]-3-[4-(4-trifluoromethyl-benzyloxycarbonylmethyl)-phenyl]-propionic acid;

2-[2-(4-Fluoro-phenyl)-ethylsulfanyl]-3-[4-(4-methanesulfonyloxy-benzyloxycarbonylmethyl)-phenyl]-propionic acid;

2-[2-(4-Fluoro-phenyl)-ethylsulfanyl]-3-(4-{2-[2-(4-methanesulfonyloxy-phenyl)-acetoxy]-ethyl}-phenyl)-propionic acid;

2-[2-(4-Fluoro-phenyl)-ethylsulfanyl]-3-(4-{3-[2-(4-methanesulfonyloxy-phenyl)-acetoxy]-propyl}-phenyl)-propionic acid;

2-[2-(4-Fluoro-phenyl)-ethylsulfanyl]-3-[4-(2-phenyl-propionyloxymethyl)-phenyl]-propionic acid;

2-[2-(4-Fluoro-phenyl)-ethylsulfanyl]-3-{4-[2-(4-methoxylphenylacetoxymethyl]phenyl}-propionic acid;

2-[2-(4-Fluoro-phenyl)-ethylsulfanyl]-3-{4-[2-(4-isobutyl-phenyl)-propionyloxymethyl]-phenyl}-propionic acid;

2-[2-(4-Fluoro-phenyl)-ethylsulfanyl]-3-[4-(2-pyridin-2-yl-acetoxymethyl)-phenyl]-propionic acid;

2-[2-(4-Fluoro-phenyl)-ethylsulfanyl]-3-{4-[2-(4-methyl-piperazin-1-yl)-acetoxymethyl]-phenyl}-propionic acid;

4-{2-Carboxy-2-[2-(4-fluoro-phenyl)-ethylsulfanyl]-ethyl}-benzoic acid 2-phenyl-5 trifluoromethyl-oxazol-4-ylmethyl ester;

2-Phenyl-5-trifluoromethyl-oxazole-4-carboxylic acid 4-{2-carboxy-2-[2-(4-fluoro-phenyl)-ethylsulfanyl]-ethyl}-benzyl ester;

4-{2-Carboxy-2-[2-(4-fluoro-phenyl)-ethylsulfanyl]-ethyl}-benzoic acid 2-(5-methyl-2 phenyl-oxazol-4-yl)-ethyl ester;

2-[2-(4-Fluoro-phenyl)-ethylsulfanyl]-3-{4-[2-(5-methyl-2-phenyl-oxazol-4-yl) acetoxymethyl]-phenyl}-propionic acid;

4-{2-Carboxy-2-[2-(4-fluoro-phenyl)-ethylsulfanyl]-ethyl}-benzoic acid 4-methanesulfonyloxy-benzyl ester;

2-[2-(4-Fluoro-phenyl)-ethanesulfonyl]-3-[4-(4-trifluoromethyl-benzyloxycarbonylmethyl)-phenyl]-propionic acid;

2-[2-(4-Fluoro-phenyl)-ethylsulfanyl]-3-{4-[2-(4-methanesulfonyloxy-phenyl)-ethylsulfanylcarbonyl]-phenyl}-propionic acid;

(+2-[2-(4-Fluoro-phenyl)-ethylsulfanyl]-3-{4-[2-(5-methyl-2-phenyl-oxazol-4-yl)-acetoxymethyl]-phenyl}-propionic acid;

4-{(+2-Carboxy-2-[2-(4-fluoro-phenyl)-ethylsulfanyl]-ethyl}-benzoic acid 2-(5-methyl-2-phenyl-oxazol-4-yl)-ethyl ester;

(S)-2-Ethoxy-3-{4-[2-(5-methyl-2-phenyl-oxazol-4-yl)-acetoxy]-phenyl}-propionic acid;

(S)-3-{4-[2-(4-tert-Butoxycarbonylamino-phenyl)-acetoxy]-phenyl}-2-ethoxy-propionic acid;

3-{3-Benzyl-4-[2-(5-methyl-2-phenyl-oxazol-4-yl)-acetoxy]-phenyl}-2-ethoxy-propionic acid;

3-{3-Benzyl-4-[2-(4-tert-butoxycarbonylamino-phenyl)-acetoxy]-phenyl}-2-ethoxy-propionic acid;

2-Ethoxy-3-{3-methyl-4-[2-(5-methyl-2-phenyl-oxazol-4-yl)-acetoxy]-phenyl}-propionic acid;

3-{4-[2-(4-tert-Butoxycarbonylamino-phenyl)-acetoxy]-3-methyl-phenyl}-2-ethoxy-propionic acid;

4-(2-Carboxy-2-ethoxy-ethyl)-benzoic acid 4-methanesulfonyloxy-benzyl ester;

2-[3-(4-Trifluoromethyl-benzyloxycarbonylmethyl)-phenylsulfanylmethyl]-benzoic acid;

2-{4-[2-(4-Trifluoromethyl-phenyl)-acetoxymethyl]-phenylsulfanylmethyl}-benzoic acid;

2-[4-(4-Trifluoromethyl-benzyloxycarbonylmethyl)-phenylsulfanylmethyl]-benzoic acid;

2-{3-[1-(4-Trifluoromethyl-phenyl)-ethoxycarbonylmethyl]phenylsulfanylmethyl}-benzoic acid;

2-{3-[2-(4-Trifluoromethyl-phenyl)-ethoxycarbonylmethyl]-phenylsulfanylmethyl}-benzoic acid;

2-[4-(2,6-Dimethyl-benzyloxycarbonylmethyl)-phenylsulfanylmethyl]-benzoic acid;

2-[4-(1-Phenyl-but-3-enyloxycarbonylmethyl)-phenylsulfanylmethyl]-benzoic acid;

2-[3-(1-Methoxycarbonyl-2-phenyl-ethoxycarbonylmethyl)-phenylsulfanylmethyl]-benzoic acid;

2-{4-[2-(3,4-Dimethoxy-phenyl)-ethoxycarbonylmethyl]-phenylsulfanylmethyl}-benzoic acid;

2-[4-(1-Methoxycarbonyl-2-phenylethoxycarbonylmethyl)phenylsulfanylmethyl]-benzoic acid;

2-{3-[2-(2-Trifluoromethylphenyl)ethoxycarbonylmethyl]phenylsulfanylmethyl}-benzoic acid;

2-[4-(Oxazol-2-yl-phenyl-methoxycarbonylmethyl)-phenylsulfanylmethyl]-benzoic acid;

2-{4-[2-(2-Trifluoromethylphenyl)ethoxycarbonylmethyl]phenylsulfanylmethyl}-benzoic acid;

2-[3-(2,6-Dimethyl-benzyloxycarbonylmethyl)-phenylsulfanylmethyl]-benzoic acid;

2-[3-(4-Pyrazol-1-yl-benzyloxycarbonylmethyl)-phenylsulfanylmethyl]-benzoic acid;

2-[4-(4-Pyrazol-1-yl-benzyloxycarbonylmethyl)-phenylsulfanylmethyl]-benzoic acid; or 2-{3-[2-(3,4-Dimethoxy-phenyl)-ethoxycarbonylmethyl]-phenylsulfanylmethyl}-benzoic acid; and 4-(1-Carboxy-1-methyl-ethoxy)-benzoic acid 4-methyl-2-(4-trifluoromethyl-phenyl)-thiazol-5-ylmethyl ester;

or a pharmaceutically acceptable salt thereof.

14. The method of claim 13, wherein the disease or disorder is Crohn's disease.

15. The method of claim 13, wherein the disease or disorder is ulcerative colitis.

16. The method of claim 13, wherein the disease or disorder is proctitis.

17. The method of claim 13, wherein the disease or disorder is gastric inflammation.

18. The method of claim 13, wherein the disease or disorder is celiac disease.

19. The method of claim 13, wherein the disease or disorder is appendicitis.

20. The method of claim 13, wherein the disease or disorder is microscopic colitis.

21. The method of claim 13, wherein the disease or disorder is distal proctitis.

22. The method of claim 13, wherein the disease or disorder is indeterminant colitis.

\* \* \* \* \*